US009624255B2

(12) United States Patent
Hecht et al.

(10) Patent No.: US 9,624,255 B2
(45) Date of Patent: Apr. 18, 2017

(54) CARBOHYDRATE-MEDIATED TUMOR TARGETING

(75) Inventors: Sidney Hecht, Phoenix, AZ (US); Ryan Schmaltz, La Jolla, CA (US); Krystal Tsosie, Phoenix, AZ (US)

(73) Assignee: Arizona Board of Regents, Scottsdale, AZ (US)

( * ) Notice: Subject to any disclaimer, the term of this patent is extended or adjusted under 35 U.S.C. 154(b) by 1448 days.

(21) Appl. No.: 13/382,581

(22) PCT Filed: May 5, 2010

(86) PCT No.: PCT/US2010/033651
§ 371 (c)(1),
(2), (4) Date: Feb. 2, 2012

(87) PCT Pub. No.: WO2011/019419
PCT Pub. Date: Feb. 17, 2011

(65) Prior Publication Data
US 2012/0148502 A1 Jun. 14, 2012

Related U.S. Application Data

(60) Provisional application No. 61/232,858, filed on Aug. 11, 2009.

(51) Int. Cl.
*A61K 9/00* (2006.01)
*C07H 15/26* (2006.01)
(Continued)

(52) U.S. Cl.
CPC ....... *C07H 15/26* (2013.01); *A61K 47/48869* (2013.01); *C07H 13/04* (2013.01); *C07H 13/12* (2013.01); *C07H 15/18* (2013.01)

(58) Field of Classification Search
CPC .................................................... C07H 15/26
See application file for complete search history.

(56) References Cited

U.S. PATENT DOCUMENTS 5,420,228 A 5/1995 Lazo

FOREIGN PATENT DOCUMENTS

WO 96/39197 12/1996

OTHER PUBLICATIONS

Karche, Synthesis of beta-CF2-delta-Mannapyranosides and beta-CF2-delta-Galactopyranosides by Reformatsky ADdition onto 5-Ketohexoses, Synlett, 2007, 1, 123-126.*

(Continued)

*Primary Examiner* — Paul Dickinson
(74) *Attorney, Agent, or Firm* — Byrne Poh LLP; Nina R. Horan

(57) ABSTRACT

Tumors can be selectively targeted via compounds provided herein according to the formula, or a pharmaceutically acceptable salt thereof, wherein $R^A$ and $R^B$ are as defined herein. Tumors can be imaged or targeted for therapeutic treatment using compounds described herein where at least one $R^A$ or at least one $R^B$ group comprises a imaging agent, a therapeutic agent, or a member of a specific binding pair which can be associated with a secondary imaging agent, such as a microbubble for ultrasonic imaging.

35 Claims, 11 Drawing Sheets

(51) Int. Cl.
A61K 47/48 (2006.01)
C07H 13/04 (2006.01)
C07H 13/12 (2006.01)
C07H 15/18 (2006.01)

(56) References Cited

OTHER PUBLICATIONS

Fang, The Sterochemcial Dependence of Unimolecular Dissociation of Monosaccharide-Glycolaldehyde Anions in the Gas Phase, J. Am. Chem. Soc, 2007, 129, 9721-9736.*
Kite, Data-directed scan sequence for the general assignment of C-glycosylflavone O-glycosies in plant extracts by liquid chromatography-ion traip mass spectrometery, Journal of Chromatography A, 2006, 1104, 123-131.*
Umezawa. Recent advances in antitumor antibiotics. Antibiot. Chemother. (1978), 23, 76-87.
Sikic. Bleomycin Chemotherapy; Academic Press: Orlando, FL, 1985. 305-310.
Levi. The Importance of Bleomycin in Combination Chemotherapy for Good-Prognosis Germ Cell Carcinoma. J. Clin. Oncol. (1993), 11, 1300-1305.
Stubbe. 'Mechanisms of bleomycin-induced DNA degradation' Chem. Rev. (1987), 87, 1107-1136.
Kane. Polynucleotide recognition and degradation by bleomycin. Prog. Nucleic Acid Res. Mol. Biol. (1994), 49, 313-352.
Claussen. Nucleic Acid Recognition by Metal Complexes of Bleomycin. Chem. Rev. (1999), 99, 2797-2816.
Hecht. Bleomycin: New Perspectives on the Mechanism of Action J. Nat. Prod. (2000), 63, 158-168.
Chen. Bleomycins: towards better therapeutics J. Nature Rev. (2005), 5, 102-112.
Carter. Site-specific cleavage of RNA by Fe(II)bleomycin. Proc. Natl. Acad. Sci. U. S. A. (1990), 87, 9373-9377.
Holmes. Characterization of Iron(II)Bleomycin-Mediated RNA Strand Scission. Biochemistry (1993), 32, 4293-4307.
Hecht. RNA Degradation by Bleomycin, a Naturally Occurring Bioconjugate Chem. (1994), 5, 513-526.
Abraham. RNA Cleavage and Inhibition of Protein Synthesis by Bleomycin. Chem. Biol. (2003), 10, 45-52.
Tao. An Efficient Mammalian Transfer RNA Target for Bleomycin. J. Am. Chem. Soc. (2006), 128, 14806-14807.
Carter. A role for the metal binding domain in determining the DNA sequence selectivity of Fe-bleomycin. J. Biol. Chem. (1990), 265, 4193-4196.
Carter. Polynucleotide recognition and strand scission by Fe-bleomycin Tetrahedron, (1991), 47, 2463-2474.
Kane. On the Role of the Bithiazole Moiety in Sequence-selective DNA Cleavage by FeBleomycin. J. Biol. Chem. (1994), 269, 10899-10904.
Oppenheimer Structural studies of of "active complex" of bleomycin: assignment of ligands to the ferrous ion in a ferrous-bleomycin-carbon monoxide complex Proc. Natl. Acad. Sci. U.S.A. 1979, 76, 5616-5620.
Ehrenfeld. Studies on bleomycin and tRNA [superscript Gly]. Ph. D. Thesis, University of Virginia, 1986. 157-159.
Umezawa. Natural and Artificial Bleomycins: Chemistry and Antitumour Activities Pure Appl. Chem. (1971), 28, 665-680.
Jones. Indium-111 bleomycin tumor scanning in lymphoma Med. Ped. Oncol. (1975), 1, 11-21.
Silverstein. Indium-bleomycin breast and axilla imaging. Cancer (1976), 37, 36-42.
Van De Poll. Labelling of bleomycin with cobalt-57, indium-111, technetium-99m, mercury-197, lead-203, and copper-67. Nuclear Medicine, 1976, 15, 86-90.
Rasker. Cobalt-57-bleomycin scanning of hila and mediastinum in patients with bronchial carcinoma: a prospective study. Thorax (1976), 31, 641-649.
Oyama. [Tumor imaging agent: 111In-bleomycin (author's transl)]. Radioisotopes 1976, 25, 567-570.
Burton. Static and dynamic imaging with indium-III labelled Bleomycin in the localization of squamous cell neoplasia Brit. J. Radiol. 1977, 50, 508-512.
Tonami. [Detection of intracranial lesions with 111-In bleomycin—comparison with 99mTc-pertechnetate]. Jap. J. Nucl. Med. 1977, 14, 217-221.
Firusian. [Localization diagnostics of malignant tumors using radioactive bleomycin (author's transl)]. Strahlentherapie 1977, 153, 331-341.
Bekerman. Scintigraphic Evaluation of Lymphoma: A Compartive Study of Ga-Citrate and In-Bleomycin Radiology 1977, 123, 687-694.
Stern. Cytotoxic activity, tumor accumulation, and tissue distribution of ruthenium-103-labeled bleomycin J. Nat. Cancer Inst. 1981, 66, 807-811.
Lindner. Microbubbles in medical imaging: current applications and future directions. Nat. Rev. Drug Discov. (2004), 3, 527-532.
Rychak. Deformable gas-filled microbubbles targetd to P-selectin. J Control Rel (2006), 114, 288-299.
Hamilton. Intravascular ultrasound molecular imaging of atheroma components in vivo. J. Am. Coll. Cardiol. (2004), 43, 453-460.
Chapuis. Carbohydrate Dependent Targeting of Cancer Cells by Bleomycin-Microbubble Conjugates J. Am. Chem. Soc. (2009), 131, 2438-2439.
Boger. Total Synthesis of Bleomycin A2 and Related Agents. 1. Synthesis and DNA Binding Properties of the Extended C-Terminus: Tripeptide S, Tetrapeptide S, Pentapeptide S, and Related Agents. J. Am. Chem. Soc. (1994),116, 5607-5618.
Lenkinski. Interactions of Gallium(III) with Bleomycin Antibiotics. J. Am. Chem. Soc. (1980), 102,131-135.
Christensen. Circulation (2002), 96, 473-82.
Klibanov. Bioconjugate Chem., (2005), 16, 9-17.
Gao. Ultrasonics (2008), 48, 260-270.
Hwang. Development and Evaluation of Perfluorocarbon Nanobubbles for Apomorphine Delivery, J. Pharm. Sci. (2009).
Rapoport. J. Natl. Cancer Inst. (2007), 99, 1095-1106.
ISR for PCT/US10/33651, mailed Oct. 11, 2010.

* cited by examiner

A1

A2

B1

B2

D1

D2

CARBOHYDRATE-MEDIATED TUMOR TARGETING

CROSS-REFERENCE TO RELATED APPLICATIONS

This application claims priority to U.S. Provisional Ser. No. 61/232,858 filed Aug. 11, 2009, incorporated by reference herein in its entirety.

FIELD OF THE INVENTION

The invention relates to compounds comprising the disaccharide moiety of bleomycin and reagents and methods for imaging and targeting tumor cells utilizing the same.

BACKGROUND OF THE INVENTION

The bleomycins (BLMs) are antineoplastic agents whose antitumor activity is recognized in the treatment of squamous cell carcinomas and malignant lymphomas (see, Umezawa, H. *Antibiot. Chemother.* 1978, 23, 76; Sikic et al., Eds. *Bleomycin Chemotherapy*; Academic Press: Orlando, Fla., 1985; Levi et al., *J. Clin. Oncol.* 1993, 11, 1300). The therapeutic effect of bleomycin analogues is believed to result from their selective oxidative cleavage of DNA (see, Stubbe et al., *Chem. Rev.* 1987, 87, 1107; Kane et al., *Prog. Nucleic Acid Res. Mol. Biol.* 1994, 49, 313; Claussen et al., *Chem. Rev.* 1999, 99, 2797; Hecht, S. M. *J. Nat. Prod.* 2000, 63, 158; and Chen et al., *Nature Rev.* 2005, 5, 102) and possibly also RNA (see, Carter et al., *Proc. Natl. Acad. Sci. U.S.A.* 1990, 87, 9373; Holmes et al., *Biochemistry* 1993, 32, 4293; Hecht, S. M. *Bioconjugate Chem.* 1994, 5, 513; Abraham et al., *Chem. Biol.* 2003, 10, 45; and Tao et al., *J. Am. Chem. Soc.* 2006, 128, 14806). Much of the site-specific cleavage activity is thought to be effected by the N-terminal metal-binding domain, the C-terminal bithiazole region, and the linker domain (see, Carter et al., *J. Biol. Chem.* 1990, 265, 4193; Carter et al., *Tetrahedron*, 1991, 47, 2463; and Kane et al., *J. Biol. Chem.* 1994, 269, 10899). The least understood structural domain of BLM is the disaccharide moiety.

There is a carbamoyl group at the 3-position in the D-mannose moiety of the disaccharide that is thought to participate in coordination to a variety of metal ions (see, Oppenheimer et al., *Proc. Natl. Acad. Sci. U.S.A.* 1979, 76, 5616). However, this does not appear to be the sole explanation for the presence of this sugar moiety as BLM and deglycoBLM (i.e., the BLM congener lacking the disaccharide) show similar cleavage efficacy in vitro (see, Ehrenfeld, G. M., Ph.D. Thesis, University of Virginia, 1986).

This ability of bleomycin to accumulate selectively on the surface or within tumor cells (see, Umezawa, H. *Pure Appl. Chem.* 1971, 28, 665) has been documented in numerous tumor imaging studies that utilized radionuclides bound to BLM (see, Jones et al., *Med. Ped. Oncol.* 1975, 1, 11; Silverstein et al., *Cancer* 1976, 37, 36; van de Poll et al., *Nuclear-Medizin* 1976, 15, 86; Rasker et al., *Thorax* 1976, 31, 641; Oyama et al., *Radioisotopes* 1976, 25, 567; Burton et al., *Brit. J. Radiol.* 1977, 50, 508; Tonami et al., *Jap. J. Nucl. Med.* 1977, 14, 217; Firusian et al., *Strahlentherapie* 1977, 153, 331; Bekerman et al., *Radiology* 1977, 123, 687; Stern et al., *J. Nat. Cancer Inst.* 1981, 66, 807; and Linder et al., *J. Nat. Rev. Drug Discov.* 2004, 3, 527). The innate tumor targeting nature of bleomycin is important in the design of synthetic analogues with improved properties. If the molecular basis of tumor targeting were understood it might also enable the selective delivery of other probes and drugs to tumor cells.

The tumor-specific behavior of bleomycin can be visualized by surface-conjugation of microbubbles. Microbubbles, usually consisting of a lipid-based shell encompassing an inert perfluorocarbon gas core (see, Rychak et al., *J Control Rel* 2006, 114, 288), were originally designed to improve the diagnostic ultrasound imaging of pathologic diseases within the human microvasculature (see, Hamilton et al., *J. Am. Coll. Cardiol.* 2004, 43, 453). While individual microbubbles may exist in varying sizes, they are usually smaller than red blood cells with a mean diameter typically within the range of 1-4 µm. With these inherent characteristics, microbubbles are generally regarded as pure intravascular tracers that travel freely within the (micro)circulation. Upon recognition of this behavior, there have been many efforts to direct microbubble attachment to specific cell types of interest by modifying the microbubble surface with different receptors, usually monoclonal antibodies. Initial studies have demonstrated that BLM tethered to a microbubble can adhere to tumor cells selectively (see, Chapuis et al., *J. Am. Chem. Soc.* 2009, 131, 2438).

SUMMARY OF THE INVENTION

Presently, described herein is the surprising and unanticipated finding that the carbohydrate moiety of BLM by itself is sufficient for tumor cell targeting.

In one aspect of the invention, compounds are provided according to the formula,

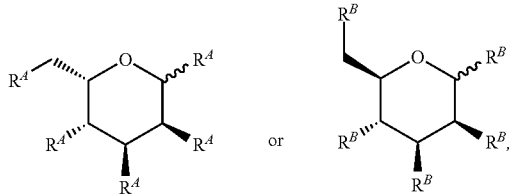

an epimer thereof, or a pharmaceutically acceptable salt thereof, wherein $R^A$ and $R^B$ are as defined herein.

In a second aspect of the invention, compounds are provided according to the formula,

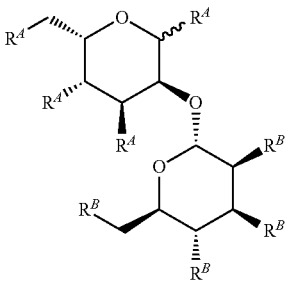

or an epimer thereof, wherein $R^A$ and $R^B$ are as defined herein.

In a third aspect of the invention, pharmaceutical compositions are provided comprising a compound according to the first aspect of the invention, wherein at least one $R^A$ or at least one $R^B$ comprises a chemotherapeutic agent, and a pharmaceutically acceptable diluent, carrier, or excipient.

In a fourth aspect of the invention, compositions are provided comprising a compound according to the first aspect of the invention, wherein at least one $R^A$ or at least one $R^B$ comprises an imaging agent, and a pharmaceutically acceptable diluent, carrier, or excipient.

In a fifth aspect of the invention, microbubble conjugates are provided comprising (a) a microbubble comprising an outer shell, wherein the outer shell is derivatized with a first member of a specific binding pair; and bound to the microbubble, (b) a compound according to the first aspect of the invention, wherein at least one $R^A$ or at least one $R^B$ comprises a second member of the specific binding pair, wherein the first member of the specific binding pair and the second member of the specific binding pair are bound to each other.

In a sixth aspect of the invention, microbubble conjugates are provided comprising (a) a microbubble comprising an outer shell, wherein the outer shell is derivatized with a first member of a first specific binding pair; (b) a first compound according to the first aspect of the invention, wherein at least one $R^A$ or at least one $R^B$ comprises a first member of a second specific binding pair, and (c) a second compound comprising the second members of the first and second specific binding pairs, wherein the second members of the specific binding pairs bind to both first members of the first and second specific binding pairs, thereby binding the first compound to the microbubble.

In a seventh aspect of the invention, compositions are provided comprising a microbubble conjugate according to the fifth or sixth aspects of the invention, and a pharmaceutically acceptable diluent, carrier, or excipient.

In an eighth aspect, the present invention provides methods for selectively imaging a tumor in a patient comprising, administering to a subject with a tumor a compound according to the first aspect of the invention, wherein at least one $R^A$ or at least one $R^B$ comprises an imaging agent, or a composition according to the fourth aspect of the invention, under conditions suitable to promote binding of the compound to the tumor; and detecting a signal from the imaging agent.

In a ninth aspect, the present invention provides methods for selectively imaging a tumor in a patient, comprising administering to a subject with a tumor a microbubble conjugate according to the fifth or sixth aspects of the invention of the invention or a composition according to the seventh aspect of the invention, under conditions suitable to promote binding of the microbubble conjugate to the tumor; and (b) acquiring an image (e.g., ultrasound) of the composition in the subject.

In a tenth aspect of the invention, methods for treating a cancer in a patient in need of such treatment are provided comprising administering to the patient a therapeutically effective amount of a compound according to the first aspect of the invention or a pharmaceutical composition according to the third aspect of the invention, wherein at least one $R^A$ or at least one $R^B$ comprises a chemotherapeutic agent.

DETAILED DESCRIPTION OF THE INVENTION

Figure 1:
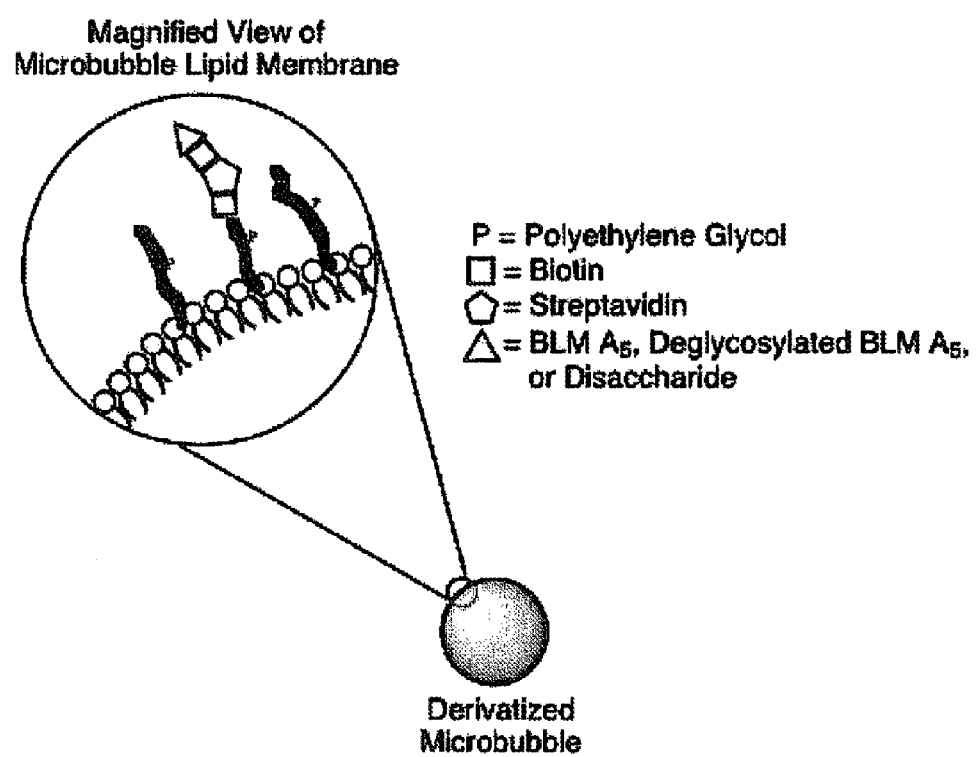
FIG. 1 illustrates the constitution of microbubbles derivatized with biotinylated compounds bleomycin $A_5$, deglyco BLM $A_5$, or the bleomycin disaccharide.

In embodiment (1) of the first aspect, the present disclosure provides compounds of formula (I) or (I'),

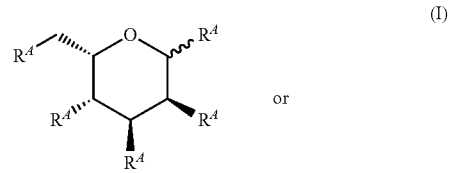

(I)

or

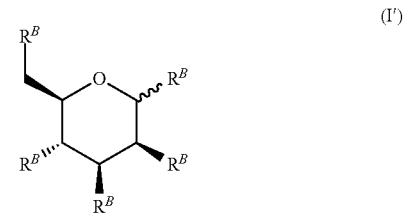

(I')

an epimer thereof, or a pharmaceutically acceptable salt thereof, wherein each $R^A$ is independently hydrogen, —$OR^1$, —N(H)($R^1$), or —$R^4$, wherein each $R^1$ is independently hydrogen, a protecting group, —$R^3$, —$R^4$, or —$R^{5a}$, wherein $R^{5a}$ is

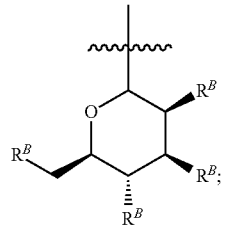

each $R^B$ is independently hydrogen, —$OR^2$, —N(H)($R^2$), or —$R^4$, wherein each $R^2$ is independently hydrogen, a protecting group, —$R^3$, —$R^4$, or —$R^{5b}$, wherein $R^{5b}$ is

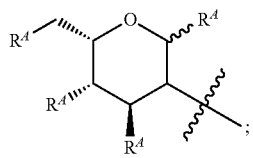

$R^3$ is —C(O)$OR^{30}$, —C(O)N(H)($R^{30}$), —S(O)$OR^{30}$, —S(O)$_2OR^{30}$, —S(O)N(H)($R^{30}$), —S(O)$_2$N(H)($R^{30}$), or —P(O)(O$R^{30}$)$_2$, wherein
$R^{30}$ is hydrogen, $C_1$-$C_6$ alkyl, $C_1$-$C_6$ haloalkyl, aryl, heteroaryl, $C_3$-$C_8$ cycloalkyl, or heterocyclyl, wherein $R^{30}$ is optionally substituted with one to four groups which are each independently $C_1$-$C_6$ alkyl, cyano, nitro, halogen, —$OR^{31}$, —N($R^{31}$)$_2$, —S$R^{31}$, —C(O)$R^{31}$, —C(O)$OR^{31}$, —C(O)N($R^{31}$)$_2$, —OC(O)$OR^{31}$, —OC(O)N($R^{31}$)$_2$, —N($R^{31}$)C(O)$OR^{31}$, —N($R^{31}$)C(O)N($R^{31}$)$_2$, —S(O)$R^{31}$, —S(O)$_2R^{31}$, —S(O)N($R^{31}$)$_2$, or —S(O)$_2$N($R^{31}$)$_2$, wherein each $R^{31}$ is independently hydrogen or $C_1$-$C_6$ alkyl;
each $R^4$ is independently -L-($R^{40}$)$_q$, wherein
each q is independently one or greater;
each L is independently a bond or a linker, provided that when L is a bond, then q is 1;
and
each $R^{40}$ is independently an imaging agent, a member of a specific binding pair, a chemotherapeutic agent, or —$R^{41}$, wherein
$R^{41}$ is —OH, —NH($R^{42}$), —SH, —C(O)H, —C(O)$OR^{42}$, —C(O)NH($R^{42}$), —OC(O)$OR^{42}$, —OC(O)N($R^{42}$)$_2$, —N($R^{42}$)C(O)$OR^{42}$, —N($R^{42}$)C(O)N($R^{42}$)$_2$, —S(O)N($R^{42}$)$_2$, or —S(O)$_2$N($R^{42}$)$_2$, wherein each $R^{42}$ is independently hydrogen, $C_1$-$C_6$ alkyl, or benzyl; and
provided that
(i) no more than one $R^1$ is $R^{5a}$ and no more than one $R^2$ is $R^{5b}$;
(ii) when one $R^1$ group is $R^{5a}$, then $R^2$ is not $R^{5b}$; and when one $R^2$ group is $R^{5b}$, then $R^1$ is not $R^{5a}$;
(iii) no more than one $R^3$ group is present;
(iv) at least one $R^4$ is present;
(v) no more than one $R^A$, and no more than one $R^B$ comprises $R^4$;
(vi) no more than two $R^A$ groups and no more than two $R^B$ groups are hydrogen;

(vii) $R^{40}$ is not (a) $R^{41}$ when L is a bond; and (b) bleomycin; and
(viii) the compound of formula (I) or (I') is not bleomycin.

The invention further comprises preferred subgenera of embodiment (1) of the first aspect in which the substituents are selected as any and all combinations of structural formula (I) and (I'), $R^A$ and $R^B$ as defined herein, including without limitation, the following:

Structural Formula (I) is One of Formulae (Ia)-(In):

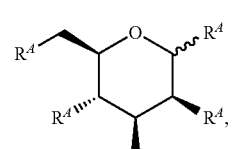
(Ia)

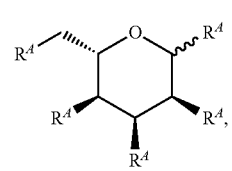
(Ib)

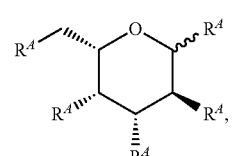
(Ic)

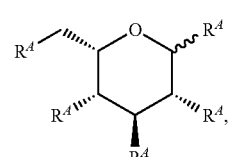
(Id)

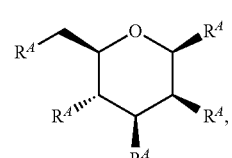
(Ie)

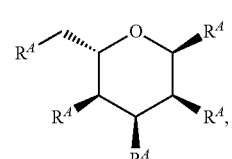
(If)

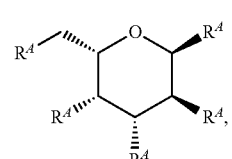
(Ig)

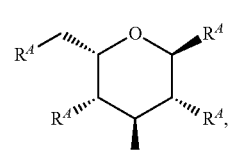
(Ih)

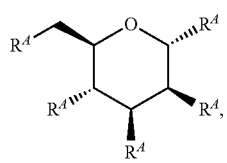 (Ii)
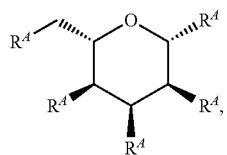 (Ij)
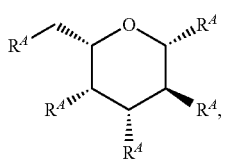 (Ik)
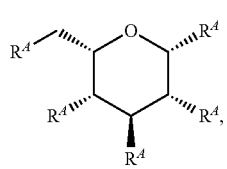 (Il)
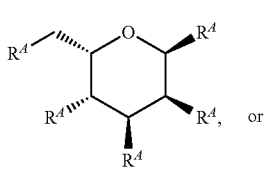 (Im) or
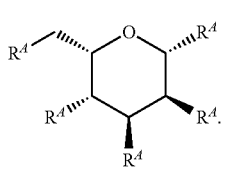 (In).
Structural Formula (I') is One of Formulae (Io)-(Ibb):
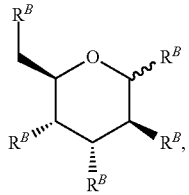 (Iq)
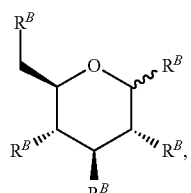 (Ir)
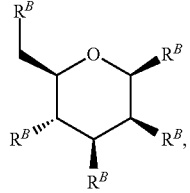 (Is)
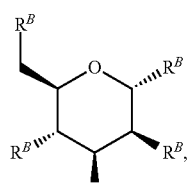 (It)
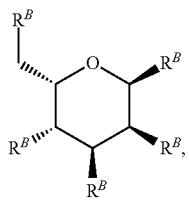 (Iu)
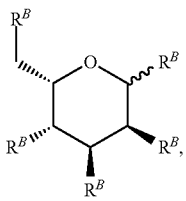 (Io)
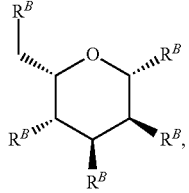 (Iv)
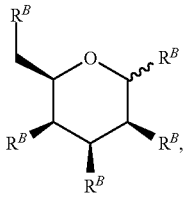 (Ip)
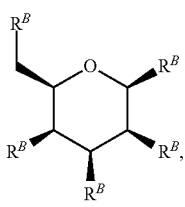 (Iw)

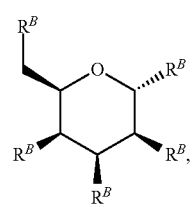
(Ix)
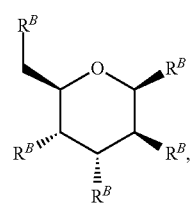
(Iy)
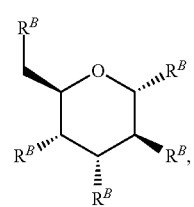
(Iz)
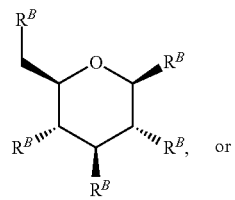
(Iaa) or
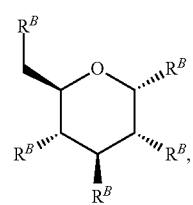
(Ibb)
Structural Formula (I) or (I') is One of Formulae (Icc)-(Ieee):
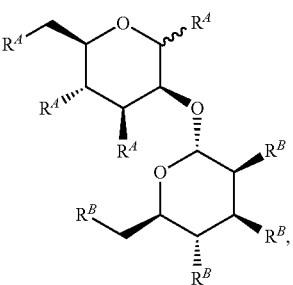
(Icc)
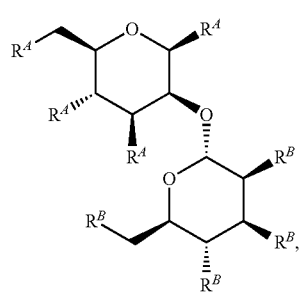
(Idd)
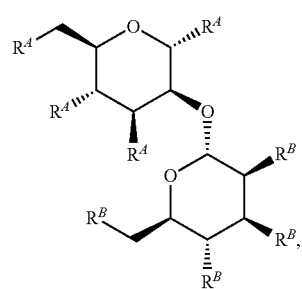
(Iee)
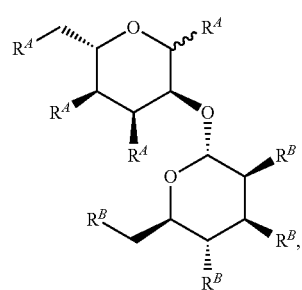
(Iff)
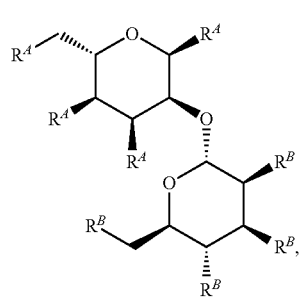
(Igg)
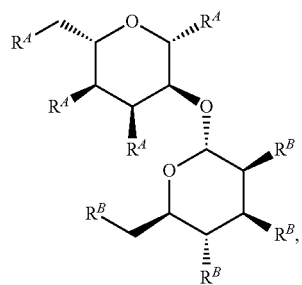
(Ihh)

-continued
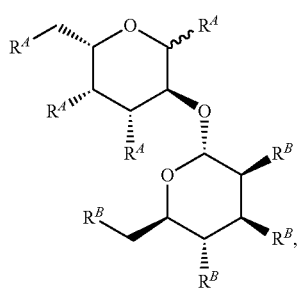 (Iii)
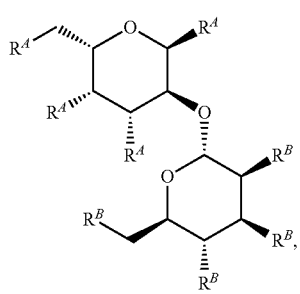 (Ijj)
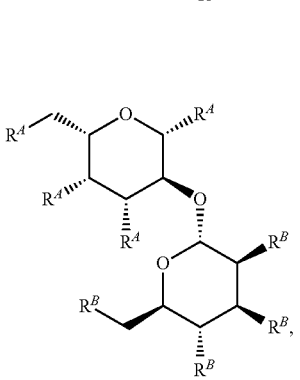 (Ikk)
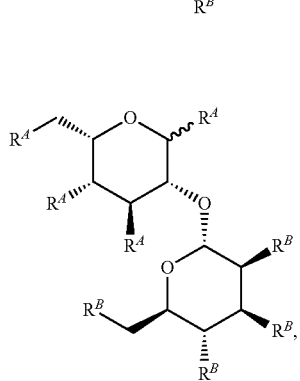 (Ill)
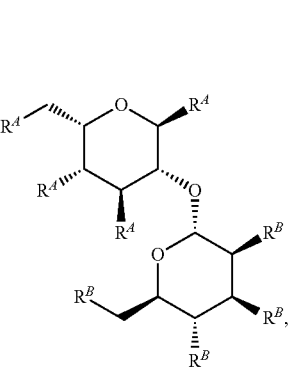 (Imm)
-continued
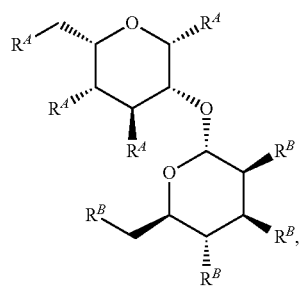 (Inn)
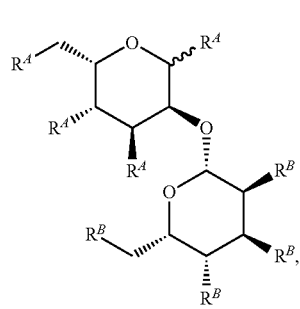 (Ioo)
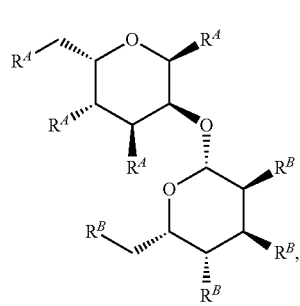 (Ipp)
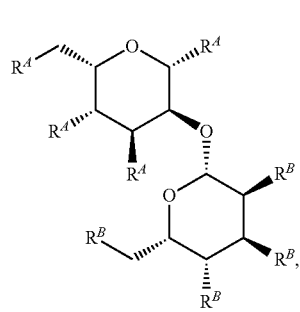 (Iqq)
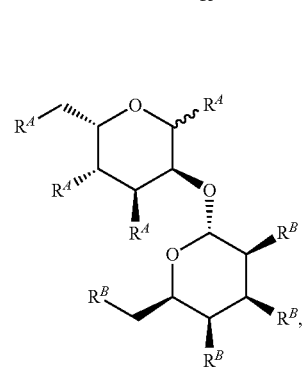 (Irr)

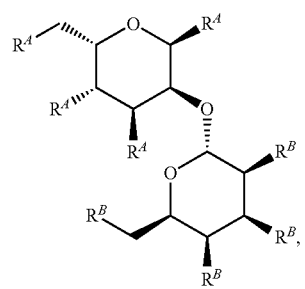
(Iss)
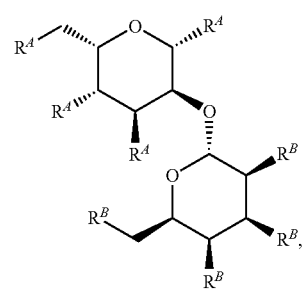
(Itt)
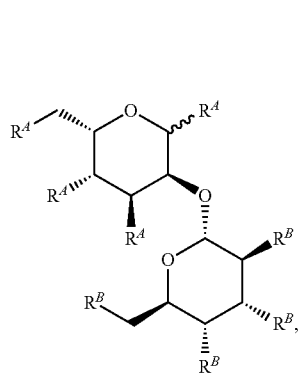
(Iuu)
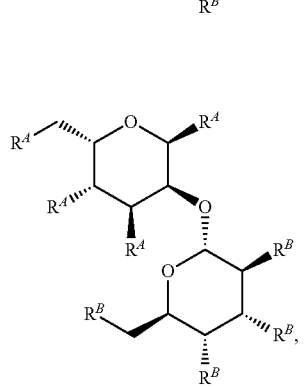
(Ivv)
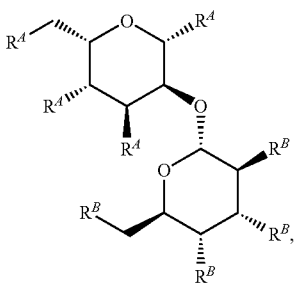
(Iww)
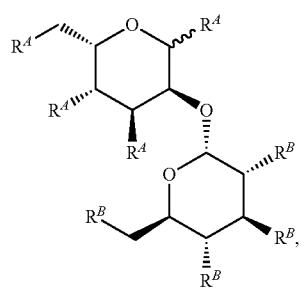
(Ixx)
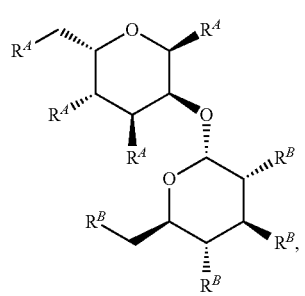
(Iyy)
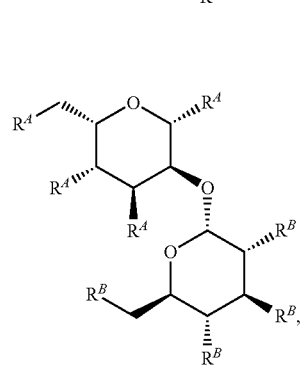
(Izz)
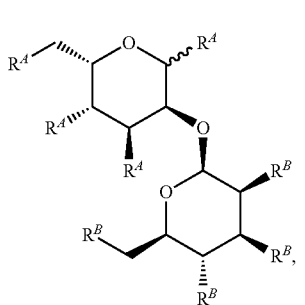
(Iaaa)
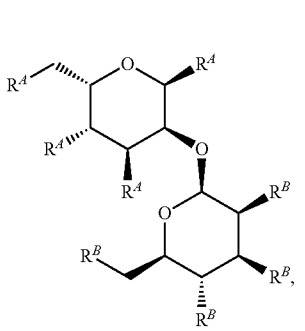
(Ibbb)

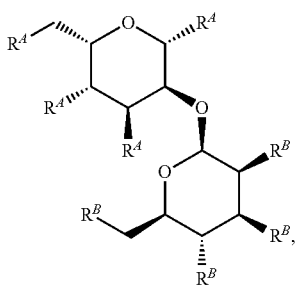
(Iccc)

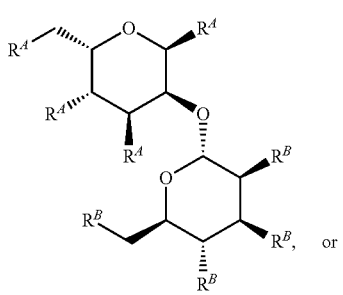
(Iddd)

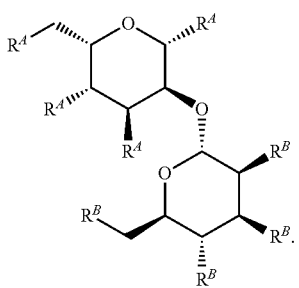
(Ieee)

$R^A$ and $R^B$ are Selected from One of the Following Groups (a)-(h):

(a) each $R^A$—$OR^1$ and each $R^B$ is —$OR^2$.

(b) one $R^A$ group is —N(H)($R^1$); each of the remaining $R^A$ groups is —$OR^1$; and each $R^B$ is —$OR^2$.

(c) one $R^A$ group is —N(H)($R^1$); each of the remaining $R^A$ groups is —$OR^1$; and each $R^B$ is —$OR^2$.

(d) one $R^B$ group is —N(H)($R^2$); each of the remaining $R^B$ groups is —$OR^2$; and each $R^A$ is —$OR^1$.

(e) one $R^A$ group is hydrogen; each of the remaining $R^A$ groups is —$OR^1$; and each $R^B$ is —$OR^2$.

(f) one $R^B$ group is hydrogen; each of the remaining $R^B$ groups is —$OR^2$; and each $R^A$ is —$OR^1$.

(g) Any one of groups (a)-(f), wherein one $R^1$ is $R^3$.

(h) Any one of groups (a)-(f), wherein one $R^2$ is $R^3$.

In embodiment (2) of the first aspect, the present disclosure provides disaccharide compounds according to formula (II),

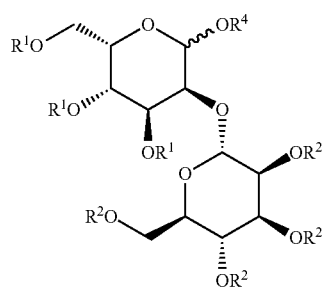
(II)

an epimer thereof, or a pharmaceutically acceptable salt thereof, wherein $R^1$, $R^2$, and $R^4$ are as defined for formula (I).

The invention further comprises preferred subgenera of embodiment (2) in which the substituents are selected as any and all combinations of structural formula (II), $R^1$-$R^4$, L, and $R^{40}$ as defined herein, including without limitation, the following:

Structural Formula II is One of Formulae (IIa)-(IIbb):

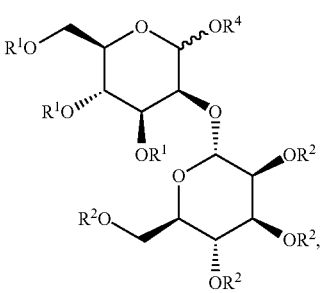
(IIa)

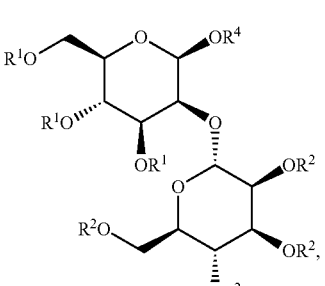
(IIb)

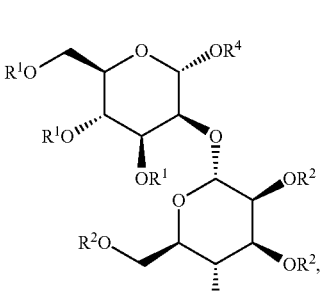
(IIc)

-continued
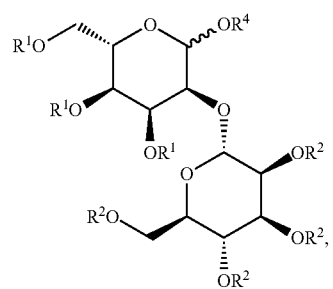
(IId)
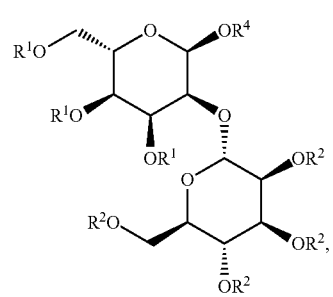
(IIe)
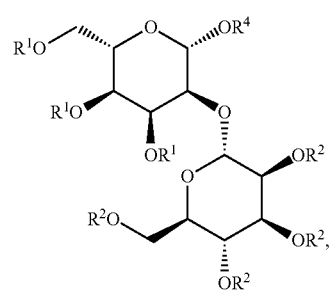
(IIf)
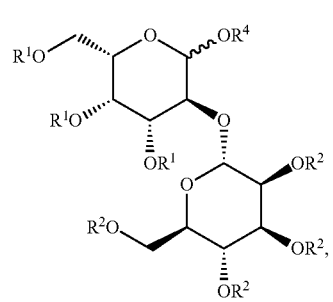
(IIg)
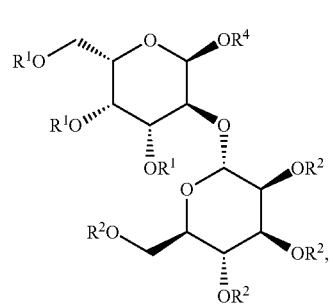
(IIh)
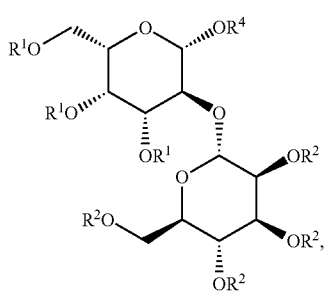
(IIi)
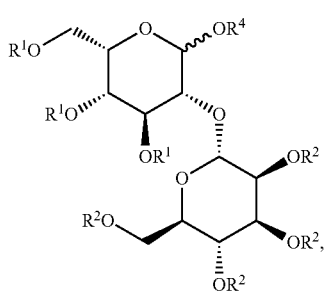
(IIj)
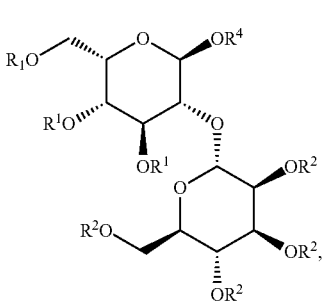
(IIk)
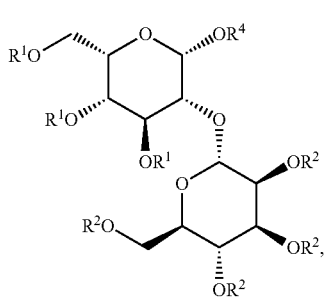
(IIl)
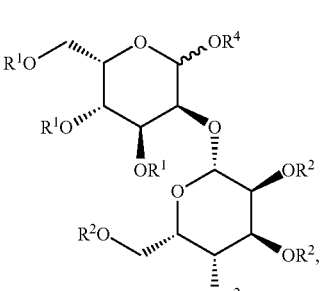
(IIm)

-continued
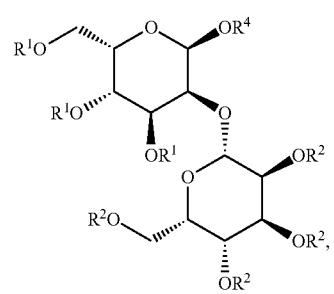
(IIn)
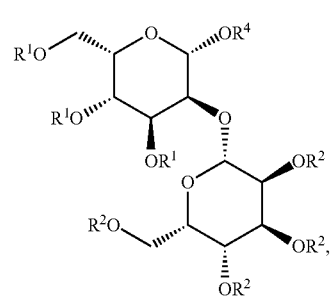
(IIo)
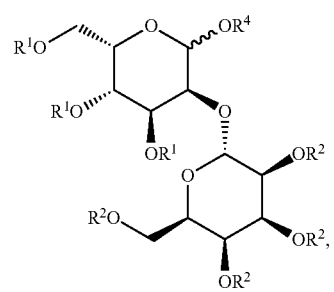
(IIp)
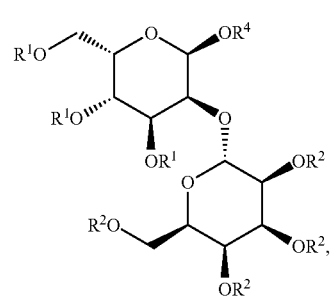
(IIq)
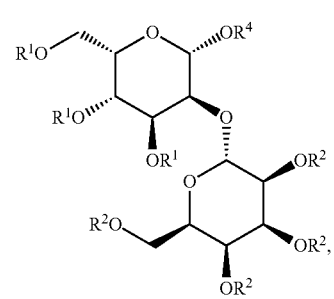
(IIr)
-continued
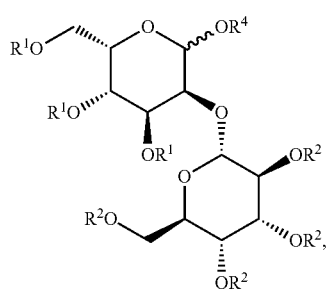
(IIr)
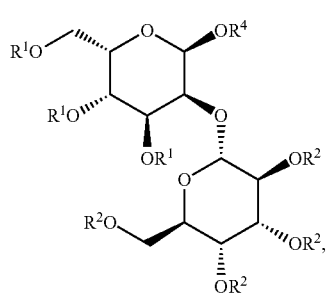
(IIs)
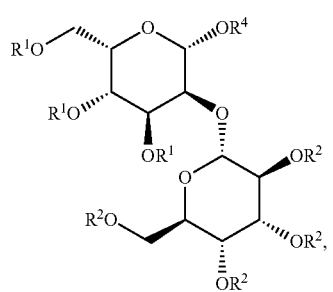
(IIt)
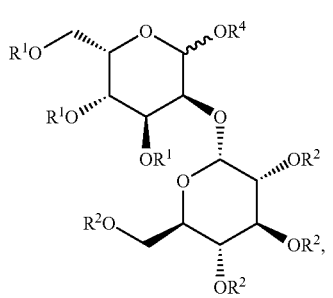
(IIu)
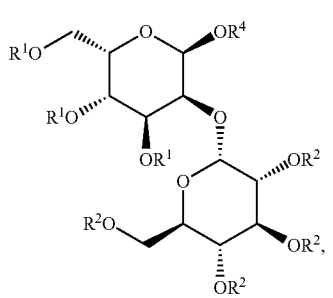
(IIv)

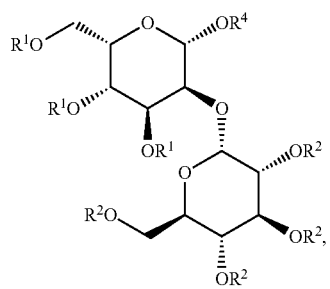
(IIw)

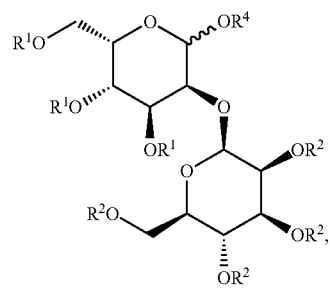
(IIx)

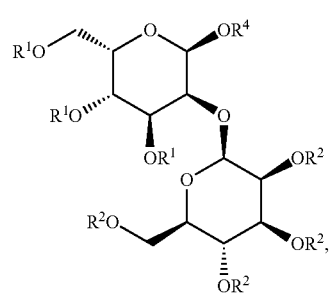
(IIy)

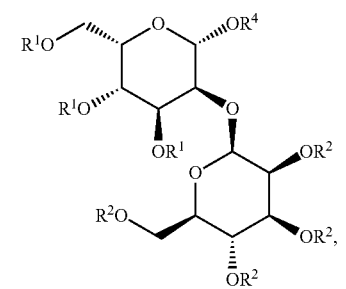
(IIz)

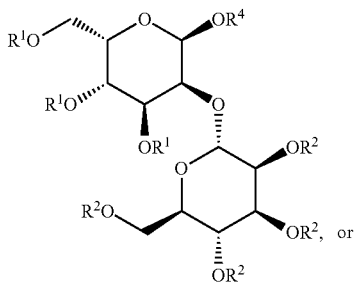
(IIaa)

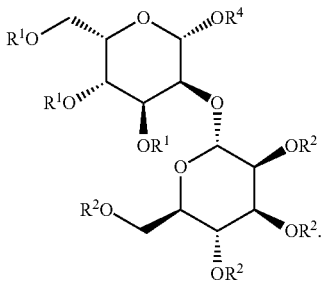
(IIbb)

$R^1$ and $R^2$ are Selected from One of the Following Groups (2a)-(2i):

(2a) each $R^1$ and $R^2$ is independently a protecting group.

(2b) each $R^1$ is a protecting group, one $R^2$ is $R^3$ and the remaining $R^2$ are each independently a protecting group.

(2c) Group (2a) or (2b), wherein each protecting group is independently —C(O)$R^{40}$ or benzyl, wherein $R^{40}$ is $C_1$-$C_6$ alkyl, halomethyl, dihalomethyl, trihalomethyl, or $C_1$-$C_4$alkoxymethyl.

(2d) Group (2a) or (2b), wherein each protecting group is independently —C(O)$R^{40}$ or benzyl, wherein $R^{40}$ is $C_1$-$C_6$ alkyl.

(2e) Group (2a) or (2b), wherein each protecting group is independently acetyl or benzyl.

(2f) Group (2a) or (2b), wherein each $R^1$ is benzyl and each $R^2$ is acetyl.

(2 g) Group (2a) or (2b), each $R^1$ is acetyl and each $R^2$ is benzyl.

(2h) each $R^1$ and $R^2$ is hydrogen.

(2i) each $R^1$ is hydrogen, one $R^2$ is $R^3$ and the remaining $R^2$ are each hydrogen.

$R^3$ is Selected from One of the Following Groups (3a)-(3g):

(3a) —C(O)O$R^{30}$, —C(O)N(H)($R^{30}$), —S(O)$_2$O$R^{30}$, —S(O)$_2$N(H)($R^{30}$), or —P(O)(O$R^{30}$)$_2$.

(3b) —C(O)N(H)($R^{30}$) or —S(O)$_2$N(H)($R^{30}$).

(3c) —C(O)O$R^{30}$ or —C(O)N(H)($R^{30}$).

(3d) —C(O)N(H)($R^{30}$).

(3e) Any one of groups (3a)-(3d) wherein $R^{30}$ is hydrogen or $C_1$-$C_6$ alkyl.

(3f) Any one of groups (3a)-(3d) wherein $R^{30}$ is hydrogen.

(3 g) —C(O)NH$_2$.

L is Selected from One of the Following Groups (4a)-(4j):

(4a) L is a bond, —$C_1$-$C_{20}$ alkyl-, —$C_2$-$C_{20}$ alkenyl-, —$C_2$-$C_{20}$ alkynyl-, -aryl-, -heteroaryl-, -heterocyclyl-, —$C_3$-$C_8$ cycloalkyl, -an oligoalkylene glycol, an oligopeptide, or a dendrimer.

(4b) L is -($L^1$-Y)$_n$-$L^2$-X—, wherein Y is —O—, —S—, or —N($R^Y$)—, wherein $R^Y$ is hydrogen or $C_1$-$C_6$ alkyl; n is an integer selected from 1 to 250; $L^1$ is —$C_2$-$C_6$ alkyl-; $L^2$ is —$C_1$-$C_{20}$ alkyl-, —$C_2$-$C_{20}$ alkenyl-, —$C_2$-$C_{20}$ alkynyl-, -aryl-, -heteroaryl-, -heterocyclyl-, —$C_3$-$C_8$ cycloalkyl-; and X is a bond, —O—, —N($R^X$), —S—, —C(O)—, —S(O)—, —S(O)$_2$—, —OC(O)—, —N($R^X$)C(O)—, —N($R^X$)S(O)—, —N($R^X$)S(O)$_2$—, —C(O)O—, —C(O)N($R^X$)—, —S(O)N($R^X$)—, —S(O)$_2$N($R^X$)—, —OC(O)O—, —OC(O)N($R^X$)—, —N($R^X$)C(O)O—, —N($R^X$)C(O)N($R^X$)—, or —N($R^X$)S(O)$_2$N($R^X$)—, wherein each $R^X$ is independently hydrogen or $C_1$-$C_6$ alkyl, and q is 1.

(4c) L is -($L^1$-O)$_n$-$L^2$-X—, wherein n is an integer selected from 1 to 250; $L^1$ is —$C_2$-$C_6$ alkyl-; $L^2$ is —$C_1$-$C_{20}$ alkyl-, —$C_2$-$C_{20}$ alkenyl-, —$C_2$-$C_{20}$ alkynyl-, -aryl-, -heteroaryl-, -heterocyclyl-, —$C_3$-$C_8$ cycloalkyl-; and X is a bond, —O—, —N(R$^X$)—, —S—, —C(O)—, —S(O)—, —S(O)$_2$—, —OC(O)—, —N(R$^X$)C(O)—, —N(R$^X$)S(O)—, —N(R$^X$)S(O)$_2$—, —C(O)O—, —C(O)N(R$^X$)—, —S(O)N(R$^X$)—, —S(O)$_2$N(R$^X$)—, —OC(O)O—, —OC(O)N(R$^X$)—, —N(R$^X$)C(O)O—, —N(R$^X$)C(O)N(R$^X$)—, or —N(R$^X$)S(O)$_2$N(R$^X$)—, wherein each R$^X$ is independently hydrogen or C$_1$-C$_6$ alkyl, and q is 1.

(4d) L is -(L$^1$-O)$_n$-L$^2$-X—, herein L$^1$ is —C$_2$-C$_4$ alkyl-; L$^2$ is —C$_1$-C$_6$ alkyl-; and X is a bond, —O—, —N(R$^X$), —S—, —C(O)—, —S(O)—, or —S(O)$_2$—.

(4e) L is —(CH$_2$CH$_2$—O)$_n$—CH$_2$CH$_2$—X—, wherein X is —O—, —N(H), or —S—.

(4f) L is —(CH$_2$CH$_2$—O)$_n$—CH$_2$CH$_2$—X—, wherein X is —C(O)— or —S(O)$_2$—.

(4g) Any one of groups (4b)-(4f), wherein n is an integer selected from 1 to 20.

(4h) Any one of groups (4b)-(4f), wherein n is an integer selected from 1 to 10.

(4i) Any one of groups (4b)-(4f), wherein n is an integer selected from 1 to 5.

(4j) Any one of groups (4b)-(4f), wherein n is an integer selected from 1 to 3.

R$^{40}$ is Selected from One of the Following Groups (5a)-(5j):

(5a) —R$^{41}$.
(5b) —OH, —NH$_2$, —SH, or —C(O)OH.
(5c) an imaging agent.
(5d) a fluorescent imaging agent (e.g., fluorescein).
(5e) an imaging agent comprises a chelating group coordinated to a radioactive imaging moiety.
(5f) a member of a specific binding pair.
(5g) a member of a specific binding pair, selected from the following specific binding pairs: biotin-streptavidin, biotin-avidin, metal/chelator binding pairs; protein/protein binding pairs; protein-cofactors binding pairs; (modified) nucleic acid-nucleic acid binding pairs; and protein/nucleic acid binding pairs
(5h) a member of a specific binding pair, selected from biotin-streptavidin and biotin-avidin,
(5i) biotin.
(5j) a chemotherapeutic agent.

R$^4$ is Selected from One of the Following Groups (6a)-(6v):

(6a) -L-R$^{40}$.
(6b) -L-R$^{40}$ wherein L is according to any one of groups (4a)-(4j), and R$^{40}$ is R$^{41}$.
(6c) -L-R$^{40}$ wherein L is according to any one of groups (4a)-(4j), and R$^{40}$ is a fluorescent imaging agent.
(6d) -L-R$^{40}$ wherein L is according to any one of groups (4a)-(4j), and R$^{40}$ is an imaging agent comprising a chelating group coordinated to a radioactive imaging moiety.
(6e) -L-R$^{40}$ wherein L is according to any one of groups (4a)-(4j), and R$^{40}$ a member of a specific binding pair.
(6f) -L-R$^{40}$ wherein L is according to any one of groups (4a)-(4j), and R$^{40}$ is a chemotherapeutic agent.
(6 g) -L-R$^{40}$ wherein L is -(L$^1$-O)$_n$-L$^2$-X—, wherein n is an integer selected from 1 to 20; L$^1$ is —C$_2$-C$_4$ alkyl-; L$^2$ is —C$_1$-C$_6$ alkyl-; X is a bond, and R$^{40}$ is R$^{41}$.
(6h) -L-R$^{40}$ wherein L is —(CH$_2$CH$_2$—O)$_n$—CH$_2$CH$_2$—X—, wherein n is an integer selected from 1 to 20; X is a bond, and R$^{40}$ is R$^{41}$.
(6i) Group (6g) or (6h), wherein R$^{40}$ is —OH, —NH$_2$, —SH, or —C(O)OH.
(6j) -L-R$^{40}$ wherein L is -(L$^1$-O)$_n$-L$^2$-X—, wherein n is an integer selected from 1 to 20; L$^1$ is —C$_2$-C$_4$ alkyl-; L$^2$ is —C$_1$-C$_6$ alkyl-; X is a bond, —C(O)—, —S(O)$_2$—, —O—, —N(H), or —S—; and R$^{40}$ is a fluorescent imaging agent.
(6k) -L-R$^{40}$ wherein L is —(CH$_2$CH$_2$—O)$_n$—CH$_2$CH$_2$—X—, wherein n is an integer selected from 1 to 20; X is a bond, —C(O)—, —S(O)$_2$—, —O—, —N(H), or —S—, and R$^{40}$ is a fluorescent imaging agent.
(6l) -L-R$^{40}$ wherein L is -(L$^1$-O)$_n$-L$^2$-X—, wherein n is an integer selected from 1 to 20; L$^1$ is —C$_2$-C$_4$ alkyl-; L$^2$ is —C$_1$-C$_6$ alkyl-; X is a bond, —C(O)—, —S(O)$_2$—, —O—, —N(H), or —S—, and R$^{40}$ is an imaging agent comprises a chelating group coordinated to a radioactive imaging moiety.
(6m) -L-R$^{40}$ wherein L is —(CH$_2$CH$_2$—O)$_n$—CH$_2$CH$_2$—X—, wherein n is an integer selected from 1 to 20; X is a bond, —C(O)—, —S(O)$_2$—, —O—, —N(H), or —S—, and R$^{40}$ is an imaging agent comprises a chelating group coordinated to a radioactive imaging moiety.
(6n) -L-R$^{40}$ wherein L is -(L$^1$-O)$_n$-L$^2$-X—, wherein n is an integer selected from 1 to 20; L$^1$ is —C$_2$-C$_4$ alkyl-; L$^2$ is —C$_1$-C$_6$ alkyl-; X is a bond, —C(O)—, —S(O)$_2$—, —O—, —N(H), or —S—, and R$^{40}$ a member of a specific binding pair.
(6o) -L-R$^{40}$ wherein L is —(CH$_2$CH$_2$—O)$_n$—CH$_2$CH$_2$—X—, wherein n is an integer selected from 1 to 20; X is a bond, —C(O)—, —S(O)$_2$—, —O—, —N(H), or —S—, and R$^{40}$ a member of a specific binding pair.
(6p) Any one of groups (6e), (6n), or (6o), wherein R$^{40}$ a member of a specific binding pair, selected from biotin-streptavidin, biotin-avidin, metal/chelator binding pairs; protein/protein binding pairs; protein-cofactors binding pairs; (modified) nucleic acid-nucleic acid binding pairs; and protein/nucleic acid binding pairs.
(6q) Group (6p) wherein R$^{40}$ is biotin.
(6r) -L-R$^{40}$ wherein L is -(L$^1$-O)$_n$-L$^2$-X—, wherein n is an integer selected from 1 to 20; L$^1$ is —C$_2$-C$_4$ alkyl-; L$^2$ is —C$_1$-C$_6$ alkyl-; X is a bond, —C(O)—, —S(O)$_2$—, —O—, —N(H), or —S—, and R$^{40}$ is a chemotherapeutic agent.
(6s) -L-R$^{40}$ wherein L is —(CH$_2$CH$_2$—O)$_n$—CH$_2$CH$_2$—X—, wherein n is an integer selected from 1 to 20; X is a bond, —C(O)—, —S(O)$_2$—, —O—, —N(H), or —S—, and R$^{40}$ is a chemotherapeutic agent.
(6t) Any one of Groups (6g)-(6s), wherein n is an integer selected from 1 to 10.
(6u) Any one of Groups (6g)-(6s), wherein n is an integer selected from 1 to 5.
(6v) Any one of Groups (6g)-(6s), wherein n is an integer selected from 1 to 3.

In preferred embodiment (3) of the first aspect, the compound of formula (I) is according to the formula, (III)

an epimer thereof, or a pharmaceutically acceptable salt thereof, wherein
each R$^1$ and R$^2$ is independently hydrogen or a protecting group;

$R^3$ is —C(O)O$R^{30}$ or —C(O)N(H)($R^{30}$), wherein $R^{30}$ is hydrogen or $C_1$-$C_6$ alkyl; and $R^4$ is independently -L-$R^{40}$, wherein L is a bond or a linker; and $R^{40}$ is independently an imaging agent, a member of a specific binding pair, or a chemotherapeutic agent.

The invention further comprises preferred subgenera of embodiment (3) of the first aspect in which the substituents are selected as any and all combinations of structural formula (III), $R^1$-$R^4$, L, and $R^{40}$ as defined herein, including without limitation, the following:

(a) structural formula (III) is one of formulae (IIIa) and (IIIb):

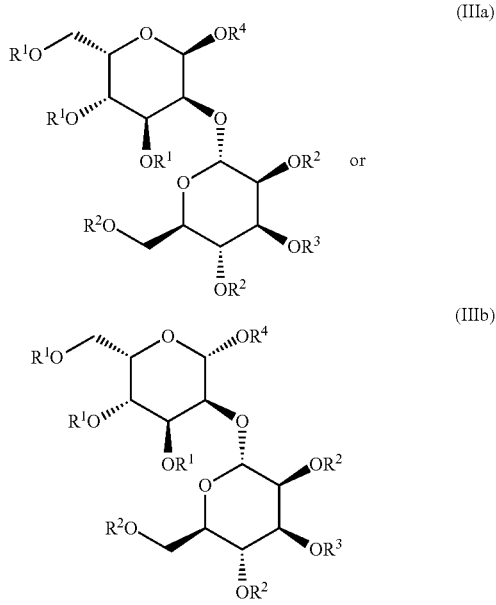

(b) $R^1$ and $R^2$ are selected from one of groups (2a)-(2i) as described above.

(C) $R^3$ is groups (3d) or (3g) as described above.

(d) L is selected from one of groups (4b)-(4j) as described above.

(e) $R^{40}$ is selected from one of groups (5c)-(5j) as described above.

(f) $R^4$ is selected from one of the following groups (6g)-(6v) as described above.

In any of the preceding embodiments of the first aspect, when $R^{40}$ is an imaging agent, a member of a specific binding pair, or a chemotherapeutic agent, then $R^{40}$ can be attached to L or directly to the core disaccharide (when L is a bond) via any available functional group on the $R^{40}$ moiety. For example, when $R^{40}$ is biotin, then the biotin can be bonded to L or the core disaccharide via the carboxylic acid group therein, or an activated form thereof (e.g., an N-hydroxysuccinimidyl ester) through formation, for example, of an ester or amide linkage (i.e., X is —O— or —N($R^X$)—, respectively).

In certain examples, a chemical linkage can be formed between L and the $R^{40}$ moiety to form a moiety of the form, —X—$R^{45}$, where X is as defined previously and $R^{45}$ is the remainder of the imaging agent, member of a specific binding pair, or the chemotherapeutic agent (i.e., a residue thereof). For example, —X—$R^{45}$ includes, but is not limited to groups of the form, —O$R^{45}$, —NH($R^{45}$), —S$R^{45}$, —OC(O)$R^{45}$, —C(O)O$R^{45}$, —C(O)NH($R^{45}$), —OC(O)O$R^{45}$, —OC(O)N(H)($R^{45}$), —N($R^{45}$)C(O)O$R^{45}$, —N($R^{45}$)C(O)N(H)($R^{45}$), —S(O)N(H)($R^{45}$), or —S(O)$_2$N(H)($R^{45}$).

When L is a bond, then a chemical linkage can be formed between the core disaccharide (when L is a bond) and the $R^{40}$ moiety to form a moiety of the form, —O$R^{45}$, —OC(O)$R^{45}$, —OC(O)O$R^{45}$, or —OC(O)N(H)($R^{45}$), where $R^{45}$ is the remainder of the imaging agent, member of a specific binding pair, or the chemotherapeutic agent (i.e., a residue thereof).

The present invention is not limited by type of chemotherapeutic agent used (e.g., $R^{40}$ in the instant compounds). A variety of chemotherapeutic agents are contemplated to be useful in the compounds including, but not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; 1-b eta-D-arabinofuranosylcytosine ("AraC"); asparaginase; asperlin; azacitidine; azetepa; azotomycin; batimastat; benzodepa; bicalutamide; bisantrene hydrochloride; bisnafide dimesylate; bizelesin; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; 5-fluorouracil; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nitrosurea; nocodazole; nogalamycin; ormaplatin; oxisuran; paclitaxel; pegaspargase; peliomycin; pentamustine; peplomycin sulfate; perfosfamide; N-phosphonoacetyl-L-aspartate ("PALA"); pipobroman; piposulfan; piroxantrone hydrochloride; plicamycin; plomestane; podophyllotoxin; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; taxol; tecogalan sodium; tegafur; teloxantrone hydrochloride; temoporfin; teniposide; teroxirone; testolactone; thiamiprine; thioguanine; thiotepa; tiazofurin; tirapazamine; topotecan; toremifene citrate; transplatinum; trestolone acetate; triciribine phosphate; trimetrexate; trimetrexate glucuronate; triptorelin; tubulozole hydrochloride; uracil mustard; uredepa; vapreotide; verapamil, verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In some embodiments, the chemotherapeutic agent comprises an antisense nucleic acid (e.g., RNA, molecule). In certain embodiments, the antisense nucleic acid comprises a sequence complementary to an RNA of an oncogene. The oncogene can include, but is not limited to, abl, Bcl-2, Bcl-xL, erb, fms, gsp, hst, jun, myc, neu, raf; ras, ret, src, or trk. Suitable nucleic acid encoding a therapeutic protein encodes a factor include, but not limited to, a tumor suppressor, cytokine, receptor, inducer of apoptosis, or differentiating agent. Tumor suppressors include, but are not limited to, BRCA1, BRCA2, C-CAM, p16, p21, p53, p73, Rb, and p27. Cytokines include, but are not limited to, GMCSF, IL-1, IL-2, IL-3, IL-4, IL-5, IL-6, IL-7, IL-8, IL-9, IL-10, IL-11, IL-12, IL-13, IL-14, IL-15, .beta.-interferon, .gamma.-interferon, and TNF. Receptors include, but are not limited to, CFTR, EGFR, estrogen receptor, IL-2 receptor, and VEGFR. Suitable inducers of apoptosis include, but are not limited to, AdElB, Bad, Bak, Bax, Bid, Bik, Bim, Harakid, and ICE-CED3 protease.

Further chemotherapeutic agents include but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin and camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytotoxic factor; cytostatin; daclixinab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O(6)-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegaftir; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vincristine; vinxaltine; vitaxin; vorozole; zanoterone; zeniplatin; zilascorb; zinostatin stimalamer; 5-fluorouracil; and leucovorin.

In certain embodiments, chemotherapeutic agents (i.e., $R^{40}$) include agents such as, but not limited to, cisplatin, carboplatin, spiroplatin, iproplatin, paclitaxel, docetaxel, rapamycin, tacrolimus, asparaginase, etoposide, teniposide, tamoxifen, amsacrine, mitotane, topotecan, tretinoin, hydroxyurea, procarbazine, BCNU (carmustine) and other nitrosourea compounds, as well as others classified as alkylating agents (e.g., mechlorethamine hydrochloride, cyclophosphamide, ifosfamide, chlorambucil, melphalan, busulfan, thiotepa, carmustine, estramustine, dacarbazine, omustine, streptozocin), plant alkaloids (e.g., vincristine, vinblastine, vinorelbine, vindesine), antimetabolites (e.g., folic acid analogs, methotrexate, fludarabine), pyrimidine analogs (fluorouracil, fluorodeoxyuridine, cytosine arabinoside, cytarabine, azidothymidine, cysteine arabinoside, and azacytidine), purine analogs (mercaptopurine, thioguanine, cladribine, pentostatin, arabinosyl adenine), antitumor antibiotics (e.g., adriamycin, dactinomycin, daunorubicin, doxorubicin, amsacrine, idarubicin, mitoxantrone, plicamycin, ansamitomycin, mitomycin), aminoglutethimide (an aromatase inhibitor), flutamide (an anti-androgen), gemtuzumab ozogamicin (a monoclonal antibody), and oprelvekin (a synthetic interleukin), as well as cell cycle inhibitors and EGF receptor kinase inhibitors in general.

In other embodiments, $R^{40}$ is an imaging agent. Examples of imaging agents include, but are not limited to a radioactive imaging agent, a fluorescent imaging agent, or a magnetic resonance imaging (MRI) contrast imaging agent.

In certain embodiments, the radioactive imaging agent comprises a chelating group and a radioactive imaging moiety.

The chelating group can be selected from 1,4,7,10-tetraazacyclododecane-1,4,7,10-tetraacetic acid (DOTA), diethylenetriaminepentaacetic acid bis(methylamide) (DTPA-BMA), N,N'-bis(2-pyridylmethyl)diethylenetriamine-N,N',N"-triacetic acid (DTPA-BP), and trans-1,2-diaminocyclohexane-N,N',N",N"'-tetraacetic acid (CDTA). In certain embodiments, the chelating group is DOTA.

Examples of radioactive imaging moieties include, but are not limited to, $^{225}Ac$, $^{227}Ac$, $^{241}Am$, $^{72}As$, $^{74}As$, $^{211}At$, $^{198}Au$, $^{7}Be$, $^{212}Bi$, $^{213}Bi$, $^{75}Br$, $^{77}Br$, $^{11}C$, $^{14}C$, $^{48}Ca$, $^{109}Cd$, $^{139}Ce$, $^{141}Ce$, $^{252}Cf$, $^{36}Cl$, $^{55}Co$, $^{57}CO$, $^{58}Co$, $^{60}Co$, $^{51}Cr$, $^{130}Cs$, $^{131}Cs$, $^{137}Cs$, $^{61}Cu$, $^{62}Cu$, $^{165}Dy$, $^{152}Eu$, $^{155}Eu$, $^{18}F$, $^{59}Fe$, $^{64}Ga$, $^{67}Ga$, $^{68}Ga$, $^{153}Gd$, $^{68}Ge$, $^{3}H$, $^{122}I$, $^{123}I$, $^{124}I$, $^{125}I$, $^{131}I$, $^{132}I$, $^{111}In$, $^{115m}In$, $^{191m}Ir$, $^{192}Ir$, $^{81m}Kr$, $^{111}Ln$, $^{177}Lu$, $^{51}Mn$, $^{52}Mn$, $^{99}Mo$, $^{13}N$, $^{95}Nb$, $^{15}O$, $^{191}Os$, $^{194}Os$, $^{32}P$, $^{33}P$, $^{203}Pb$, $^{212}Pb$, $^{103}Pd$, $^{109}Pd$, $^{238}Pu$, $^{223}Ra$, $^{226}Ra$, $^{82}Rb$, $^{186}Re$, $^{188}Re$, $^{105}Rh$, $^{97}Ru$, $^{103}Ru$, $^{35}S$, $^{72}Se$, $^{75}Se$, $^{28}Si$, $^{145}Sm$, $^{153}Sm$, $^{117m}Sn$, $^{85}Sr$, $^{89}Sr$, $^{90}Sr$, $^{178}Ta$, $^{179}Ta$, $^{182}Ta$, $^{149}Tb$, $^{96}Tc$, $^{99m}Tc$, $^{228}Th$, $^{229}Th$, $^{201}Tl$, $^{170}Tm$, $^{171}Tm$, $^{188}W$, $^{127}Xe$, $^{88}Y$, $^{90}Y$, $^{91}Y$, $^{169}Yb$, $^{175}Yb$, $^{62}Zn$, $^{65}Zn$, $^{95}Zr$, and $^{99m}Tc$-labeled Annexin $V^{28}$. In certain embodiments, the radioactive moiety is capable of being chelated by a chelating agent and is selected from $^{225}Ac$, $^{227}Ac$, $^{241}Am$, $^{198}Au$, $^{7}Be$, $^{212}Bi$, $^{213}Bi$, $^{48}Ca$, $^{109}Cd$, $^{139}Ce$, $^{141}Ce$, $^{252}Cf$, $^{36}Cl$, $^{55}Co$, $^{57}Co$, $^{58}Co$, $^{60}Co$, $^{51}Cr$, $^{130}Cs$, $^{131}Cs$, $^{137}Cs$, $^{61}Cu$, $^{62}Cu$, $^{165}Dy$, $^{152}Eu$, $^{155}Eu$, $^{18}F$, $^{55}Fe$, $^{59}Fe$, $^{64}Ga$, $^{67}Ga$, $^{68}Ga$, $^{153}Gd$, $^{68}Ge$, $^{111}In$, $^{115m}In$, $^{191m}Ir$, $^{192}Ir$, $^{111}Ln$, $^{177}Lu$, $^{51}Mn$, $^{52}Mn$, $^{99}Mo$, $^{95}Nb$, $^{194}Os$, $^{203}Pb$, $^{212}Pb$, $^{103}Pd$, $^{109}Pd$, $^{238}Pu$, $^{223}Ra$, $^{226}Ra$, $^{82}Rb$, $^{186}Re$, $^{88}Re$, $^{105}Rh$, $^{97}Ru$, $^{103}Ru$, $^{145}Sm$, $^{153}Sm$, $^{117m}Sn$, $^{85}Sr$, $^{89}Sr$, $^{90}Sr$, $^{178}Ta$, $^{179}Ta$, $^{182}Ta$, $^{149}Tb$, $^{96}Tc$, $^{99m}Tc$, $^{228}Th$, $^{229}Th$, $^{201}Tl$, $^{170}Tm$, $^{171}Tm$, $^{188}W$, $^{88}Y$, $^{90}Y$, $^{91}Y$, $^{169}Yb$, $^{175}Yb$, $^{62}Zn$, $^{65}Zn$, $^{99m}Tc$-labeled Annexin $V^{28}$, and $^{95}Zr$.

In other embodiments, $R^{40}$ is a magnetic resonance imaging (MRI) contrast imaging agent. Examples of such contrast agents, include, but are not limited to, gadopentetate dimeglumine, gadoteridol, gadoterate meglumine, mangafodipir trisodium, gadodiamide, gadoversetamide, and superparamagnetic iron oxide.

In certain embodiments, the MRI contrast imaging agent is superparamagnetic iron oxide (SPIO). Superparamagnetic iron oxide (SPIO) nanoparticles are a class of MRI contrast agents that provide extremely strong enhancement of proton relaxation, and are generally composed of iron oxide nanocrystals which create a large, dipolar magnetic field gradient that creates a relaxation effect on nearby water molecules. According to their sizes and applications, SPIO nanoparticles have been classified into four different categories: large, standard, ultrasmall, and monocrystalline agents. Large SPIO agents are mainly used for gastrointestinal lumen imaging, while standard SPIO agents are used for liver and spleen imaging. When the SPIO nanoparticles are in the range of 20-$^{40}$ nm (ultrasmall category), they can be injected to visualize lymph node metastases. The smallest monocrystalline SPIO agents can be used for tumor-specific imaging.

In another embodiment, the imaging agents can comprise a fluorescent imaging agent. A fluorescent imaging agent is any chemical moiety that has a detectable fluorescence signal. This imaging agent can be used alone or in combination with other imaging agents. Examples of suitable fluorescent agents that can be used in the compositions and methods disclosed herein include, but are not limited to, fluorescein (FITC), 5-carboxyfluorescein-N-hydroxysuccinimide ester, 5,6-carboxymethyl fluorescein, nitrobenz-2-oxa-1,3-diazol-4-yl (NBD), fluorescamine, OPA, NDA, indocyanine green dye, the cyanine dyes (e.g., Cy3, Cy3.5, Cy5, Cy5.5 and Cy7), 4-acetamido-4'-isothiocyanatostilbene-2,2' disulfonic acid, acridine, acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate, N-(4-anilino-1-naphthyl)maleimide, anthranilamide, BODIPY, Brilliant Yellow, coumarin, 7-amino-4-methylcoumarin (AMC, Coumarin 120), 7-amino-4-trifluoromethylcoumarin (Coumaran 151), cyanosine, 4',6-diaminidino-2-phenylindole (DAPI), 5',5"-dibromopyrogallol-sulfonaphthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino] naphthalene-1-sulfonyl chloride (DNS, dansylchloride), 4-(4'-dimethylaminophenylazo)benzoic acid (DABCYL), 4-dimethylaminophenylazophenyl-4'-isothiocyanate (DABITC), eosin, eosin isothiocyanate, erythrosin B, erythrosine, isothiocyanate, ethidium bromide, ethidium, 5-carboxyfluorescein (FAM), 5-(4,6-dichlorotriazin-2-yl)amino-fluorescein (DTAF), 2',7'-dimethoxy-4'5'-dichloro-6-carboxyfluorescein (JOE), fluorescein isothiocyanate, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron[R] Brilliant Red 3B-A), 6-carboxy-X-rhodamine (ROX), 6-carboxyrhodamine (R6G), lissamine rhodamine B sulfonyl chloride rhodamine (Rhod), 5,6-tetramethyl rhodamine, rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (6-TAMRA), tetramethyl rhodamine, tetramethyl rhodamine isothiocyanate (TRITC), riboflavin, rosolic acid, coumarin-6, and the like, including combinations thereof. These fluorescent imaging moieties can be obtained from a variety of commercial sources, including Molecular Probes, Eugene, Oreg. and Research Organics, Cleveland, Ohio, or can be synthesized by those of ordinary skill in the art. In an embodiment, the imaging agent is fluorescein or 6-TAMRA.

In embodiment (1) of the second aspect, the present disclosure provides intermediate compounds for the preparation of compounds of formulae (I)-(III), including compounds of formula (IV),

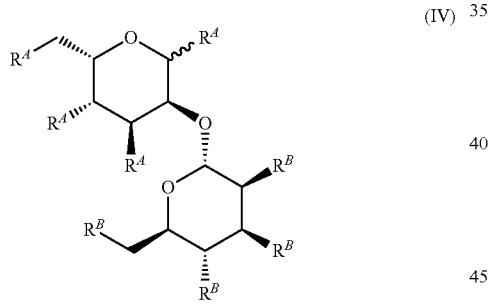

(IV)

or an epimer thereof, wherein
each $R^A$ is independently hydrogen, —$OR^1$, or —$N(H)(R^1)$, wherein
  each $R^1$ is independently hydrogen, a protecting group, —$R^3$, or —$R^6$, wherein
    $R^3$ is —$C(O)OR^{30}$, —$C(O)N(H)(R^{30})$, —$S(O)OR^{30}$, —$S(O)_2OR^{30}$, —$S(O)N(H)(R^{30})$, —$S(O)_2N(H)(R^{30})$, or —$P(O)(OR^{30})_2$, wherein
      $R^{30}$ is hydrogen, $C_1$-$C_6$ alkyl, $C_1$-$C_6$ haloalkyl, aryl, heteroaryl, $C_3$-$C_8$ cycloalkyl, or heterocyclyl, wherein $R^{30}$ is optionally substituted with one to four groups which are each independently $C_1$-$C_6$ alkyl, cyano, nitro, halogen, —$OR^{31}$, —$N(R^{31})_2$, —$SR^{31}$, —$C(O)R^{31}$, —$C(O)OR^{31}$, —$C(O)N(R^{31})_2$, —$OC(O)OR^{31}$, —$OC(O)N(R^{31})_2$, —$N(R^{31})C(O)OR^{31}$, —$N(R^{31})C(O)N(R^{31})_2$, —$S(O)R^{31}$, —$S(O)_2R^{31}$, —$S(O)N(R^{31})_2$, or —$S(O)_2N(R^{31})_2$, wherein each $R^{31}$ is independently hydrogen or $C_1$-$C_6$ alkyl;
    $R^6$ is —$S(O)_2R^{10}$ or —$P(O)(OR^{10})_2$, wherein each $R^{10}$ is independently $C_1$-$C_6$ alkyl, $C_1$-$C_6$ haloalkyl, aryl, heteroaryl, $C_3$-$C_8$ cycloalkyl, or heterocyclyl, wherein the aryl, heteroaryl, $C_3$-$C_8$ cycloalkyl, and heterocyclyl are each optionally substituted with one to four groups which are each independently $C_1$-$C_6$ alkyl, cyano, nitro, halogen, —$OR^{11}$, —$N(R^{11})_2$, —$SR^{11}$, —$C(O)R^{11}$, —$C(O)OR^{11}$, —$C(O)N(R^{11})_2$, —$OC(O)OR^{11}$, —$OC(O)N(R^{11})_2$, —$N(R^{11})C(O)OR^{11}$, —$N(R^{11})C(O)N(R^{11})_2$, —$S(O)R^{11}$, —$S(O)_2R^{11}$, —$S(O)N(R^{11})_2$, or —$S(O)_2N(R^{11})_2$, wherein each $R_{11}$ is independently hydrogen or $C_1$-$C_6$ alkyl;
  or two $R^1$ groups taken together form a diol protecting group;
each $R^B$ is independently hydrogen, —$OR^2$, or —$N(H)(R^2)$, wherein each $R^2$ is independently hydrogen, a protecting group, —$R^3$, or —$R^6$, or two $R^2$ groups taken together form a diol protecting group;
provided that
  (i) no more than one $R^3$ group is present;
  (ii) no more than one $R^1$ is $R^6$, and no more than one $R^2$ is $R^6$; and
  (iii) no more than two $R^A$ groups are hydrogen, and no more than two $R^B$ groups are hydrogen.

The invention further comprises preferred subgenera of embodiment (1) of the second aspect in which the substituents are selected as any and all combinations of structural formula (IV), $R^A$ and $R^B$, including without limitation, the following:

Structural Formula IV is One of Formulae (IVa)-(IVb):

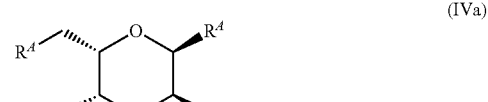

(IVa)

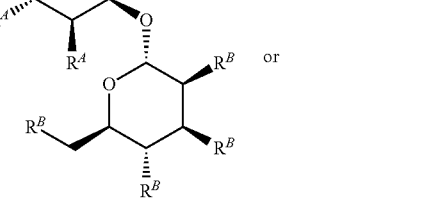

or

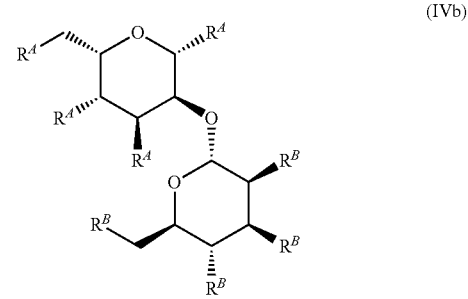

(IVb)

$R^A$ and $R^B$ are selected from one of the following groups (7a)-(7f):
(7a) each $R^A$ —$OR^1$ and each $R^B$ is —$OR^2$.
(7b) one $R^A$ group is —$N(H)(R^1)$; each of the remaining $R^A$ groups is —$OR^1$; and each $R^B$ is —$OR^2$.
(7c) one $R^A$ group is —$N(H)(R^1)$; each of the remaining $R^A$ groups is —$OR^1$; and each $R^B$ is —$OR^2$.
(7d) one $R^B$ group is —$N(H)(R^2)$; each of the remaining $R^B$ groups is —$OR^2$; and each $R^A$ is —$OR^1$.
(7e) one $R^A$ group is hydrogen; each of the remaining $R^A$ groups is —$OR^1$; and each $R^B$ is —$OR^2$.
(7f) one $R^B$ group is hydrogen; each of the remaining $R^B$ group is —$OR^2$; and each $R^A$ is —$OR^1$.

(7 g) Any one of groups (7a)-(7f), wherein one $R^1$ is $R^3$.
(7h) Any one of groups (7a)-(7f), wherein one $R^2$ is $R^3$.

In embodiment (2) of the second aspect, the present disclosure provides compounds of formula (V),

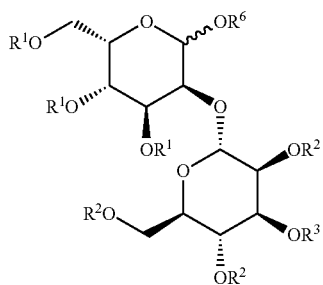

or an epimer there of, wherein $R^1$, $R^2$, $R^3$, and $R^6$ are as defined for formula IV.

The invention further comprises subgenera of embodiment (2) of the second aspect in which the substituents are selected as any and all combinations of structural formula (V), $R^1$, $R^2$, $R^3$, and $R^6$ including without limitation, the following:

Structural Formula V is One of Formulae (Va)-(Vb):

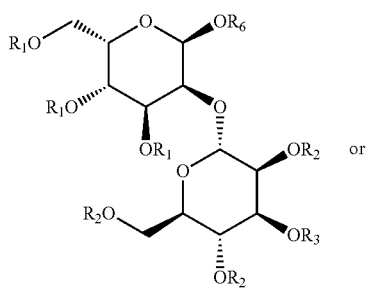

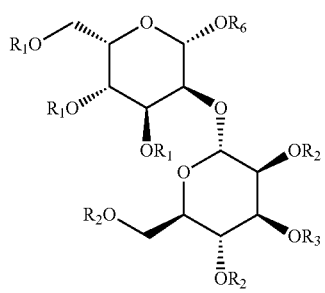

$R^1$ and $R^2$ are Selected from One of the Following Groups (8a)-(8o):
(8a) each $R^1$ and $R^2$ is independently a protecting group.
(8b) Group (8a), wherein each protecting group is independently —C(O)$R^{40}$ or benzyl, wherein $R^{40}$ is $C_1$-$C_6$ alkyl, halomethyl, dihalomethyl, trihalomethyl, or $C_1$-$C_4$alkoxymethyl.
(8c) Group (8a), wherein each protecting group is independently —C(O)$R^{40}$ or benzyl, wherein $R^{40}$ is $C_1$-$C_6$ alkyl.
(8d) Group (8a), wherein each protecting group is independently acetyl or benzyl.
(8e) each $R^1$ is benzyl and each $R^2$ is acetyl.
(8f) each $R^1$ is acetyl and each $R^2$ is benzyl.
(8g) each $R^1$ and $R^2$ is hydrogen.
(8h) each $R^1$ and $R^2$ is independently a protecting group, or two $R^1$ groups taken together form a diol protecting group, or two $R^2$ groups taken together form a diol protecting group.
(8i) Group (8h), wherein each protecting group is independently —C(O)$R^{40}$ or benzyl, wherein $R^{40}$ is $C_1$-$C_6$ alkyl, halomethyl, dihalomethyl, trihalomethyl, or $C_1$-$C_4$alkoxymethyl.
(8j) Group (8h), wherein each protecting group is independently —C(O)$R^{40}$ or benzyl, wherein $R^{40}$ is $C_1$-$C_6$ alkyl.
(8k) Group (8h), wherein each protecting group is independently acetyl or benzyl.
(8l) Any one of Groups (8h)-(8k), wherein each diol protecting group, when present, is independently —C(O)—, —C($R^7$)($R^8$)— or —Si($R^9$)$_2$—, wherein $R^7$ is hydrogen, $C_1$-$C_2$ alkyl, or phenyl; $R^8$ is hydrogen, $C_1$-$C_4$ alkyl, vinyl, trihalomethyl, phenyl, naphthyl, methoxyphenyl, or dimethoxyphenyl; or $R^7$ and $R^8$ taken together with the carbon to which they are both attached form a cyclopentyl or cyclohexyl group; and each $R^9$ is independently $C_1$-$C_6$ alkyl, benzyl, or phenyl.
(8m) Any one of Groups (8h)-(8k), wherein each diol protecting group, when present, is independently —C($R^7$)($R^8$)—, wherein $R^7$ is hydrogen or methyl; and $R^8$ is hydrogen, $C_1$-$C_4$ alkyl, vinyl, trihalomethyl, phenyl, naphthyl, methoxyphenyl, or dimethoxyphenyl.
(8n) Any one of Groups (8h)-(8k), wherein each diol protecting group, when present, is independently —C($R^7$)($R^8$)—, wherein $R^7$ is hydrogen or methyl; and $R^8$ is hydrogen, $C_1$-$C_4$ alkyl, or phenyl.
(8o) Any one of Groups (8h)-(8k), wherein each diol protecting group, when present, is independently —C($R^7$)($R^8$)—, wherein $R^7$ is hydrogen or methyl; and $R^8$ is methyl.

$R^3$ is Selected from One of the Following Groups (9a)-(9f):
(9a) —C(O)O$R^{30}$, —C(O)N(H)($R^{30}$), —S(O)$_2$O$R^{30}$, —S(O)$_2$N(H)($R^{30}$), or —P(O)(O$R^{30}$)$_2$.
(9b) —C(O)N(H)($R^{30}$) or —S(O)$_2$N(H)($R^{30}$).
(9c) —C(O)O$R^{30}$ or —C(O)N(H)($R^{30}$).
(9d) Any one of (9a)-(9c) wherein $R^{30}$ is hydrogen or $C_1$-$C_6$ alkyl.
(9e) Any one of (9a)-(9c) wherein $R^{30}$ is hydrogen.
(9f) —C(O)NH$_2$.

$R^6$ is Selected from One of the Following Groups (10a)-(10f):
(10a) —S(O)$_2$$R^{10}$ or —P(O)(O$R^{10}$)$_2$.
(10b) —S(O)$_2$$R^{10}$.
(10c) —P(O)(O$R^{10}$)$_2$.
(10d) Any one of (10a)-(10c) wherein each $R^{10}$ is independently $C_1$-$C_6$ alkyl or phenyl, wherein the phenyl is optionally substituted with one to two groups which are each independently $C_1$-$C_6$ alkyl, cyano, nitro, halogen, —O$R^{11}$, —N($R^{11}$)$_2$, —S$R^{11}$, —C(O)$R^{11}$, —C(O)O$R^{11}$, —C(O)N($R^{11}$)$_2$, —OC(O)O$R^{11}$, —OC(O)N($R^{11}$)$_2$, —N($R^{11}$)C(O)O$R^{11}$, —N($R^{11}$)C(O)N($R^{11}$)$_2$, —S(O)$R^{11}$, —S(O)$_2$$R^{11}$, —S(O)N($R^{11}$)$_2$, or —S(O)$_2$N($R^{11}$)$_2$, wherein each $R^{11}$ is independently hydrogen or $C_1$-$C_6$ alkyl.
(10e) Any one of (10a)-(10c) wherein each $R^{10}$ is independently $C_1$-$C_6$ alkyl or phenyl, wherein the phenyl is optionally substituted with one to two groups which are each independently $C_1$-$C_6$ alkyl or halogen.
(10f) Any one of (10a)-(10c) wherein each $R^{10}$ is independently $C_1$-$C_6$ alkyl or phenyl.

R$^3$ and R$^6$ are Selected from One of the Following Groups (11a)-(11h):
(11a) R$^6$ is —P(O)(OR$^{10}$)$_2$ and R$^3$ is —C(O)OR$^{30}$, —C(O)N(H)(R$^{30}$), —S(O)$_2$OR$^{30}$, —S(O)$_2$N(H)(R$^{30}$), or —P(O)(OR$^{30}$)$_2$.
(11b) R$^6$ is —P(O)(OR$^{10}$)$_2$ and R$^3$ is —C(O)N(H)(R$^{30}$) or —S(O)$_2$N(H)(R$^{30}$).
(11c) R$^6$ is —P(O)(OR$^{10}$)$_2$ and R$^3$ is —C(O)OR$^{30}$ or —C(O)N(H)(R$^{30}$).
(11d) Any one of (11a)-(11c) wherein R$^{30}$ is hydrogen or C$_1$-C$_6$ alkyl.
(11e) R$^6$ is —P(O)(OR$^{10}$)$_2$ and R$^3$ is —C(O)NH$_2$.
(11f) Groups (11a)-(11e), wherein each R$^{10}$ is independently C$_1$-C$_6$ alkyl or phenyl, wherein the phenyl is optionally substituted with one to two groups which are each independently C$_1$-C$_6$ alkyl, cyano, nitro, halogen, —OR$^{11}$, —N(R$^{11}$)$_2$, —SR$^{11}$, —C(O)R$^{11}$, —C(O)OR$^{11}$, —C(O)N(R$^{11}$)$_2$, —OC(O)OR$^{11}$, —OC(O)N(R$^{11}$)$_2$, —N(R$^{11}$)C(O)OR$^{11}$, —N(R$^{11}$)C(O)N(R$^{11}$)$_2$, —S(O)R$^{11}$, —S(O)$_2$R$^{11}$, —S(O)N(R$^{11}$)$_2$, or —S(O)$_2$N(R$^{11}$)$_2$, wherein each R$^{11}$ is independently hydrogen or C$_1$-C$_6$ alkyl.
(11g) Groups (11a)-(11e), wherein each R$^{10}$ is independently C$_1$-C$_6$ alkyl or phenyl, wherein the phenyl is optionally substituted with one to two groups which are each independently C$_1$-C$_6$ alkyl or halogen.
(11h) Groups (11a)-(11e), wherein each R$^{10}$ is independently C$_1$-C$_6$ alkyl or phenyl.

In embodiment (3) of the second aspect, the present disclosure provides compounds of formula (V), (Va), or (Vb), or an epimer thereof, wherein
each R$^1$ and R$^2$ is independently hydrogen, —C(O)R$^{40}$, or benzyl, wherein R$^{40}$ is C$_1$-C$_6$ alkyl, halomethyl, dihalomethyl, trihalomethyl, or C$_1$-C$_4$ alkoxymethyl;
R$^3$ is —C(O)OR$^{30}$, —C(O)N(H)(R$^{30}$), —S(O)$_2$OR$^{30}$, —S(O)$_2$N(H)(R$^{30}$), or —P(O)(OR$^{30}$)$_2$, wherein R$^{30}$ is hydrogen or C$_1$-C$_6$ alkyl; and
R$^6$ is —S(O)$_2$R$^{10}$ or —P(O)(OR$^{10}$)$_2$, wherein each R$^{10}$ is independently C$_1$-C$_6$ alkyl, C$_1$-C$_6$ haloalkyl, aryl, heteroaryl, C$_3$-C$_8$ cycloalkyl, or heterocyclyl.

The invention further comprises subgenera of embodiment (3) in which the substituents are selected as any and all combinations of R$^1$-R$^3$, and R$^6$ as defined herein, including without limitation, the following:
(a) R$^1$ and R$^2$ are selected from one of groups (8c)-(8g) as described above.
(b) R$^3$ is selected from one of groups (9b)-(9f) as described above.
(c) R$^6$ is selected from one of groups (10b)-(10f) as described above.
(d) R$^3$ and R$^6$ are selected from one of groups (11b)-(11h) as described above.

Microbubble Conjugates

In another aspect of the invention, microbubble conjugates are provided comprising (a) a microbubble comprising an outer shell, wherein the outer shell is derivatized with a first member of a specific binding pair; and (b) a compound according to the first aspect of the invention, wherein at least one R$^A$ or at least one R$^B$ comprises a second member of the specific binding pair (i.e., R$^{40}$ is a second member of the specific binding pair), bound to the microbubble, wherein the first member of the specific binding pair and the second member of the specific binding pair are bound to each other.

In yet another aspect of the invention, microbubble conjugates are provided comprising (a) a microbubble comprising an outer shell, wherein the outer shell is derivatized with a first member of a first specific binding pair; (b) a first compound according to the first aspect of the invention, wherein at least one R$^A$ or at least one R$^B$ comprises is a first member of a second specific binding pair (i.e., R$^{40}$ is a first member of a second specific binding pair); and (c) a second compound comprising the second members of the first and second specific binding pairs, wherein the second members of the first and second specific binding pairs bind to both first members of the first and second specific binding pairs, respectively, thereby binding the first compound to the microbubble.

Microbubbles are ultrasound contrast agents made of a shell enclosing a gas core. The shell is usually composed of albumin, galactose or lipids. The make-up of the gas core defines the ability of the microbubbles to strongly reflect ultrasound waves. Air or heavy insoluble gases such as perfluorocarbons or nitrogen (Lindner, J. R. *Nature Rev.*, 3, 527-532, 2004) are typically used. When microbubbles are administrated intravenously to the systemic circulation, their echogenicity allows contrast-enhanced ultrasound and improved medical sonography. In medical imaging, these agents have applications in radiology and cardiology. See Hamilton, A. J., et al., J. Am. Coll. Cardiol., 43, 453-60, (2004); Christensen, J. P., et al., Circulation, 96, 473-82 (2002). Currently, two FDA-approved microbubbles are available. Optison, made by GE Healthcare has an albumin shell and an octofluoropropane gas core, Levovist, made by Schering, had a lipid-galactose shell and air core (Lindner, J. R. supra).

In one preferred embodiment, the microbubbles have a diameter of about 0.1 to 10 microns. In a further preferred embodiment, the microbubbles have a diameter between 1-4 um, which allows the microbubbles to flow freely through the circulation and microcirculation. Circulation time can be greatly improved by the use of lipid-based membranes coated with longer chain fully saturated lipid molecules, such as distearoylphosphatidylcholine. See Rychak, J. J., et al., *J. Con. Rel.*, 114, 288-99, (2006). Microbubbles designed with low solubility gases such as decafluorobutane slowed the rate at which gas diffused into the bloodstream, thus allowing the microbubble to retain its structure longer. See Klibanov, A. L., *Bioconjugate Chem.*, 16, 9-17, (2005). With these characteristics, contrast agents can be regarded as pure intravascular tracers that behave similarly to red blood cells within the microcirculation and entry into the bloodstream is made possible by simple intravenous insertion via a catheter. See Lindner, J. R., supra.

The microbubbles are formed by entrapping the gas into a liquid. The microbubbles may be made of various insoluble gases such as fluorocarbon or sulfur hexafluoride gas. The liquid includes any liquid which can form microbubbles. Generally any insoluble gas can be used. It must be gaseous at body temperature and be nontoxic. The gas must also form stable microbubbles of average size of between about 0.1 and 10 microns in diameter when the pharmaceutical composition is sonicated to form microbubbles. Generally perfluorocarbon gases such as perfluoromethane, perfluoroethane, perfluoropropane, perfluorobutane, perfluoropentane are preferred. Other inert gases such as sulfur hexafluoride are also useful in forming microbubbles.

In one embodiment of the microbubble conjugates, the microbubble can further comprise one or more chemotherapeutic agents within the microbubble (e.g., an agent described above). Such chemotherapeutic-loaded microbubbles can be prepared for example, by preparing chemotherapeutic-loaded micelles via solvent exchange using a biodegradable copolymer such as, but not limited to, PEG-PLLA (polyethylene glycol-block-poly(1-lactic acid))

or PEG-PCL (polyethylene glycol-block-poly(ε-caprolactone)), followed by sonication of an aqueous solution of the micelles with a perfluorocarbon, as is familiar to one skilled in the art. For example, chemotherapeutic-loaded microbubbles can be prepared as described in Gao et al., *Ultrasonics* 2008, 48, 260-270; Hwang et al., "Development and Evaluation of Perfluorocarbon Nanobubbles for Apomorphine Delivery," *J. Pharm. Sci.* 2009, http://dx.doi.org/10.1002/jps.21687; and Rapoport et al., *J. Natl. Cancer Inst.* 2007, 99, 1095-1106, each of which is hereby incorporated by reference in its entirety.

Once the microbubbles are formed they may be stabilized by coating with a suitable lipid of protein, such as albumin, human gamma, globulin, human apotransferrin, Beta lactose and urease.

Microbubbles may be formed by sonication, typically with a sonicating horn. Sonication by ultrasonic energy causes cavitation within the dextrose albumin solution at sites of gas in the fluid. These cavitation sites eventually resonate and produce small microbubbles (about 7 microns in size) which are non-collapsing and stable. In general, sonication conditions which produce concentrations of greater than about $4 \times 10^{-8}$ M of between about 5 and about 6 micron microbubbles are preferred. Generally the mixture will be sonicated for about 80 seconds, while being perfused with an insoluble gas. A variety of other methods used to make microbubbles are described in published PCT application WO 96/39197. This same application also describes many of the gases which may be included within the microbubbles. Any such methods can be used to prepare microbubbles to be conjugated to a disaccharide containing compound as described herein (e.g., a compound of formula (II)).

Moreover, there are various sources of commercially available microbubbles that can be derivatized with the disaccharide compounds in analogy to what is described herein. For example, Optison® (GE HealthCare) and Levovist (Schering). In exemplary embodiments described herein the microbubbles used are Targestar$^B$ Ultrasound Contrast Agent. To create biotinylated microbubbles, a biotin-labeled conjugate is conjugated to Targestar$^B$ Targeted Ultrasound Contrast Agent (Targeson). Coupling Reagent (Targeson) is added to conjugated Targestar$^B$ microbubbles and incubated at room temperature with gentle agitation. The product is divided into two syringes, rinsed with Infusion Buffer, and then centrifuged. The infranatant is drained to 1 mL. A biotinylated-disaccharide, as described herein, is added to one of the vials and both can be incubated at room temperature with gentle agitation. To each sample is added Infusion Buffer before centrifugation. This solution is drained to 1.0 mL before recovery of the supernatant and repetition of the previous step. Finally, the supernatant is resuspended in Infusion Buffer.

Any suitable specific binding pair can be used to for binding the disaccharides described herein to the microbubble. Preferably, the binding pair is one with a dissociation constant of $10^{-3}$ M or less; in other embodiments, a dissociation constant of $10^{-4}$ M or less; $10^{-5}$ M or less; or $10^{-6}$ M or less. In one embodiment, the binding pair comprises biotin-streptavidin or biotin-avidin. Other non-limiting embodiments include metal/chelators binding pairs; protein/protein binding pairs; protein-cofactors binding pairs; (modified) nucleic acid-nucleic acid binding pairs; and protein/nucleic acid binding pairs. Any suitable method can be used to derivatize the microbubble and the disaccharide to incorporate the binding pair member into their structure; examples of such methods are provided below.

Once prepared, the conjugated microbubbles are transferred to a sterile syringe and injected parenterally into a subject (for example, a mammal), preferably near the target site of activity of the agent. The microbubbles prepared according to examples presented below can be used to attach specifically to tumor cells in any subject. The compositions are administered using conventional methods for delivering such compositions, i.e., using parenteral administration of microbubbles, preferably at or near the site of the tumor. The imaging of the tumor site is then achieved through conventional methods that involve imaging of diagnostic contrast agents.

Pharmaceutical Formulations and Dosage Forms

In another aspect, the present disclosure provides pharmaceutical compositions comprising a compound or an imaging agent as described above and a pharmaceutically acceptable carrier, diluent, or excipient.

Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

Methods of Use

In another aspect, the present invention provides methods of selectively targeting and/or treating a tumor comprising administering to a subject with a tumor a compound of the first aspect of the invention or a pharmaceutical composition of the third aspect, wherein at least one $R^A$ or at least one $R^B$ comprises a chemotherapeutic agent (i.e., $R^{40}$ is a chemotherapeutic agent), under conditions suitable to promote binding of the compound of the invention to the tumor. In one embodiment of the method, the composition comprises one or more further chemotherapeutic compounds (such as those described above), and the method is used to inhibit tumor growth and/or metastasis.

In a further aspect, the present invention provides methods for treating a cancer in a patient in need of such treatment are provided comprising administering to the patient a therapeutically effective amount of a compound according to the first aspect of the invention or a pharmaceutical composition of the third aspect, wherein at least one $R^A$ or at least one $R^B$ comprises a chemotherapeutic agent (i.e., $R^{40}$ is a chemotherapeutic agent).

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease, such as preventing tumor growth and/or metastasis;

(2) limiting the disease; for example, limiting a disease, condition or disorder in an individual who is experiencing or displaying the pathology or symptomatology of the disease, condition or disorder; for example, limiting tumor growth and/or metastasis, or limiting the rate of tumor growth and/or metastasis, or extending patient survival relative to untreated patents; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease, such as decreasing tumor size.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease, such as decreasing tumor size and/or incidence of metastasis, and/or increasing patient survival relative to untreated patients; or (ii) eliciting the referenced biological effect.

In these aspects, the saccharide portion of the compound according to the first aspect of the invention serves to target the composition to the tumor and/or cancerous cell(s). Any tumor type that the saccharides described herein can localize to, including, but not limited to, carcinomas of the breast, lung, prostate, and colon, astrocytoma, melanoma and renal carcinoma, can be treated using the methods of the invention, by appropriate use of compounds and compositions of the invention. One or more further chemotherapeutic compounds can be concurrently or sequentially administered to, for example, inhibit tumor growth and/or metastasis.

In such method for treating a tumor, a saccharide-chemotherapeutic conjugate according to the first aspect of the invention can act as a prodrug. The saccharide moiety can target the conjugate for delivery to a tumor within the body where it may dissociate, if necessary, from the saccharide and act upon the tumor itself.

In a further aspect, the present invention provides methods for selectively imaging a tumor in a patient, comprising administering to a subject with a tumor a compound according to the first aspect of the invention wherein at least one $R^A$ or at least one $R^B$ comprises an imaging agent (i.e., $R^{40}$ is an imaging agent) under conditions suitable to promote binding of the tumor targeting compound to the tumor; and (b) acquiring an image of the compound in the subject (e.g., ultrasound image, fluorescent image, radioimage, or magnetic resonance image).

In one preferred embodiment, the method is carried out following a treatment to inhibit tumor growth and/or metastasis, and wherein the method is used to monitor effects of the treatment. Since the saccharide moieties described herein can specifically target tumor cells, the mass of the tumor can be monitored diagnostically. For example, the tumor cells can be monitored before during and after therapy to determine the efficacy of the therapy and to verify delivery of the therapeutic to the tumor. Any tumor type that the saccharides described herein can localize, including, but not limited to, carcinomas of the breast, lung, prostate, and colon, astrocytoma, melanoma and renal carcinoma, can be imaged using the methods of the invention.

In certain preferred methods of the invention, saccharide-microbubble conjugates as described above are prepared and delivered to a subject in need thereof. The method preferred for practicing the delivery of the microbubble conjugates involves obtaining a composition comprising the saccharide-microbubbles conjugates of the invention; introducing the composition agent into the subject by intravenous injection, or intravenously (i.v. infusion) The microbubble is then processed in the subject. The presence of the saccharide covalently linked to the outer surface of the microbubble specifically targets the microbubble to tumor cells within the subject. The imaging of the tumor site is then achieved through conventional methods that involve imaging of diagnostic contrast agents.

In certain preferred methods of the invention, the saccharide-microbubble conjugates are prepared such that the microbubble comprises a payload of a chemotherapeutic agent (e.g., an agent described above) within the bubble and are delivered to a subject in need thereof. After providing the saccharide-microbubble conjugates to a patient as described above, the microbubble is then processed in the subject. The presence of the saccharide covalently linked to the outer surface of the microbubble specifically targets the microbubble to tumor cells within the subject. At the tumor site, the bubble eventually dissipates delivering the chemotherapeutic agent (as well as any additional agent within the microbubble) at the site of the tumor cells. By using such chemotherapeutic-loaded microbubble conjugates to target and deliver the chemotherapeutic payload to the tumor site, a greater concentration of chemotherapeutic can to localized at the tumor site upon dissipation of the microbubble.

Unless the context dictates otherwise, all embodiments of one aspect of the invention are suitable for use with other aspects of the invention, and the different embodiments can be combined.

The following examples are for illustration purposes only and are not intended to limit this invention in any way. It will be appreciated by those of skill in the art that numerous other disaccharide-bioactive agent combinations can be used in the invention and are even contemplated herein. In all the following examples, all parts and percentages are by weight unless otherwise mentioned, all dilutions are by volume.

DEFINITIONS

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$ alkoxycarbonyloxy and —OC(O)$C_1$-$C_6$ alkyl indicate the same functionality; similarly arylalkyl and -alkylaryl indicate the same functionality.

The term "epimer" as used herein means a diastereoisomeric compound having the opposite configuration at only one of two or more tetrahedral stereogenic centers present in the compound. For example, α-glucose and β-glucose are epimers.

The term "alkylamido" as used herein, means a —N(H)C(O)$R^0$ group, wherein $R^0$ is an alkyl group as defined herein. Examples of alkylamido include, but are not limited to, acetamido and pivaloylamido.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to a parent moiety via an oxygen atom. Representative examples of alkoxy include, but are not limited to, methoxy, ethoxy, n-propoxy, iso-propoxy, n-butoxy, sec-butoxy, iso-butoxy, tert-butoxy, n-pentoxy, isopentoxy, neopentyloxy, n-hexyloxy, 3-methylhexyloxy, 2,2-dimethylpentoxy, 2,3-dimethylpentoxy, n-heptyloxy, n-octyloxy, n-nonyloxy, and n-decoxy.

The term "alkoxyalkyl" as used herein, means an alkoxy group, as defined herein, appended to a parent moiety via an alkyl group, as defined herein. Representative examples of alkoxyalkyl include, but are not limited to, methoxymethyl, methoxyethyl, ethoxymethyl, ethoxyethyl, n-propoxymethyl, iso-propoxymethyl, n-butoxymethyl, sec-butoxymethyl, iso-butoxymethyl, and tert-butoxymethyl.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), a bicyclic ring system containing at least one phenyl ring or an aromatic bicyclic ring containing only carbon atoms in the aromatic bicyclic ring system. provided that the bicyclic ring system does not contain a heteroaryl ring when fully aromatic. The bicyclic aryl can be azulenyl, naphthyl, or a phenyl (base ring) fused to a monocyclic cycloalkyl, a monocyclic cycloalkenyl, or a monocyclic heterocyclyl. The bicyclic aryl is attached to the parent molecular moiety through any carbon atom contained within the base ring, or any carbon atom with the napthyl or azulenyl ring. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2,3-dihydrobenzo[b][1,4]dioxan-5-yl, and 2,3-dihydrobenzo[b][1,4]dioxan-6-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl.

The term "azido" as used herein means a —N$_3$ group.

The term "cyano" as used herein, mean a —CN group.

The term "cycloalkyl" as used herein, means a monocyclic or bicyclic ring system. Monocyclic ring systems are cyclic hydrocarbon groups containing from 3 to 8 carbon atoms, where such groups can be saturated (i.e., cycloalkanyl) or unsaturated (i.e., cycloalkenyl), but not aromatic. Examples of monocyclic cycloalkyls include cyclopropyl, cyclobutyl, cyclopentyl, cyclopentenyl, cyclohexyl, cyclohexenyl, cycloheptyl, and cyclooctyl. In certain embodiments, monocyclic cycloalkyl groups are fully saturated. Bicyclic cycloalkyl groups are a monocyclic cycloalkyl ring (base ring) fused to one ring selected from the group consisting of a phenyl ring, a monocyclic cycloalkyl, a monocyclic cycloalkenyl, a monocyclic heterocyclyl, and a monocyclic heteroaryl. The bicyclic cycloalkyl is attached to the parent molecular moiety through any carbon atom contained within the base ring. In certain embodiments, bicyclic cycloalkyl groups are a monocyclic cycloalkyl ring (base ring) fused to one ring selected from the group consisting of a phenyl ring, a 5 or 6 membered monocyclic cycloalkyl, a 5 or 6 membered monocyclic cycloalkenyl, a 5 or 6 membered monocyclic heterocyclyl, and a 5 or 6 membered monocyclic heteroaryl.

The term "halo" or "halogen" as used herein, means —Cl, —Br, —I or —F.

The term "haloalkyl" as used herein means an alkyl group, as defined herein, substituted with one or more halogen group, as defined herein. Examples of haloalkyls include, but are not limited to, trifluoromethyl, 2,2,2-trifluoroethyl, 2-chloroethyl, bromomethyl, and perfluorobutyl.

The term "halomethyl" as used herein means a methyl group substituted with one halogen group. Examples of halomethyl groups include fluoromethyl, chloromethyl, bromomethyl, and iodomethyl. The term "dihalomethyl" as used herein means a methyl group substituted with two halogen groups. Examples of dihalomethyl groups include, but are not limited to, difluoromethyl, dichloromethyl, dibromomethyl, chlorofluoromethyl, and bromochloromethyl. The term "trihalomethyl" as used herein means a methyl group substituted with three halogen groups. Examples of halomethyl groups include trifluoromethyl, trichloromethyl, tribromomethyl, and triiodomethyl.

The term "heteroaryl," as used herein, means a monocyclic or bicyclic heteroaryl ring system. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl ring (base ring) fused to a phenyl, a monocyclic cycloalkyl, a monocyclic cycloalkenyl, a monocyclic heterocyclyl, or a monocyclic heteroaryl. When the bicyclic heteroaryl contains a fused cycloalkyl, cycloalkenyl, or heterocyclyl ring, then the bicyclic heteroaryl group is connected to the parent molecular moiety through any carbon atom or nitrogen atom contained within the base ring. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, and thienopyridinyl. In certain embodiments, the bicyclic heteroaryl is a 5 or 6 membered monocyclic heteroaryl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl.

The term "heterocyclyl" as used herein, means a monocyclic or bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle ring (base ring) fused to a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the base ring. In certain embodiments, bicyclic heterocycles are a monocyclic heterocycle ring (base ring) fused to a phenyl, a 5 or 6 membered monocyclic cycloalkyl, a 5 or 6 membered monocyclic cycloalkenyl, a 5 or 6 membered monocyclic heterocycle, or a 5 or 6 membered monocyclic heteroaryl. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl.

The term "nitro" as used herein, means a —NO$_2$ group.

The term "saturated" as used herein means the referenced chemical structure does not contain any multiple carbon-carbon bonds. For example, a saturated cycloalkyl group as defined herein includes cyclohexyl, cyclopropyl, and the like. The term "unsaturated" as used herein means the referenced chemical structure contains at least one multiple carbon-carbon bond, but is not aromatic. For example, an unsaturated cycloalkyl group as defined herein includes cyclohexenyl, cyclopentenyl, cyclohexadienyl, and the like.

The term "trialkylsilyl" as used herein means a —Si(R$^0$)$_3$ group where each R$^0$ is independently an alkyl group as defined herein. Examples of trialkylsilyl include, but are not limited to, trimethylsilyl, t-butyldimethylsilyl, dimethylthexylsilyl, dimethylisopropylsilyl, diethylisopropylsilyl, and triisopropylsilyl.

As used herein, a "protecting group" refers to substituents of the alcohol or amine group commonly employed to block or protect the alcohol or amine functionality while reacting other functional groups within the compound. Examples of protecting group include, but are not limited to, —C(O)R$^{40}$, —CH$_2$O—R$^{41}$, —CH$_2$S—R$^{41}$, —CH$_2$CH$_2$O—R$^{42}$, —CH$_2$—R$^{43}$, —C(OR$^{44}$)(CH$_3$)$_2$, —CH$_2$CH$_2$—R$^{45}$, —SiR$^{46}$, —C(O)OR$^{47}$, t-butyl, allyl, propargyl, 1,4-dioxan-2-yl, tetrahydrofuran-2-yl, tetrahydropyran-2-yl, 3-bromotetrahydropyran-2-yl, tetrahydrothiofuran-2-yl, tetrahydrothiopyran-2-yl, 4-chlorophenyl, 4-methoxyphenyl, 4-nitrophenyl, 2,4-dinitrophenyl, or 2,3,5,6-tetrafluoro-4-trifluorophenyl, wherein R$^4$ is hydrogen, C$_1$-C$_6$ alkyl, C$_2$-C$_6$ alkenyl, halomethyl, dihalomethyl, trihalomethyl, C$_1$-C$_4$ alkoxymethyl, triphenylmethoxymethyl, phenoxymethyl, chlorophenoxymethyl, benzyl, diphenylmethyl, triphenylmethyl, phenyl, or pyridyl; $R^{41}$ is (i) $C_1$-$C_6$ alkyl, $C_2$-$C_6$ haloalkyl, $C_2$-$C_6$ alkenyl, —Si($R^{411}$)$_3$, —CH$_2$—Si($R^{411}$)$_3$, —CH$_2$CH$_2$—Si($R^{411}$)$_3$, $C_1$-$C_4$ alkoxyethyl, or menthyl, wherein each $R^{411}$ is $C_1$-$C_6$ alkyl or phenyl; (ii) benzyl wherein the phenyl ring thereof is optionally substituted with $C_1$-$C_4$ alkoxy or nitro; or (iii) phenyl optionally substituted with $C_1$-$C_4$ alkoxy; $R^{42}$ is (i) —CH$_2$CH$_2$—$R^{421}$ wherein $R^{421}$ is hydrogen, halogen, $C_1$-$C_4$ alkoxy, or tri($C_1$-$C_6$ alkyl)silyl; $R^{43}$ is phenyl optionally substituted with one group which is nitro, cyano, phenyl, azido, $C_1$-$C_4$ alkylamido, or trifluoromethyl; or one or two groups which are each halogen or $C_1$-$C_4$ alkoxy, $R^{44}$ is $C_1$-$C_4$ alkyl, benzyl, or phenyl; $R^{45}$ is tri($C_1$-$C_6$ alkyl)silyl, benzylthio, or phenylselenyl; each $R^{46}$ is independently $C_1$-$C_6$ alkyl, benzyl, or phenyl; and $R^{47}$ is $C_1$-$C_6$ alkyl, vinyl, allyl, benzyl, 4-methoxybenzyl, 3,4-dimethoxybenzyl, 2-nitrobenzyl, 4-nitrobenzyl, 2-dansylethyl, $C_1$-$C_4$ alkoxymethyl, 9-fluorenylmethyl, $C_1$-$C_4$ haloalkyl, p-nitrophenyl, —CH$_2$CH$_2$—Si($R^{471}$)$_3$, wherein each $R^{471}$ is $C_1$-$C_6$ alkyl or phenyl.

In certain embodiments, a protecting group is —C(O)$R^{40}$, —CH$_2$O—$R^{41}$, —Si$R^{46}$, —C(O)O$R^{47}$, t-butyl, allyl, propargyl, tetrahydropyran-2-yl, or benzyl, wherein $R^4$ is $C_1$-$C_6$ alkyl, halomethyl, dihalomethyl, trihalomethyl, $C_1$-$C_4$ alkoxymethyl, triphenylmethoxymethyl, phenoxymethyl, chlorophenoxymethyl, benzyl, diphenylmethyl, triphenylmethyl, or phenyl; $R^{41}$ is $C_1$-$C_6$ alkyl, $C_2$-$C_6$ haloalkyl, $C_1$-$C_4$ alkoxyethyl, or benzyl; each $R^{46}$ is independently $C_1$-$C_6$ alkyl, benzyl, or phenyl; and $R^{47}$ is $C_1$-$C_6$ alkyl, vinyl, allyl, benzyl, $C_1$-$C_4$ alkoxymethyl, 9-fluorenylmethyl, or $C_1$-$C_4$ haloalkyl.

As used herein, a "diol protecting group" refers to substituents of the alcohol group commonly employed to simultaneously block or protect the two alcohol functionalities which are in a 1,2- or 1,3-relationship to one another while reacting other functional groups within the compound. Examples of diol protecting groups include, but are not limited to, —C(O)—, —C($R^7$)($R^8$)— or —Si($R^9$)$_2$, wherein $R^7$ is hydrogen, $C_1$-$C_2$ alkyl, or phenyl; $R^8$ is hydrogen, $C_1$-$C_4$ alkyl, vinyl, trihalomethyl, phenyl, naphthyl, methoxyphenyl, or dimethoxyphenyl; or $R^7$ and $R^8$ taken together with the carbon to which they are both attached form a cyclopentyl or cyclohexyl group; and each $R^9$ is independently $C_1$-$C_6$ alkyl, benzyl, or phenyl. In certain embodiments, a diol protecting group is —C($R^7$)($R^8$)—, wherein $R^7$ is hydrogen or methyl; and $R^8$ is hydrogen, $C_1$-$C_4$ alkyl, vinyl, trihalomethyl, phenyl, naphthyl, methoxyphenyl, or dimethoxyphenyl.

The term "linker" as used herein refers to a divalent chemical moiety which connects two other chemical moieties.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, fumaric, toluenesulfonic, methanesulfonic, nitric, benzoic, citric, tartaric, maleic, hydroiodic, alkanoic such as acetic, HOOC—(CH$_2$)$_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

As used herein, the term "imaging agent" a chemical moiety which can provide a detectable signal. Such detectable signals include, but are not limited to, an optical signal generated upon interrogation with of the imaging agent with light (e.g., via light absorption, fluorescence, or light scattering) or upon a reaction of the imaging agent with a second chemical moiety (e.g., a chemiluminescent signal), and radioactive decay signal. Examples of imaging agents include, but are not limited to visible dyes, fluorescent dyes, semiconductor nanoparticles, and radioisotopes.

The term "chemotherapeutic agent" as used herein means a chemical moiety useful for the treatment of cancers, such as an anti-tumor agent, an anti-vascularizing agent, or a tumor suppressor agent.

The term "oligoalkylene glycol" as used herein means a linear oligoalkylene glycol, a branched oligoalkylene glycol, and a comb-oligoalkylene glycol, each comprising from about 1 to 1000 repeat units. In certain embodiments, an oligoalkylene glycol" is a linear oligoalkylene glycol.

The term "oligopeptide" as used herein means a peptide with fewer than about 20 amino acid residues.

The term "dendrimer" as used herein means a highly branched polymer or oligomer having a well-defined chemical structure comprising a core and a given number of generations of branches, or spindles, and end groups. The generations of spindles consist of structural units which are identical for the same generation of spindles and which may be identical or different for different generations of spindles. The generations of spindles extend radially in a geometrical progression from the core. The end groups of a dendrimer from the Nth generation are the end functional groups of the spindles of the Nth generation or end generation.

EXAMPLES

All solvents used were of analytical grade. $^1$H NMR spectra were recorded on a Varian 300 MHz spectrometer in chloroform-d (unless otherwise noted). Anhydrous solvents were purchased from VWR. All experiments were run under a dry nitrogen atmosphere in flame-dried glassware. All other chemicals were obtained from Aldrich and used without further purification.

Example 1

Formation of BLM A$_5$-Biotin Complex

Scheme 1

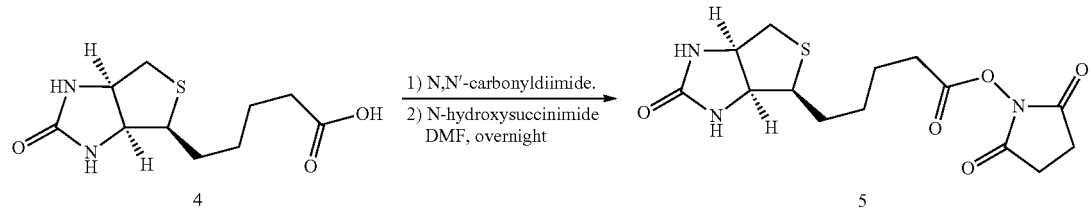

-continued
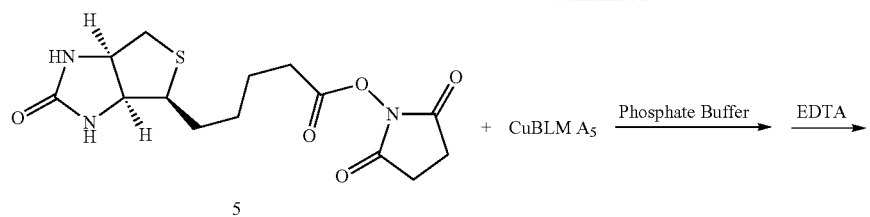
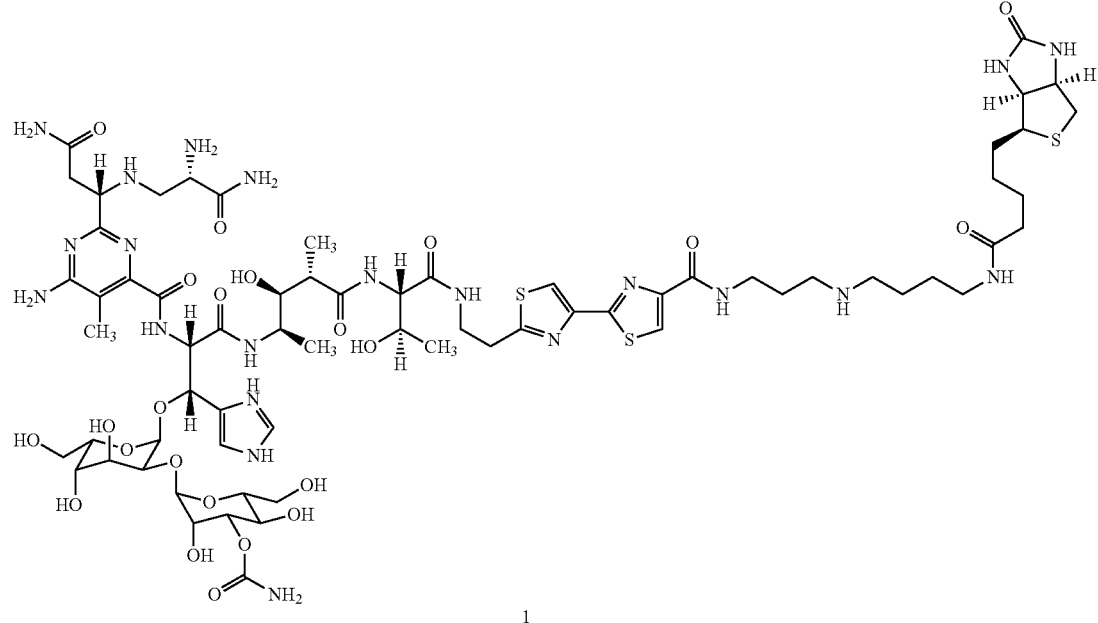
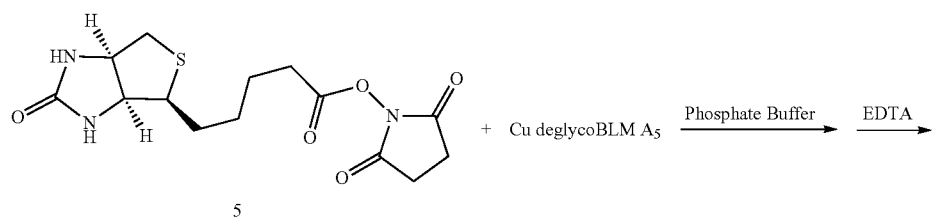
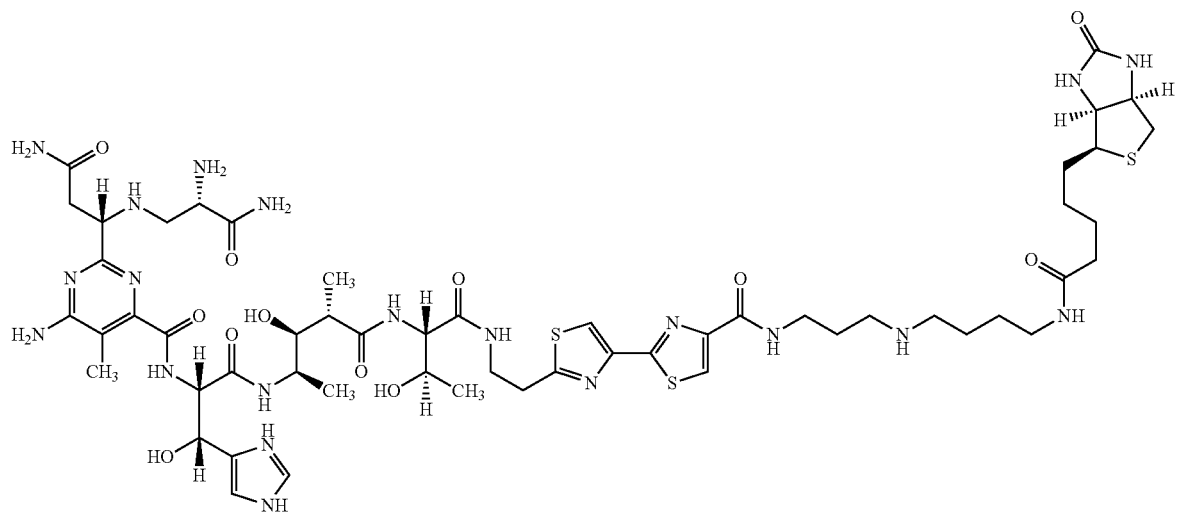

Example 2

Biotin N-Hydroxysuccinimide Ester (5)

To a solution containing 101 mg (0.41 mmol) of biotin in 2 mL of DMF at 78° C. was added 67 mg (0.41 mmol) of 1,1'-carbonyldiimidazole with continued heating until $CO_2$ evolution ceased. The solution was equilibrated to room temperature and stirred for an additional 3 h. To the reaction mixture was added a solution of 47 mg (0.41 mmol) of N-hydroxysuccinimide in 2 mL of DMF. The solution was stirred overnight at room temperature. The solvent was removed under diminished pressure and the product was crystallized from 2-propanol and then DMF-ether to afford 5 as a fine white powder: yield 95 mg (68%); $^1$H NMR (CDCl$_3$) δ 1.43-1.66 (m, 7H), 2.58 (m, 1H), 2.66 (t, 2H), 2.75 (s, 4H), 3.05 (m, 1H), 4.11 (m, 1H), 4.27 (m, 1H), and 6.36 (d, 2H, J=18.4 Hz); $^{13}$C NMR (CDCl$_3$) δ 55.19, 60.68, 63.46, 65.43, 69.11, 70.08, 73.25, 75.85, 79.05, 101.35, 101.83, 126.32, 127.20, 127.81, 128.11, 128.16, 128.48, 128.72, 129.18, 137.81, and 138.24; mass spectrum (MALDI-TOF), m/z 342.1 (M+H)$^+$.

Example 3

Biotinylated BLM $A_5$ (1)

To a solution containing 10 mg (6.7 μmol) of Cu(II).BLM $A_5$ in 3.0 mL of an aq. phosphate buffer, pH 8.0, at 0° C. was added 7.0 mg (21 μmol) of the N-hydroxysuccinimide ester of biotin (5). The reaction mixture was stirred at 0-4° C. for 48 h. The solution was then treated with three 5-mL portions of CHCl$_3$ to extract unreacted biotin ester 5. The solution was lyophilized to afford a blue powder. The product was dissolved in a 15% aq. EDTA solution and stirred overnight at room temperature. The resulting material was purified by reversed phase HPLC on a semi-preparative Alltima $C_{18}$ column (250 mm×10 mm). The column was washed with 0→65% CH$_3$CN in 0.1% TFA over a period of 45 min at a flow rate of 3.0 mL/min (monitoring at 292 nm): yield 3.2 mg (30%); mass spectrum (MALDI-TOF), m/z 1667.6 (M+H)$^+$; mass spectrum (TOF ES$^+$), m/z 833.8400 (M+Na)$^{++}$ ($C_{67}H_{103}N_{21}O_{23}S_3$ requires 833.8427).

Example 4

Biotinylated DeglycoBLM $A_5$ (2)

To a solution containing 10 mg (9.3 μmol) of deglycoBLM $A_5$ in 1 mL of H$_2$O was added 1.3 mg (9.3 μmol) of CuCl$_2$ at room temperature. The water was removed by lyophilization. The blue residue was dissolved in 3.0 mL of aq. phosphate buffer, pH 8.0, which was treated with 10 mg (27 μmol) of the N-hydroxysuccinimide ester of biotin (5) at 0° C. The solution was stirred at 0-4° C. for 48 h at which time the solution was extracted with three 5-mL portions of CHCl$_3$ to extract unreacted biotin ester 5. The solution was lyophilized to afford a blue powder. The residue was dissolved in a 15% aq. EDTA solution and stirred overnight at room temperature. The resulting mixture was purified by reversed phase HPLC on a semi-preparative Alltima $C_{18}$ column (250 mm×10 mm). The column was washed with 0→65% CH$_3$CN in 0.1% TFA over a period of 45 min at a flow rate of 3.0 mL/min (monitoring at 292 nm): yield 0.3 mg (3%); mass spectrum (MALDI-TOF), m/z 1322.0 (M+H)$^+$; mass spectrum (TOF ES$^+$), m/z 650.2861 (M+Na)$^{++}$ ($C_{54}H_{82}N_{20}O_{12}S_3$ requires 650.2870).

Example 5

Synthesis of the Disaccharide

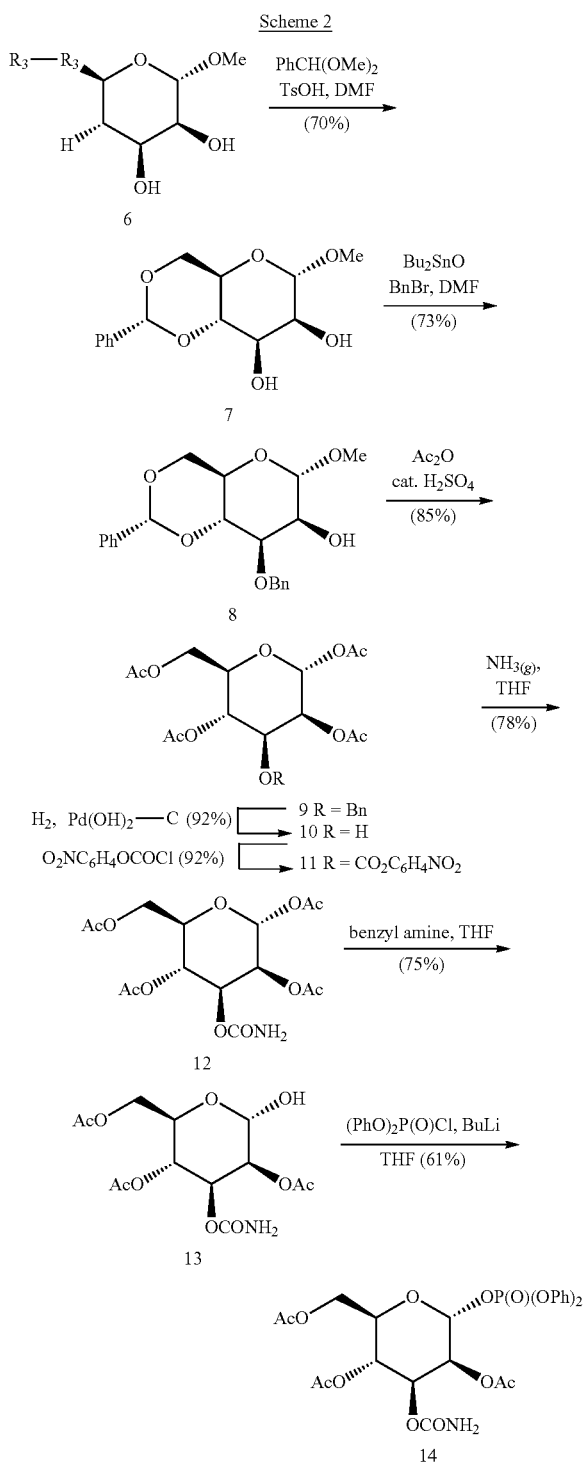

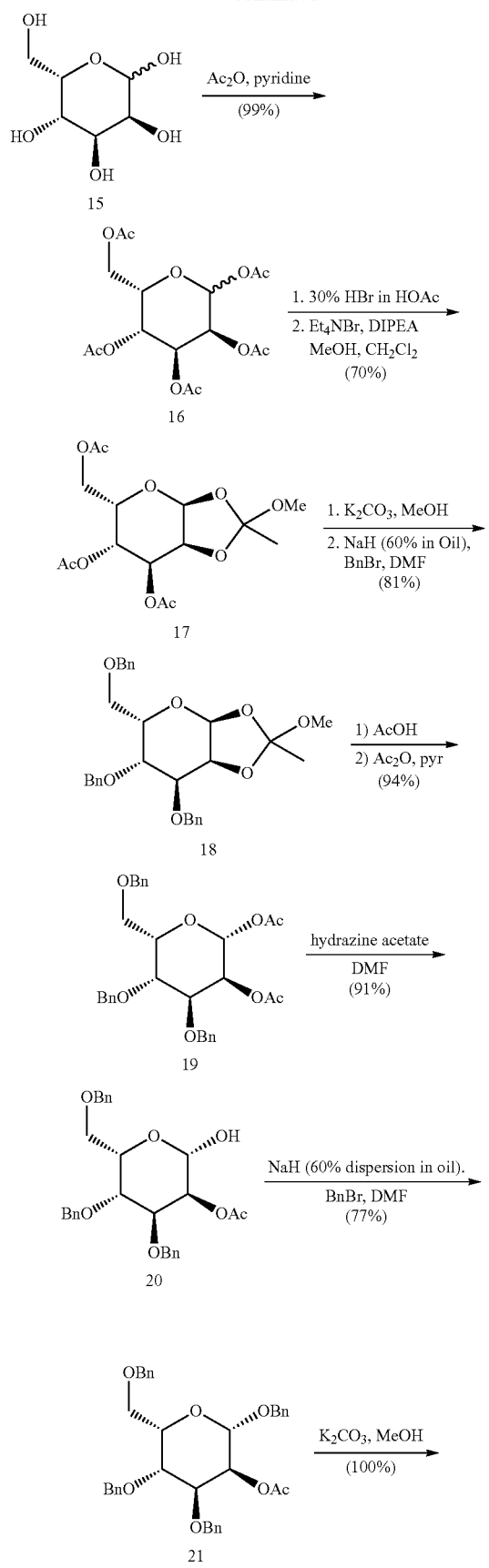

22

Example 6

Methyl 4,6-O-Benzylidene-α-D-mannopyranoside (7)

To a solution containing 7.00 g (36.0 mmol) of 6 in 85 mL of DMF was added 5.60 mL (37.3 mmol) of benzaldehyde dimethyl acetal and a catalytic amount of p-TsOH. The reaction mixture was swirled at 60° C. under reduced pressure for 1 h. The reaction mixture was poured into a stirred solution containing 120 mL of ethyl acetate and 100 mL of sat aq. NaHCO$_3$. The organic extract was washed with three 50-mL portions of brine, dried (MgSO$_4$), and concentrated under diminished pressure to afford a crude, colorless oil. The residue was purified by flash chromatography on a silica gel column (30 cm×5 cm). Elution with 4:1 hexanes-ethyl acetate afforded 7 as a colorless solid: yield 7.13 g (70%); silica gel TLC R$_f$ 0.31 (1:1 ethyl acetate-hexanes); $^1$H NMR (CDCl$_3$) δ 3.38 (s, 3H), 3.78 (m, 2H), 3.87 (m, 1H), 3.98 (m, 2H), 4.25 (m, 1H), 4.72 (d, 1H), 5.55 (s, 1H), 7.36 (m, 3H), and 7.47 (m, 2H); $^{13}$C NMR (300 MHz, CDCl$_3$) δ 55.25, 63.26, 68.78, 69.01, 71.07, 78.99, 101.63, 102.45, 126.55, 128.57, 129.49, and 137.45.

Example 7

8-Benzyloxy-6-methoxy-2-phenyl-hexahydro-pyrano[3,2-d][1,3]dioxin-7-ol (8)

To a solution containing 2.00 g (7.10 mmol) of 7 in 61 mL of MeOH was added 1.94 g (7.79 mmol) of Bu$_2$SnO and the solution was brought to reflux for 1.5 h to afford a clear solution. The solvent was removed under diminished pressure and the resulting solid was dried under vacuum overnight. The white residue was dissolved in 61 mL of DMF, treated with 1.69 mL (14.2 mmol) of BnBr, and heated to 100° C. for 30 min. The reaction mixture was cooled to room temperature and poured into a stirring solution of 90 mL of ethyl acetate and 60 mL of saturated aq. NaHCO$_3$. The organic phase was separated and washed with 60 mL of brine, dried (MgSO$_4$), and concentrated under diminished pressure. The residue was purified by flash chromatography on a silica gel column (30 cm×5 cm). Elution with 30% ethyl acetate in hexanes afforded 8 as a colorless oil: yield 1.93 g (73%); silica gel TLC R$_f$ 0.30 (30% ethyl acetate in hexanes); $^1$H NMR (CDCl$_3$) δ 3.38 (s, 3H), 3.77 (m, 3H), 4.05 (m, 2H), 4.27 (m, 1H), 4.70 (m, 2H), 4.84 (m, 1H), 5.62 (s, 1H), and 7.28-7.52 (m, 10H); $^{13}$C NMR (CDCl$_3$) δ 55.19, 60.68, 63.46, 65.43, 69.11, 70.08, 73.25, 75.85, 79.05, 101.35, 101.83, 126.32, 127.20, 127.81, 128.11, 128.16, 128.48, 128.72, 129.18, 137.81, and 138.24.

Example 8

Acetic Acid 3,5-Diacetoxy-6-acetoxymethyl-4-benzyloxytetrahydro-pyran-2-yl Ester (9)

To a solution containing 1.93 g (4.40 mmol) of 8 in 31 mL of Ac$_2$O was added a catalytic amount of H$_2$SO$_4$ and the solution was stirred for 40 min at room temperature. The solution was poured into a stirring two-phase solution of 120 mL of ethyl acetate and 80 mL of saturated aq. NaHCO$_3$. The organic phase was separated and washed with 60 mL of brine, dried (MgSO$_4$), and concentrated under diminished pressure. The residue was purified by flash chromatography on a silica gel column (30 cm×5 cm). Elution with 2:1 hexanes-ethyl acetate afforded 9 as a yellow oil: yield 1.94 g (85%); silica gel TLC R$_f$ 34 (30% ethyl acetate in hexanes); $^1$H NMR (CDCl$_3$) δ 2.02 (s, 3H), 2.07 (s, 3H), 2.11 (s, 3H), 2.15 (s, 3H), 3.83 (dd, 1H, J=9.7, 3.4 Hz), 3.90 (m, 1H), 4.04 (m, 1H), 4.19 (m, 1H), 4.41 (m, 1H), 4.64 (m, 1H), 5.24 (m, 1H), 5.34 (dd, 1H, J=3.4, 2.1), 6.09 (d, 1H, J=2.0 Hz), and 7.24-7.37 (m, 5H); $^{13}$C NMR (300 MHz, CDCl$_3$) δ 14.42, 20.98, 21.08, 21.13, 62.59, 67.01, 67.22, 70.98, 71.72, 74.30, 91.24, 127.99, 128.18, 128.65, 137.62, 168.32, 169.76, 170.23, and 171.01.

Example 9

Acetic Acid 2,5-Diacetoxy-6-acetoxymethyl-4-hydroxy-tetrahydropyran-3-yl Ester (10)

To a solution containing 1.20 g (2.73 mmol) of compound 9 in 30 mL of ethyl acetate was added a catalytic amount of Pd(OH)$_2$—C and the reaction was maintained under 1 atm of H$_{2(g)}$ overnight. The catalyst was removed by filtration through a pad of Celite 545® and concentrated under diminished pressure. The residue was purified by flash chromatography on a silica gel column (30 cm×5 cm). Elution with 75% ethyl acetate in hexanes afforded 10 as a colorless oil: yield 880 mg (92%); silica gel TLC R$_f$ 0.11 (1:1 ethyl acetate-hexanes); $^1$H NMR (CHCl$_3$) δ 2.04 (s, 3H), 2.09 (s, 3H), 2.13 (s, 3H), 2.15 (s, 3H), 3.95 (m, 1H), 4.04 (m, 1H), 4.09 (m, 1H), 4.19 (dd, 1H, J=12.3, 4.8 Hz), 5.07 (m, 1H), 5.13 (m, 1H), and 5.99 (m, 1H); $^{13}$C NMR (CDCl$_3$) δ 20.70, 20.84, 62.26, 68.04, 68.62, 70.27, 70.92, 90.44, 168.22, 170.33, 170.79, and 170.87.

Example 10

1,2,4,6-Tetra-O-((p-nitrophenyl)carbamoyl)-α-D-mannopyranose (11)

To a solution containing 1.17 g (3.36 mmol) of 10 in 12 mL of pyridine was added 1.64 g (13.4 mmol) of DMAP and 2.72 g (13.4 mmol) of p-nitrophenyl chloroformate. The reaction was stirred at 40° C. for 2 h at which time it was poured into a two-phase solution of mL of ethyl acetate and 7 mL of H$_2$O. The organic layer was washed with three 10-mL portions of 1 N HCl, 10 mL of saturated aq. NaHCO$_3$ and 10 mL of brine. The solution was dried (MgSO$_4$) and concentrated under diminished pressure. The residue was purified by flash chromatography on a silica gel column (30 cm×5 cm). Elution with 50% ethyl acetate in hexanes afforded 11 as a yellow oil: yield 1.58 g (92%); silica gel TLC R$_f$ 0.58 (1:1 ethyl acetate-hexanes); $^1$H NMR (CDCl$_3$) δ 2.07 (s, 3H), 2.09 (s, 3H), 2.14 (s, 3H), 2.17 (s, 3H), 4.04-4.12 (m, 2H), 4.25 (dd, 1H), 5.15 (dd, 1H), 5.38-5.45 (m, 2H), 6.11 (s, 1H), 7.34 (d, 2H), and 8.23 (d, 2H); $^{13}$C NMR (300 MHz, CDCl$_3$) δ 14.06, 20.64, 20.91, 60.25, 61.78, 64.87, 67.42, 70.49, 74.12, 90.51, 121.79, 125.22, 145.53, 148.82, 151.57, 155.09, 167.78, 169.30, 169.86, 170.47, and 170.99.

Example 11

Acetic Acid 3,5-Diacetoxy-6-acetoxymethyl-4-carbamoyloxy-tetrahydropyran-2-yl Ester (12)

To a solution containing 1.26 g (3.22 mmol) of 11 in 67 mL CH$_2$Cl$_2$ was added 23 mL of THF that had been saturated with NH$_{3(g)}$. The solution was stirred at room temperature for 6 h at which time the TLC indicated that the reaction was complete. The solution was concentrated under diminished pressure to afford a yellow oil. The residue was purified by flash chromatography on a silica gel column (30 cm×5 cm). Elution with 3:1 ethyl acetate-hexanes afforded 12 as a colorless oil: yield 742 mg (78%); silica gel TLC R$_f$ 0.10 (1:1 ethyl acetate-hexanes); $^1$H NMR (CDCl$_3$) δ 2.02 (s, 3H), 2.04 (s, 3H), 2.11 (s, 3H), 2.12 (s, 3H), 3.98-4.10 (m, 2H), 4.22 (dd, 1H, J=12.6, 5.0 Hz), 5.03 (br s, 2H), 5.18-5.30 (m, 3H), and 6.03 (d, 1H, J=1.7 Hz); $^{13}$C NMR (300 MHz, CDCl$_3$) δ 20.56, 20.64, 20.72, 61.92, 65.43, 68.60, 69.40, 70.38, 90.34, 155.25, 168.05, 169.58, 169.65, and 170.53.

Example 12

2,4,6-Tetra-O-carbamoyl-α-D-mannopyranosyl (13)

To a solution containing 593 mg (1.51 mmol) of 12 in 3.28 mL of THF was added 0.42 mL of benzylamine. The reaction was stirred at room temperature for 4 h until TLC indicated it was complete and was then concentrated under diminished pressure. The residue was purified by flash chromatography on a silica gel column (30 cm×5 cm). Elution with 75% ethyl acetate in hexanes afforded 13 as a colorless oil: yield 437 mg (83%); silica gel TLC R$_f$ 0.24 (75% ethyl acetate-hexanes); $^1$H NMR (CDCl$_3$) δ 2.06 (s, 3H), 2.09 (s, 3H), 2.15 (s, 3H), 4.15 (m, 1H), 4.23 (m, 2H), 4.83 (s, 2H), and 5.25 (m, 4H).

Example 13

Acetic Acid 5-Acetoxy-6-acetoxymethyl-4-carbamoyloxy-2-(diphenoxy-phosphoryloxy)-tetrahydropyran-3-yl Ester (14)

To a solution containing 372 mg (0.64 mmol) of 13 in 2 mL of THF at −78° C. was added 0.51 mL of BuLi. The solution was stirred for 10 min at which time 0.27 mL of diphenyl chlorophosphate was added. The solution was stirred an additional 10 min at −78° C. and it was then poured into a two-phase solution of 15 mL of ethyl acetate and 10 mL of saturated aq. NaHCO$_3$. The organic phase was washed with two 10-mL portions of brine, dried (MgSO$_4$), and concentrated under diminished pressure. The residue was purified by flash chromatography on a silica gel column (30 cm×3 cm). Elution with 3:1 ethyl acetate-hexanes afforded 14 as a colorless solid: yield 380 mg (61%); silica gel TLC R$_f$ 0.41 (60% ethyl acetate-hexanes); $^1$H NMR (CDCl$_3$) δ 1.98 (s, 3H), 2.07 (s, 3H), 2.16 (s, 3H), 3.89 (dd, 1H, J=12.4, 2.2 Hz), 4.08 (m, 1H), 4.17 (dd, 1H, J=12.4, 4.7 Hz), 4.66 (br s, 2H), 4.31 (m, 3H), 5.87 (dd, 1H, J=6.5, 1.6 Hz), and 7.20-7.39 (m, 10H); $^{13}$C NMR (CDCl$_3$) δ 20.27, 20.37, 61.38, 64.92, 68.57, 68.73, 68.88, 70.42, 95.71, 95.78, 119.73, 119.80, 119.90, 119.96, 125.51, 125.61, 129.69, 129.74, 149.65, 149.75, 149.84, 149.93, 155.13, 169.27, 169.53, and 170.29.

Example 14

Acetic Acid 2,4,5-Triacetoxy-6-acetoxymethyltetrahydropyran-3-yl Ester (16)

To a solution containing 1.01 g (5.60 mmol) of L-gulose in 10 mL of pyridine at 0° C. was added dropwise 5.25 mL (55.5 mmol) of Ac$_2$O. The solution was allowed to warm to room temperature and was stirred overnight. The resulting solution was diluted with 50 mL of ethyl acetate and poured over 20 g of ice. The organic and aqueous layers were separated and the aqueous layer was extracted with two 20-mL portions of ethyl acetate. The combined organic washings were washed with three 50-mL portions of 1 N HCl followed by 50 mL of $H_2O$ and 50 mL of brine. The organic layer was dried ($MgSO_4$), and concentrated under diminished pressure. The residue was purified by flash chromatography on a silica gel column (30 cm×7 cm). Elution with 1:1 ethyl acetate-hexanes afforded 16 as a colorless oil: yield 2.17 g (99%); silica gel TLC $R_f$ 0.42 (1:1 ethyl acetate-hexanes); $^1$H NMR ($CDCl_3$) δ 2.00 (s, 3H), 2.05 (s, 3H), 2.13 (s, 3H), 2.15 (s, 3H), 2.16 (s, 3H), 4.06 (m, 2H), 4.34 (m, 1H), 4.98 (m, 1H), 5.09 (dd, 1H, J=8.6, 3.4 Hz), 5.42 (m, 1H), and 5.98 (d, 1H, J=8.6 Hz); $^{13}$C NMR ($CDCl_3$) δ 20.56, 20.68, 20.89, 61.45, 67.17, 67.24, 67.43, 71.28, 89.81, 168.93, 169.14, 169.33, 169.39, and 170.42.

Example 15

Acetic Acid 6,7-Diacetoxy-2-methoxy-2-methyltetrahydro-[1,3]dioxolo[4,5-b]pyran-5-ylmethyl Ester (17)

To a solution containing 2.17 g (5.56 mmol) of 16 in 4.3 mL of AcOH was added 6.44 mL (36.7 mmol) of HBr (5.7 M in AcOH). The solution was stirred at room temperature for 4 h. This solution was diluted with 40 mL of $CH_2Cl_2$ and poured over 40 g of ice. The aqueous and organic layers were separated and the aqueous layer was extracted with two 25-mL portions of $CH_2Cl_2$. The combined organic extract was washed with 40 mL of saturated aq. $NaHCO_3$, dried ($MgSO_4$), and concentrated under diminished pressure. The resulting colorless oil was dried under vacuum overnight and then dissolved in 30 mL of $CH_2Cl_2$. To this solution was added 4 Å molecular sieves, 5 mL of MeOH, 0.85 mL (4.86 mmol) diisopropylethylamine (DIPEA), and 2.46 g (11.6 mmol) of $Et_4NBr$. The solution was stirred under $N_2$ overnight and then filtered through a pad of Celite 545®. The eluate was washed with three 50-mL portions of $H_2O$, 50 mL of saturated aq. $NaHCO_3$, and 50 mL of brine, dried ($MgSO_4$), and concentrated under diminished pressure. The residue was purified by flash chromatography on a silica gel column (38 cm×4 cm). Elution with 1:1 ethyl acetate-hexanes afforded 17 as a colorless oil: yield 1.40 g (70%); silica gel TLC $R_f$ 0.56 (1:1 ethyl acetate-hexanes); $^1$H NMR ($CDCl_3$) δ 1.69 (s, 3H), 2.03 (s, 6H), 2.08 (s, 3H), 3.26 (s, 3H), 4.11 (dd, 2H, J=6.6, 2.8 Hz), 4.27 (q, 1H, J=11.7, 5.8 Hz), 4.54 (dd, 1H, J=5.3, 2.9 Hz), 5.11 (dd, 1H, J=6.9, 2.9 Hz), 5.35 (dd, 1H, J=6.9, 5.2 Hz), and 5.64 (d, 1H, J=5.3 Hz); $^{13}$C NMR ($CDCl_3$) δ 20.60, 20.69, 20.77, 61.95, 65.47, 68.63, 69.47, 70.42, 90.37, 155.23, 168.07, 169.69, and 170.57.

Example 16

Acetic Acid 6-Acetoxy-5-acetoxymethyl-2-methoxy-2-methyl-tetrahydro-[1,3]dioxolo[4,5-b]pyran-7-yl Ester (18)

To a solution containing 1.40 g (3.88 mmol) of 17 in 10 mL of MeOH was added 100 mg (0.77 mmol) of $K_2CO_3$ and the reaction mixture was stirred at room temperature for 2 h. The solution was concentrated under diminished pressure and dried under high vacuum overnight. The residue was dissolved in 4 mL of DMF and added dropwise to a 0° C. solution containing 453 mg (15.1 mmol) of NaH in 7.25 mL of DMF. The combined solution was stirred at 0° C. for 30 min, at which time 1.80 mL (15.1 mmol) of benzyl bromide was added. The solution was warmed to room temperature and stirred overnight. Methanol (1.0 mL) was added and the solution was poured into 25 mL of ice water. The aqueous phase was extracted with three 50-mL portions of ethyl acetate and the combined organic extract was washed with 75 mL of brine, dried ($MgSO_4$), and concentrated under diminished pressure. The residue was purified by flash chromatography on a silica gel column (38 cm×4 cm). Elution with 1:2 ethyl acetate-hexanes afforded 18 as a colorless oil: yield 1.58 g (81%); silica gel TLC $R_f$ 0.84 (1:1 ethyl acetate-hexanes); $^1$H NMR ($CDCl_3$) δ 1.75 (s, 3H), 3.31 (s, 3H), 3.72-3.75 (m, 2H), 3.88 (m, 2H), 4.25 (m, 1H), 4.50-4.81 (m, 7H), 5.35 (d, 1H, J=5.2 Hz), and 7.25-7.42 (m, 15H); $^{13}$C NMR ($CDCl_3$) δ 19.61, 51.09, 68.55, 70.78, 71.73, 73.29, 73.99, 78.82, 97.79, 121.79, 127.55, 127.70, 127.92, 128.03, 128.30, 128.46, 137.54, 138.02, and 138.19.

Example 17

Acetic Acid 2-Acetoxy-4,5-bis-benzyloxy-6-benzyloxymethyl-tetrahydropyran-3-yl Ester (19)

To 1.12 g (2.21 mmol) of 18 was added 8.4 mL of glacial acetic acid and the resulting solution was stirred at room temperature for 1 h. The solution was concentrated under diminished pressure and co-evaporated several times with portions of toluene to remove traces of AcOH. The residue was treated with 5.6 mL of $Ac_2O$ and 5.6 mL of pyridine and then stirred at room temperature for 2.5 h. The reaction mixture was treated with ice and the aqueous and organic layers were separated. The organic layer was dried ($MgSO_4$) and concentrated under diminished pressure. The residue was purified by flash chromatography on a silica gel column (30 cm×3 cm). Elution with 1:2 ethyl acetate-hexanes afforded 19 as a colorless oil: yield 1.14 g (99%); silica gel TLC $R_f$ 0.55 (1:2 ethyl acetate-hexanes); $^1$H NMR ($CDCl_3$) δ 2.02 (s, 3H), 2.09 (s, 3H), 3.61-3.66 (m, 3H), 4.05 (t, 1H, J=3.5 Hz), 4.33 (m, 1H), 4.43-4.59 (m, 6H), 5.12 (dd, 1H, J=8.7, 3.2 Hz), 6.09 (d, 1H, J=8.7 Hz), and 7.23-7.39 (m, 15H); $^{13}$C NMR ($CDCl_3$) δ 21.16, 21.30, 68.08, 70.15, 73.05, 73.49, 73.56, 73.66, 73.89, 90.60, 127.98, 128.13, 128.18, 128.24, 128.56, 128.64, 128.70, 137.75, 137.82, 138.19, 169.65, and 170.05.

Example 18

Acetic Acid 4,5-bis-Benzyloxy-6-benzyloxymethyl-2-hydroxy-tetrahydropyran-3-yl Ester (20)

To a solution containing 1.14 g (2.13 mmol) of 19 in 17 mL of DMF was added 236 mg (2.56 mmol) of hydrazine acetate. The solution was stirred at room temperature for 1.5 h and then treated with 120 mL of ethyl acetate. The organic solution was washed with 250 mL of $H_2O$, 250 mL of saturated aq. $NaHCO_3$, and 250 mL of saturated aq. LiCl, dried ($MgSO_4$), and concentrated under diminished pressure. The residue was purified by flash chromatography on a silica gel column (30 cm×3 cm). Elution with 1:3 ethyl acetate-hexanes afforded 20 as a colorless oil: yield 950 mg (91%); silica gel TLC $R_f$ 0.29 (1:2 ethyl acetate-hexanes); $^1$H NMR ($CDCl_3$) δ 2.07 (s, 3H), 3.57-3.74 (m, 3H), 4.02 (m, 1H), 4.24 (m, 1H), 4.29 (m, 1H), 4.45-4.62 (m, 6H), 5.01 (dd, 1H, J=8.3, 3.1 Hz), 5.24 (m, 1H), and 7.27-7.40 (m, 15H).

Example 19

Acetic Acid 2,4,5-tris-Benzyloxy-6-benzyloxymethyl-tetrahydropyran-3-yl Ester (21)

To a solution containing 456 mg (0.93 mmol) of 20 in 10 mL of DMF at 0° C. was added 36 mg (1.21 mmol) of NaH. The reaction was stirred for 30 min, after which 0.22 mL (1.86 mmol) of BnBr was added. The reaction was allowed to warm to room temperature and was stirred overnight. MeOH (1.0 mL) was added and the reaction mixture, which was poured into 10 mL of ice water. The aqueous layer was extracted with three 30-mL portions of ethyl acetate. The combined organic layer was washed with 75 mL of brine, dried (MgSO$_4$), and concentrated under diminished pressure. The residue was purified by flash chromatography on a silica gel column (30 cm×3 cm). Elution with 1:5 ethyl acetate-hexanes afforded 21 as a colorless oil: yield 357 mg (67%); silica gel TLC R$_f$ 0.40 (1:4 ethyl acetate-hexanes); $^1$H NMR (CDCl$_3$) δ 2.09 (s, 3H), 3.51 (m, 2H), 3.61 (m, 1H), 3.92 (m, 1H), 4.39-4.85 (m, 9H), and 7.22-7.39 (m, 20H); $^{13}$C NMR (CDCl$_3$) δ 20.83, 68.29, 70.36, 70.68, 72.81, 73.26, 73.50, 73.78, 73.88, 104.55, 107.38, 127.73, 127.84, 128.00, 128.13, 128.38, 128.45, 137.32, 137.38, 137.77, and 169.77.

Example 20

2,4,5-Tris-benzyloxy-6-benzyloxymethyl-tetrahydropyran-3-ol (22)

To a solution containing 570 mg (1.05 mmol) of 21 in 23 mL of MeOH was added 92 mg (0.67 mmol) of K$_2$CO$_3$. The solution was stirred for 2 h at room temperature at which time it was poured into a two-phase solution of ethyl acetate (30 mL) and brine (15 mL). The organic phase was washed with two 15-mL portions of brine, dried (MgSO$_4$), and concentrated under diminished pressure. The residue was purified by flash chromatography on a silica gel column (30 cm×5 cm). Elution with 1:3 ethyl acetate-hexanes afforded 22 as a colorless oil: yield 530 mg (99%); silica gel TLC R$_f$ 0.40 (1:4 ethyl acetate-hexanes); $^1$H NMR (CDCl$_3$) δ 3.55 (d, 2H, J=6.6 Hz), 3.63 (m, 1H), 3.77 (t, 1H), 3.97 (t, 1H), 4.33 (m, 1H), 4.41-4.56 (m, 7H), 4.83 (d, 1H, J=12.0 Hz), 4.96 (d, 1H, J=4.3 Hz), and 7.23-7.38 (m, 20H); $^{13}$C NMR (CDCl$_3$) δ 68.70, 69.38, 70.45, 72.17, 72.64, 73.26, 73.33, 73.49, 75.79, 99.91, 127.58, 127.64, 127.75, 127.98, 128.15, 128.25, 128.30, 128.41, 128.45, 137.43, 137.58, 137.74, and 138.02.

Example 21

Disaccharide Formation

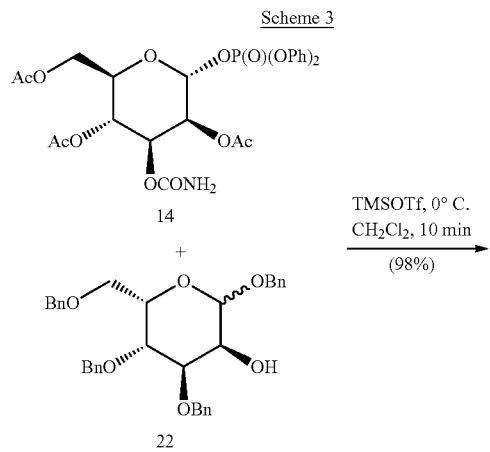

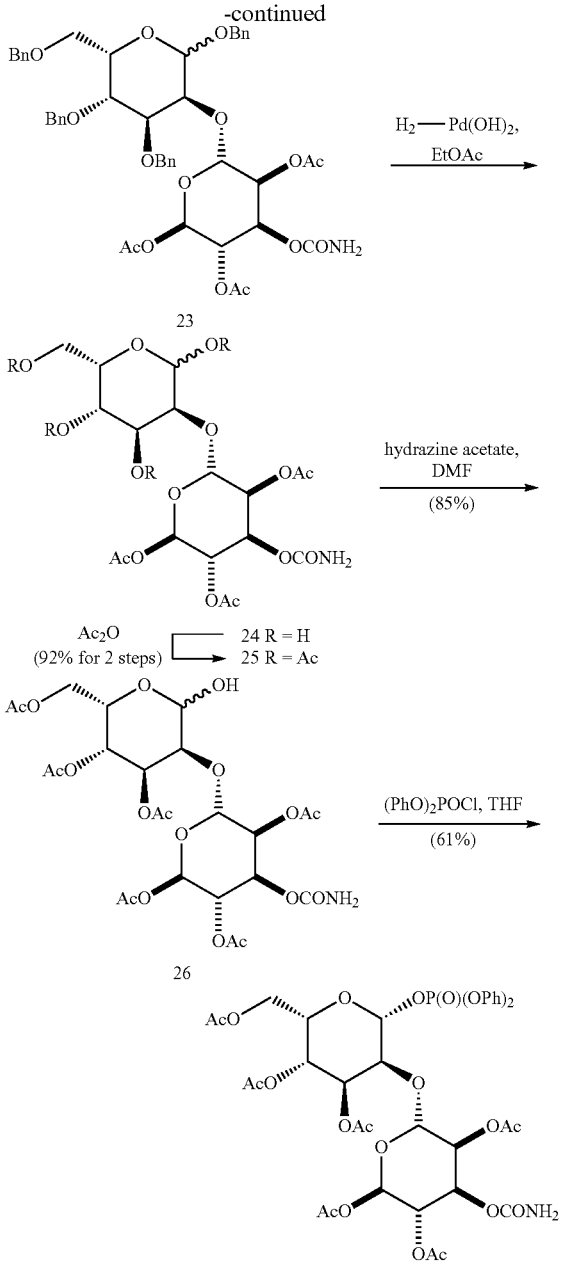

Example 22

1,3,4,5-Tetra-O-benzyl-2-O-(2,4,6-tri-O-acetyl-3-O-carbamoyl-α-D-mannopyranosyl)-β-L-gulopyranoside (23)

To a solution containing 100 mg (0.19 mmol) of 22 in 1.4 mL of CH$_2$Cl$_2$ was added a solution of 129 mg (0.22 mmol) of 14 in 1.4 mL of CH$_2$Cl$_2$. The solution was cooled to 0° C. and to it was added 0.11 mL of TMSOTf. The reaction was stirred for 10 min and was poured into a two-phase mixture of ethyl acetate (15 mL) and saturated aq. NaHCO$_3$ (9 mL). The organic layer was washed with two 5-mL portions of brine, dried (MgSO$_4$), and concentrated under diminished pressure. The residue was purified by flash chromatography on a silica gel column (10 cm×3 cm). Elution with 1:3 ethyl acetate-hexanes afforded 23 as a colorless oil: yield 160 mg (98%); silica gel TLC $R_f$ 0.37 (1:1 ethyl acetate-hexanes); $^1$H NMR (CDCl$_3$) δ 2.02 (s, 3H), 2.03 (s, 3H), 2.15 (s, 3H), 3.50-3.57 (m, 2H), 3.66 (d, 1H, J=2.8 Hz), 3.71 (dd, 1H, J=12.1, 1.7 Hz), 3.90 (t, 1H), 4.00 (m, 4H), 4.36-4.73 (m, 7H), 4.83-4.92 (m, 3H), 5.20-5.33 (m, 3H), and 7.19-7.42 (m, 20H); $^{13}$C NMR (CDCl$_3$) δ 20.63, 20.84, 61.98, 65.65, 68.64, 68.75, 69.73, 69.95, 70.02, 72.73, 73.02, 73.14, 74.98, 75.17, 96.32, 97.96, 127.24, 127.45, 127.50, 127.56, 127.83, 128.02, 128.08, 128.21, 128.31, 128.44, 137.56, 137.59, 137.99, 138.33, 155.26, 169.77, 169.86, and 170.41.

Example 23

Acetic Acid 2,5-Diacetoxy-6-acetoxymethyl-3-(3,5-diacetoxy-6-acetoxymethyl-4-carbamoyloxy-tetrahydro-pyran-2-yloxy)-tetrahydropyran-4-yl Ester (25)

To a solution containing 289 mg (0.33 mmol) of 23 in 22 mL of ethyl acetate was added 55 mg of 10% Pd(OH)$_2$—C. The reaction vessel was purged several times with H$_{2(g)}$ and stirred under H$_2$ overnight at room temperature. The solution was filtered through a pad of Celite 545® and concentrated under diminished pressure. The residue was dissolved in 11 mL of pyridine and treated with 0.31 mL of Ac$_2$O. The solution was stirred for 10 h at room temperature and poured into a two-phase mixture of ethyl acetate (20 mL) and H$_2$O (10 mL). The organic phase was washed with 10 mL of 10% HCl, 10 mL of saturated aq. NaHCO$_3$, and 10 mL of brine, the dried (MgSO$_4$), and concentrated under diminished pressure. The residue was purified by flash chromatography on a silica gel column (30 cm×4 cm). Elution with 2:1 ethyl acetate-hexanes afforded 25 as a colorless oil: yield 135 mg (61%); silica gel TLC $R_f$ 0.38 (2:1 ethyl acetate-hexanes); $^1$H NMR (CDCl$_3$) δ 2.05 (s, 3H), 2.06 (s, 3H), 2.07 (s, 3H), 2.14 (s, 6H), 2.16 (s, 3H), 2.20 (s, 3H), 3.98 (dd, 1H, J=8.4, 3.3 Hz), 4.09-4.30 (m, 2H), 4.38 (m, 1H), 4.85 (s, 2H), 5.00-5.26 (m, 7H), 5.45 (m, 1H), and 5.88 (d, 1H, J=8.4 Hz); $^{13}$C NMR (CDCl$_3$) δ 14.41, 20.92, 21.01, 21.05, 21.18, 21.27, 60.62, 61.58, 62.28, 65.71, 66.07, 67.86, 69.27, 69.39, 69.88, 71.52, 90.85, 95.18, 155.36, 168.91, 169.51, 169.65, 170.03, 170.70, and 170.77.

Example 24

Acetic Acid 5,6-Diacetoxy-4-carbamoyloxy-2-(4,5-diacetoxy-6-acetoxymethyl-2-hydroxy-tetrahydro-pyran-3-yloxy)-tetrahydro-pyran-3-yl Ester (26)

To a solution containing 100 mg (0.15 mmol) of 25 in 1.5 mL of DMF at 0° C. was added 16 mg (0.18 mmol) of hydrazine acetate. The solution was allowed to warm to room temperature and stirred for 1 h at which time the TLC analysis indicated the reaction was complete. The solution was diluted with 15 mL of ethyl acetate, washed successively with 25 mL of H$_2$O, 25 mL of saturated aq. NaHCO$_3$, 25 mL of saturated aq. LiCl, then dried (MgSO$_4$), and concentrated under diminished pressure. The residue was purified by flash chromatography on a silica gel column (30 cm×4 cm). Elution with 2:1 ethyl acetate-hexanes afforded 26 as a colorless oil: yield 81 mg (85%); silica gel TLC $R_f$ 0.30 (2:1 ethyl acetate-hexanes); $^1$H NMR (CDCl$_3$) δ 2.02 (s, 3H), 2.04 (s, 3H), 2.09 (s, 6H), 2.10 (s, 3H), 2.12 (s, 3H), 2.15 (s, 3H), 3.73 (dd, 1H, J=8.0, 3.4 Hz), 4.02-4.23 (m, 3H), 4.34 (m, 1H), 4.91-5.00 (m, 5H), 5.10 (m, 1H), 5.16 (d, 1H, J=3.3 Hz), 5.25 (m, 1H), and 5.37 (m, 1H); $^{13}$C NMR (CDCl$_3$) δ 13.64, 14.11, 19.04, 20.72, 29.62, 30.54, 60.37, 61.89, 62.08, 64.33, 65.81, 67.91, 68.71, 69.30, 69.92, 70.45, 72.45, 93.01, 95.23, 155.56, 169.28, 169.37, 169.48, 169.91, 170.56, and 170.86.

Example 25

Acetic Acid 3,4-Diacetoxy-6-(diphenoxy-phosphoryloxy)-5-(3,5,6-triacetoxy-4-carbamoyloxy-tetrahydropyran-2-yloxy)-tetrahydropyran-2-ylmethyl Ester (27)

To a solution containing 122 mg (0.19 mmol) of 26 in 5 mL of THF at −78° C. was added 0.16 mL (0.40 mmol) of BuLi. The solution was stirred for 10 minutes and then treated with 0.07 mL (0.31 mmol) of (PhO)$_2$POCl. The solution was stirred for an additional minutes and poured into a two-phase mixture of ethyl acetate (15 mL) and saturated aq. NaHCO$_3$ (7 mL). The organic phase was washed with two 5-mL portions of brine, dried (MgSO$_4$), and concentrated under diminished pressure. The residue was purified by flash chromatography on a silica gel column (30 cm×4 cm). Elution with 3:1 ethyl acetate-hexanes afforded 27 as a colorless oil: yield 102 mg (61%); silica gel TLC $R_f$ 0.30 (3:1 ethyl acetate-hexanes); $^1$H NMR (CDCl$_3$) δ 1.70 (s, 3H), 1.97 (s, 3H), 2.05 (s, 3H), 2.11 (s, 3H), 2.13 (s, 3H), 2.19 (s, 3H), 3.94-4.36 (m, 5H), 4.78 (s, 2H), 4.96 (d, 2H, J=5.0 Hz), 4.98 (m, 1H), 5.06-5.27 (m, 5H), 5.43 (m, 1H), 5.66 (dd, 1H), and 7.14-7.37 (m, 10H); $^{13}$C NMR (CDCl$_3$) δ 20.25, 20.59, 20.70, 61.07, 61.72, 65.34, 65.45, 67.32, 69.03, 69.81, 71.49, 95.32, 96.12, 120.13, 120.19, 125.50, 129.57, 129.84, 129.93, 154.98, 169.22, 169.31, 169.70, 170.31, and 170.51.

Example 26

Synthesis of the Biotinylated Disaccharide of BLM

Scheme 4

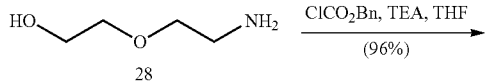

28

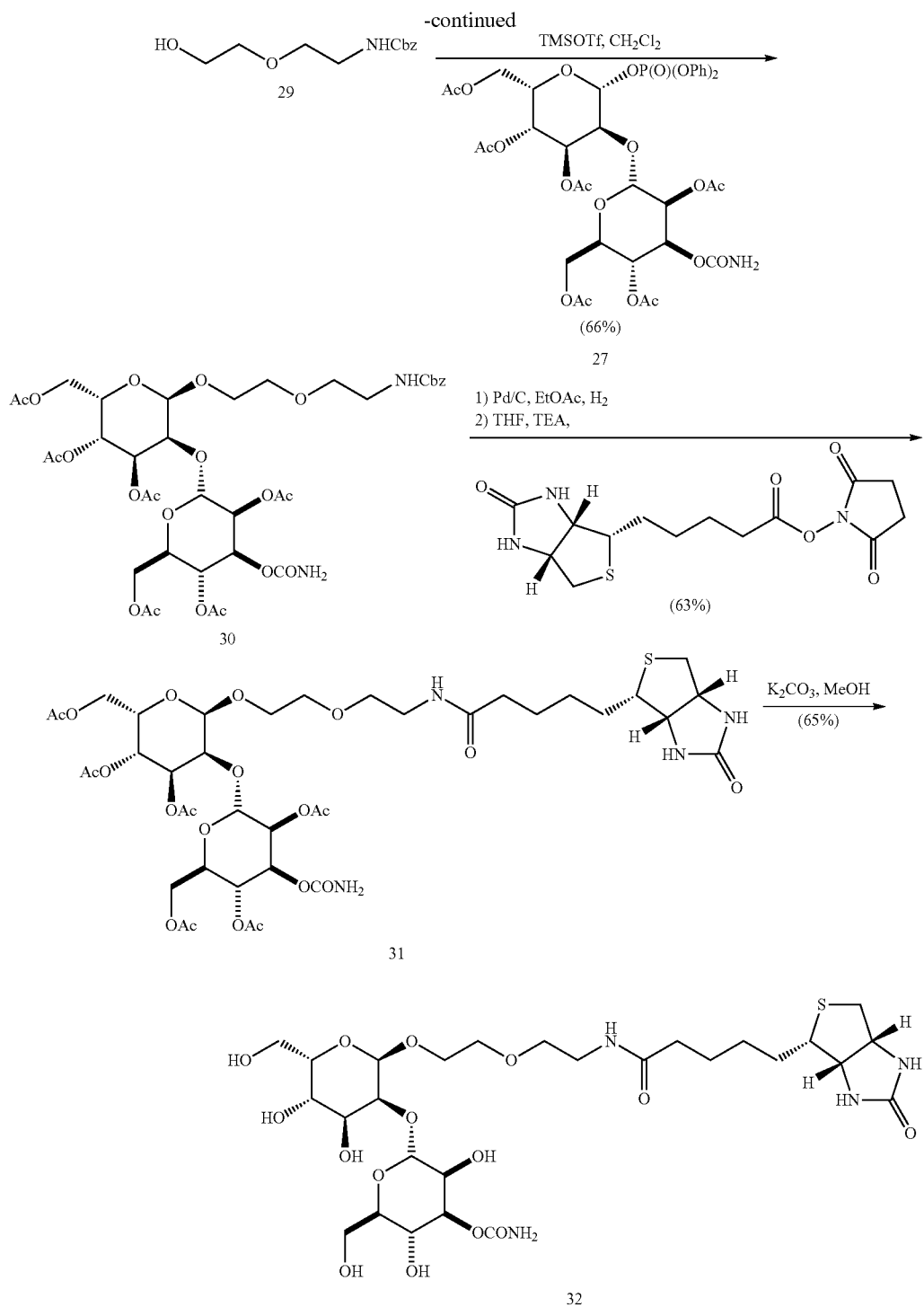

Example 27

Benzyl 2-(2-hydroxyethoxy)ethylcarbamate (29)

To a solution containing 1.01 g (9.61 mmol) of 2-(2-aminoethoxy)ethanol in 100 mL of THF at room temperature was added 1.34 mL of Et$_3$N and 1.49 mL of CbzCl. The reaction mixture was stirred for 1 h and diluted with 250 mL of ethyl acetate. The organic layer was washed with two 250-mL portions of H$_2$O, two 250-mL portions of brine, dried (MgSO$_4$), and concentrated under diminished pressure. The residue was purified by flash chromatography on a silica gel column (30 cm×4 cm). Elution with 9:1 ethyl acetate-hexanes afforded 29 as a colorless oil: yield 2.21 g (96%); silica gel TLC R$_f$ 0.30 (9:1 ethyl acetate-hexanes); $^1$H NMR (CDCl$_3$) δ 3.30 (m, 2H), 3.45 (m, 4H), 3.52 (s, 1H), 3.62 (m, 2H), 5.03 (s, 2H), 5.86 (m, 1H), and 7.27 (m, 5H); $^{13}$C NMR (CDCl$_3$) δ 40.54, 61.11, 66.31, 69.70, 71.96, 127.72, 127.75, 128.13, 136.28, and 156.50.

Example 28

(2R,3R,4S,5S,6R)-2-(Acetoxymethyl)-4-(carbamoyloxy)-6-((2S,3S,4S,5R,6S)-4,5-diacetoxy-6-(acetoxymethyl)-2-(2-(2-(benzyloxycarbonylamino)ethoxy)ethoxy) tetrahydro-2H-pyran-3-yloxy) tetrahydro-2H-pyran-3,5-diyl Diacetate (30)

To a solution containing 51 mg (59 µmol) of 27 in 7.5 mL of $CH_2Cl_2$ was added a solution of 15 mg (65 µmol) of 29 in 7.5 ml of $CH_2Cl_2$ at 0° C. To this cooled solution was added 0.07 mL (0.10 mmol) of TMSOTf and the reaction mixture was allowed to stir for 15 min at which time it was poured into a two-phase mixture of ethyl acetate (50 mL) and saturated aq. $NaHCO_3$ (7 mL). The organic phase was washed with two 25-mL portions of brine, dried ($MgSO_4$), and concentrated under diminished pressure. The residue was purified by flash chromatography on a silica gel column (30 cm×3 cm). Elution with 4:1 ethyl acetate-hexanes afforded 30 as a colorless foam: yield 33 mg (66%); silica gel TLC $R_f$ 0.30 (4:1 ethyl acetate-hexanes); $^1H$ NMR ($CDCl_3$) δ 2.03 (s, 6H), 2.07 (s, 3H), 2.09 (s, 3H), 2.11 (s, 3H), 2.12 (s, 3H), 3.40-3.68 (m, 8H), 3.83 (m, 1H), 3.96 (m, 1H), 4.05 (m, 4H), 4.25 (m, 1H), 4.46 (m, 1H), 4.69 (s, 1H), 4.91 (m, 1H), 5.00-5.25 (m, 8H), 5.61 (m, 1H), and 7.34 (m, 5H); $^{13}C$ NMR ($CDCl_3$) δ 20.63, 20.70, 20.82, 29.65, 40.88, 62.08, 62.46, 63.70, 65.54, 66.07, 66.57, 67.63, 68.55, 69.15, 69.61, 69.68, 70.04, 70.30, 70.63, 96.98, 97.08, 128.07, 128.17, 128.45, 136.53, 156.48, 169.35, 169.54, 169.81, and 170.53.

Example 29

(2R,3R,4S,5S,6R)-2-(Acetoxymethyl)-4-(carbamoyloxy)-6-((2R,3S,4S,5R,6S)-4,5-diacetoxy-6-(acetoxymethyl)-2-(2-(2-(5-((3aS,4S,6aR)-2-oxohexahydro-1H-thieno[3,4-d]imidazol-4-yl)pentanamido)ethoxy)ethoxy)tetrahydro-2H-pyran-3-yloxy) tetrahydro-2H-pyran-3,5-diyl Diacetate (31)

To a solution containing 3.0 mg (3.5 µmol) of 30 in 2.0 mL of ethyl acetate at room temperature was added ~1 mg of Pd/C. The reaction mixture was purged with $H_2$ and stirred under $H_2$ for 1 h at which time it was filtered through a pad of Celite 545® and concentrated under diminished pressure. The resulting residue was dissolved in 1.0 mL of THF at room temperature. To this solution was added 1.4 mg (4.0 µmol) of 5. The reaction mixture was stirred at room temperature for 2 h and concentrated under diminished pressure. The residue was purified by flash chromatography on a silica gel column (15 cm×2 cm). Elution with 4:1 ethyl acetate-hexanes afforded 32 as a colorless oil: yield 2.1 mg (63%); silica gel TLC $R_f$ 0.28 (4:1 ethyl acetate-hexanes); mass spectrum (MALDI-TOF), m/z 973.3 $(M+Na)^+$.

Example 30

(2R,3S,4S,5R,6R)-2-((2R,3S,4S,5S,6S)-4,5-dihydroxy-6-(hydroxymethyl)-2-(2-(2-(5-((3aS,4S,6aR)-2-oxohexahydro-1H-thieno[3,4-d]imidazol-4-yl)pentanamido)ethoxy)ethoxy)tetrahydro-2H-pyran-3-yloxy)-3,5-dihydroxy-6-(hydroxymethyl)tetrahydro-2H-pyran-4-yl Carbamate (32)

To a solution containing 2.3 mg (2.6 mmol) of 31 in 1.0 mL of MeOH at room temperature was added 0.1 mg (0.5 mmol) of $K_2CO_3$. The reaction mixture was stirred for 3 h at room temperature and diluted with 1.0 mL of water. The MeOH was removed under diminished pressure and the resulting mixture was purified by reversed phase HPLC on a semi-preparative Alltima $C_{18}$ column (250 mm×10 mm). The column was washed with 0→65% $CH_3CN$ in 0.1% TFA over a period of 45 min at a flow rate of 3.0 mL/min. After lyophilization of the appropriate fractions, compound 32 was obtained as a white powder: yield 1.2 mg (65%); mass spectrum (TOF $ES^+$), m/z 721.2556 $(M+Na)^+$ ($C_{27}H_{46}N_4O_{15}S$ requires 721.2597).

Example 31

Synthesis of a Fluorescein Disaccharide Conjugate

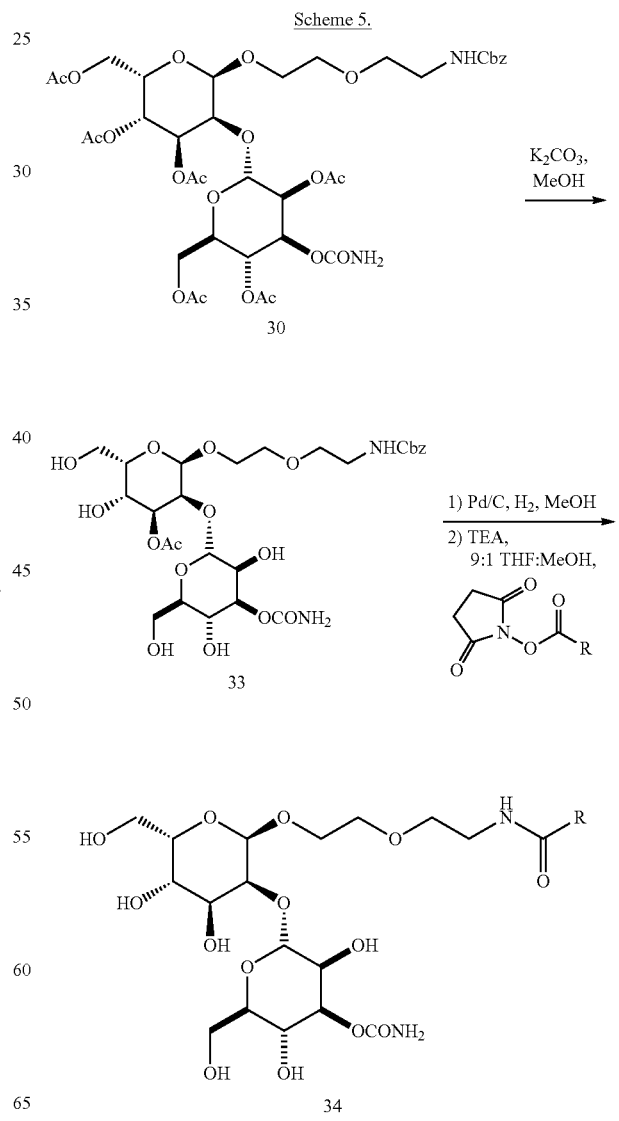

Scheme 5.

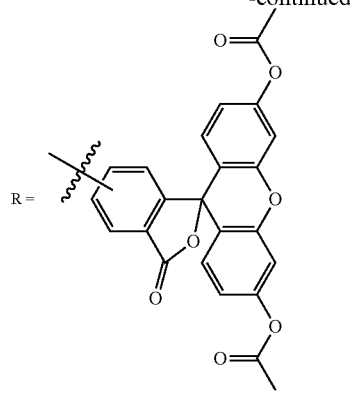

R =

Example 32

(2R,3S,4S,5R,6R)-2-((2R,3S,4S,5S,6S)-2-(2-(2-Benzyloxycarbonylaminoethoxy)ethoxy)-4,5-dihydroxy-6-(hydroxymethyl)tetrahydro-2H-pyran-3-yloxy)-3,5-dihydroxy-6-(hydroxymethyl)tetrahydro-2H-pyran-4-yl carbamate (33)

To a solution containing 10.0 mg (11.6 µmol) of 30 in 3.0 mL of MeOH at room temperature was added 0.5 mg (11.6 µmol) of $K_2CO_3$. The reaction mixture was stirred for 2 h and then diluted with 3 mL of water. The MeOH was concentrated under diminished pressure and the resulting material was purified by reversed phase HPLC on a semi-preparative Alltima C is column (250 mm×10 mm). The column was washed with 0→65% $CH_3CN$ in 0.1% TFA over a period of 45 min at a flow rate of 3.0 mL/min. After lyophilization of the appropriate fractions, compound 33 was obtained as a white powder: yield 6.3 mg (70%); mass spectrum (TOF $ES^+$), m/z 629.09 $(M+Na)^+$.

Example 33

(4,5)-(2-(2-((2R,3S,4S,5S,6S)-3-((2R,3S,4S,5R,6R)-4-(Carbamoyloxy)-3,5-dihydroxy-6-(hydroxymethyl)tetrahydro-2H-pyran-2-yloxy)-4,5-dihydroxy-6-(hydroxymethyl)tetrahydro-2H-pyran-2-yloxy)ethoxy)ethylcarbamoyl)-3-oxo-3H-spiro[isobenzofuran-1,9'-xanthene]-3',6'-diyl Diacetate (34)

To a solution containing 1.6 mg (2.6 µmol) of 33 in 3.0 mL of MeOH at room temperature was added ~1 mg of Pd/C. The reaction mixture was purged with $H_2$ and stirred under $H_2$ for 1 h at which time it was filtered through a pad of Celite 545® and concentrated under diminished pressure. The resulting residue was dissolved in 1.0 mL of 9:1 THF-MeOH at room temperature. To this solution was added one drop of triethylamine and 1.3 mg (2.4 µmol) of 5(6)-carboxyfluorescein diacetate N-succinimidyl ester. The reaction mixture was stirred at room temperature overnight in the dark and then concentrated under diminished pressure. Compound 34 was obtained as a mixture of products as a yellow oil: mass spectrum (TOF $ES^+$), m/z 937.25 $(M+Na)^+$.

Example 34

Cell Growth Conditions

The cell lines and corresponding growth media are summarized in Table 1.

TABLE 1

Cell lines and corresponding growth media.

| Cell Lines | Tumor/Normal Site | Growth Medium |
|---|---|---|
| MCF-7 | Breast carcinoma | RPMI-1640 medium |
| MCF-10A | Normal breast | MEBM Bullet Kit, 100 ng/mL cholera toxin |
| DU-145 | Prostate carcinoma | Eagle's Minimum Essential Medium (MEM) |
| *CRL-2221 | Normal prostate | RPMI-1640 medium |
| A-498 | Kidney carcinoma | Eagle's Minimum Essential Medium (MEM) |
| *CRL-2305 | Normal kidney | RPMI-1640 medium |
| A-549 | Lung carcinoma | RPMI-1640 medium |
| *CCL-75 | Normal lung | Eagle's Minimum Essential Medium (MEM) |
| SW-480 | Colon carcinoma | Leibovitz's L-15 medium |
| *CRL-1541 | Normal colon | Eagle's Minimum Essential Medium (MEM) |
| *HTB-12 | Brain astrocytoma | Leibovitz's L-15 medium |
| *CCL-204 | Normal brain | Eagle's Minimum Essential Medium (MEM) |
| *CRL-7622 | Bone osteosarcoma | Dulbecco's Modified Essential Medium (DMEM), high glucose |
| *CCL-211 | Normal bone | Dulbecco's Modified Essential Medium (DMEM), 1X glucose |
| *CRL-7637 | Skin melanoma | Dulbecco's Modified Essential Medium (DMEM), high glucose |
| *CRL-7636 | Normal skin | Dulbecco's Modified Essential Medium (DMEM), high glucose |

*denotes American Type Culture Collection (ATCC) designations

All completed media, except the mammalian epithelial basal medium (MEBM), contain 10% fetal bovine serum (FBS; HyClone, ThermoScientific) and antibiotics (100 units/mL penicillin and 100 µg/mL streptomycin; Gibco, Invitrogen). Cell lines were maintained at 37° C. under a humidified atmosphere of 5% $CO_2$ and 95% air, with the exception of the brain astrocytoma HTB-12 and the colon adenocarcinoma SW-480 cell lines, which were maintained in 100% air

Example 35

Microbubble Derivatization with Biotinylated Compounds

To create BLM $A_5$- and deglyco BLM $A_5$-microbubbles, the synthesized biotinylated compounds (1, 2 and 32) were conjugated to Targestar$^B$ Targeted Ultrasound Contrast Agents (Targeson). For each of these preparations, 400 µL of Coupling Reagent (Targeson) was added to 1.5 mL of conjugated Targestar$^B$ microbubbles and incubated for 20 min at room temperature, with gentle agitation every 5 min. The resulting product was divided into two syringes, each rinsed with 1.75 mL of Infusion Buffer, and then centrifuged for 3 min (400×g, 10° C.). The infranatant was then drained to 1 mL. For each separate preparation, fifty L containing 50 nM of the biotinylated compound was added to one of the vials and both were incubated at room temperature for 20 min with gentle agitation every 5 min. To each sample was added 1.75 mL of Infusion Buffer before centrifugation for 3 min at 400×g (10° C.). This solution was then drained to 1.0 mL before recovery of the supernatant and repetition of the previous step. Finally, the supernatant was resuspended in Infusion Buffer to a final volume of 2.0 mL. A schematic representation of the resulting targeted microbubble is shown in FIG. 1.

Example 36

Monitoring of Microbubble Attachment to Cultured Cells

Figure 2:
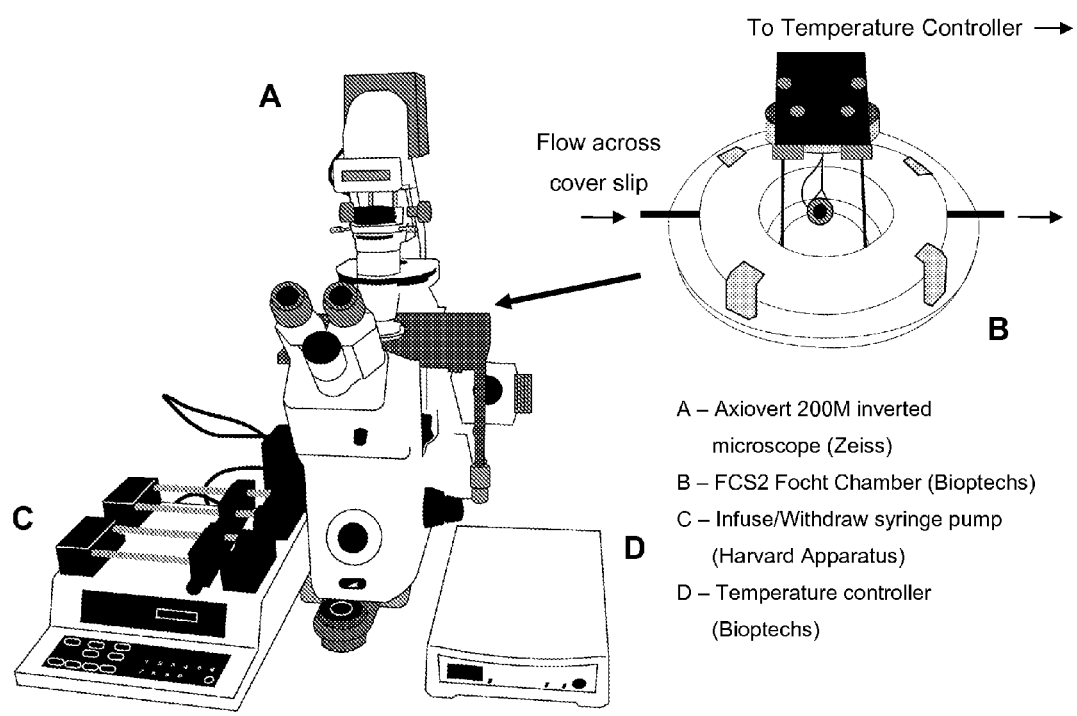
FIG. 2 illustrates an experimental platform for live-cell imaging of derivatized-microbubble attachment using an inverted microscope (A); cells are grown on glass cover slips for assembly in the Focht Chamber (B), which is maintained at constant temperature (D) at 37° C. A syringe pump (C) allows injection of the microbubble solution into the Chamber, both B and C constitute a closed system.

Attachment of the (biotinylated BLM $A_5$-, biotinylated deglyco BLM $A_5$-, and biotinylated BLM $A_5$ disaccharide-conjugated) microbubbles to the cultured cancer cells was imaged using an inverted microscope Zeiss Axiovert 200M fitted with an AxioCam MRm camera. Adherent cancer cells on 40 mm circular glass cover slips were assembled into a parallel plate flow chamber (Bioptechs FCS2, Micro-Environmental Systems) with a constant temperature maintained at 37° C. The prepared solution of microbubbles was introduced into the parallel plate flow chamber via ⅛-inch diameter tubing (Silastic) at a controlled rate of 0.01 mL/min using an adjustable infusion-withdrawal syringe pump (Harvard Apparatus, Holliston, Mass.). A negative control experiment was performed using a preparation of Targestar$^B$ microbubbles without any added biotinylated bleomycin $A_5$ ligand. The normal counterparts to each tumor cell line were used in parallel experiments for comparison purposes. FIG. 2 shows a representation of the experimental apparatus.

In order to use the derivatized microbubbles (FIG. 1) as a system for viewing tumor cell attachment using inverted microscopy, the importance of the streptavidin-biotin linkage between the microbubble surface and the biotinylated compounds of interest, specifically 1, was first validated.

Figure 3A:
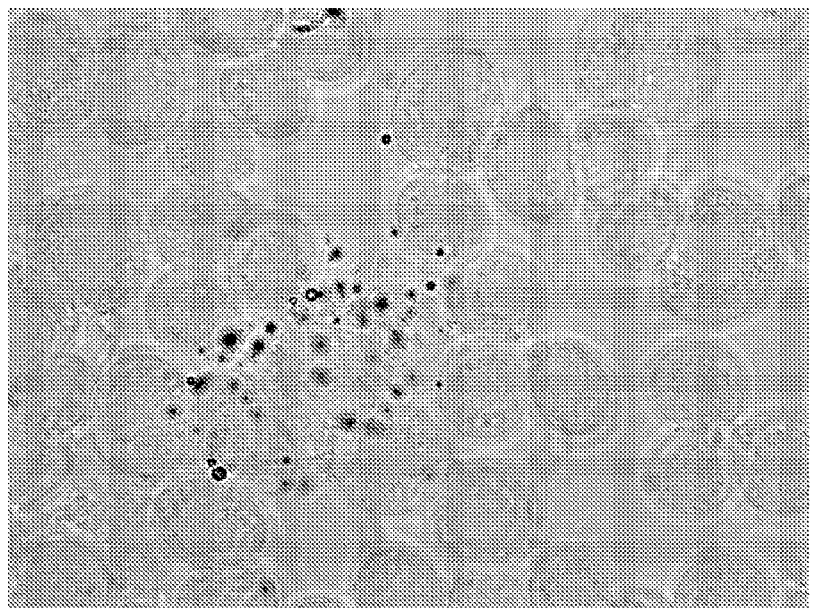
FIG. 3a shows the effect of BLM $A_5$-Microbubble conjugate [(1)-MB] on (A1) MCF-7 and (A2) MCF-10A cells.
Figure 3A:
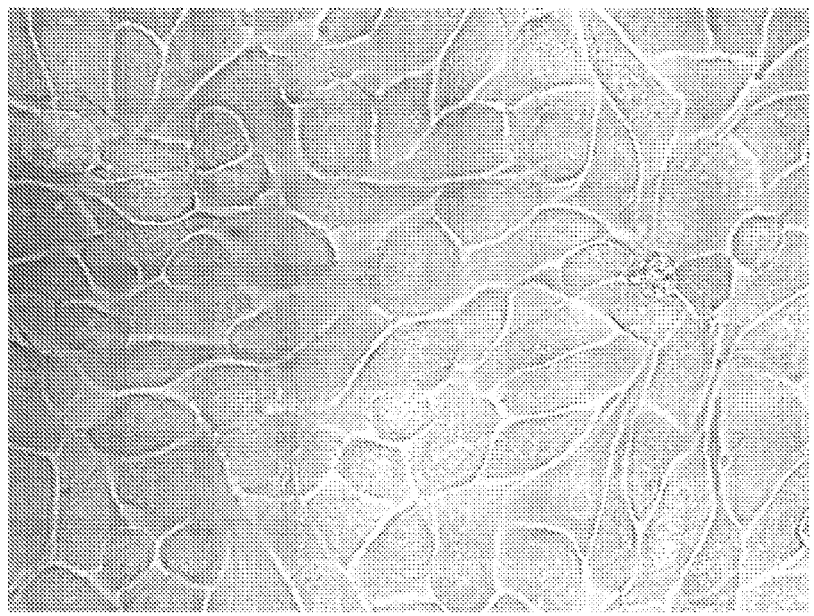
Figure 3B:
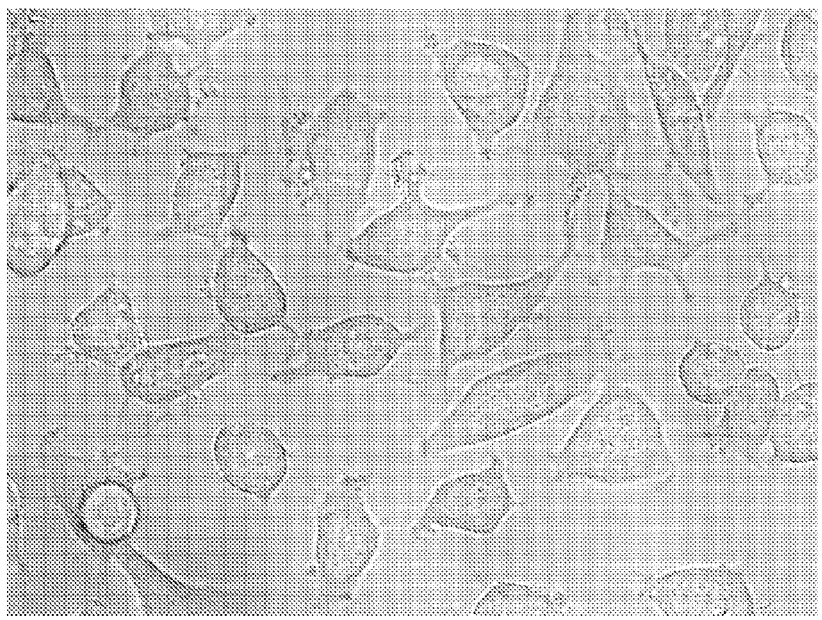
FIG. 3b shows the effect of deglycoBLM $A_5$-Microbubble conjugate [(2)-MB] on (B1) MCF-7 and (B2) MCF-10A cells.
Figure 3B:
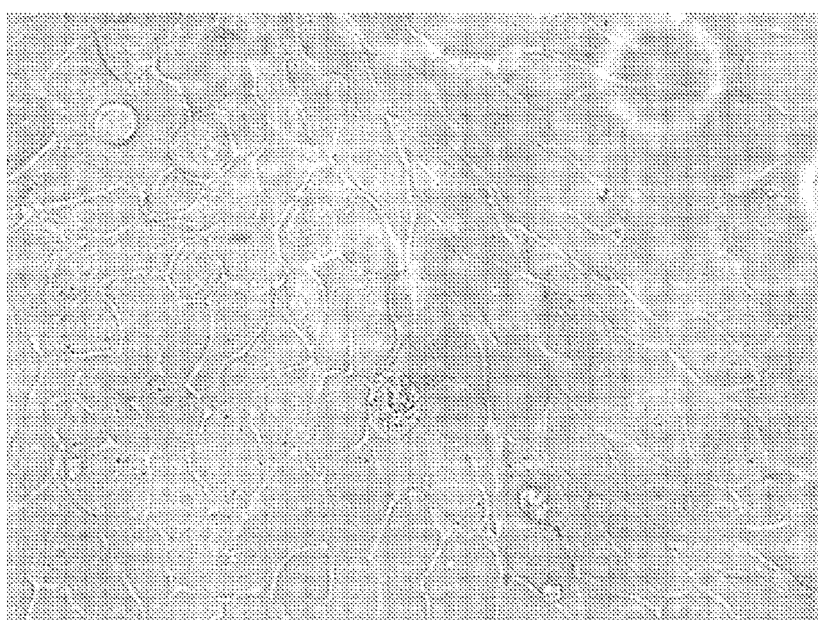
Figure 3C:
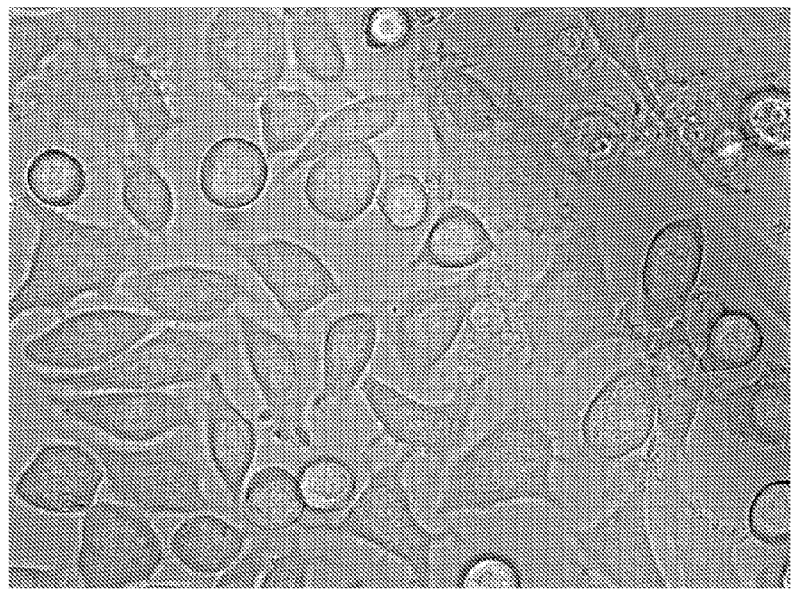
FIG. 3c shows the effect of an unconjugated mixture of BLM $A_5$ and microbubbles on (C1) MCF-7 and (C2) MCF-10A cells.
Figure 3C:
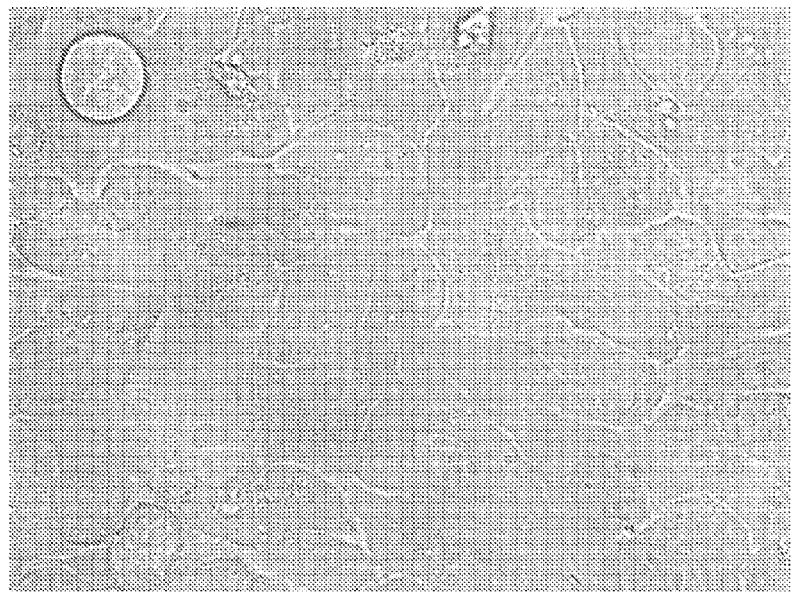
Figure 3D:
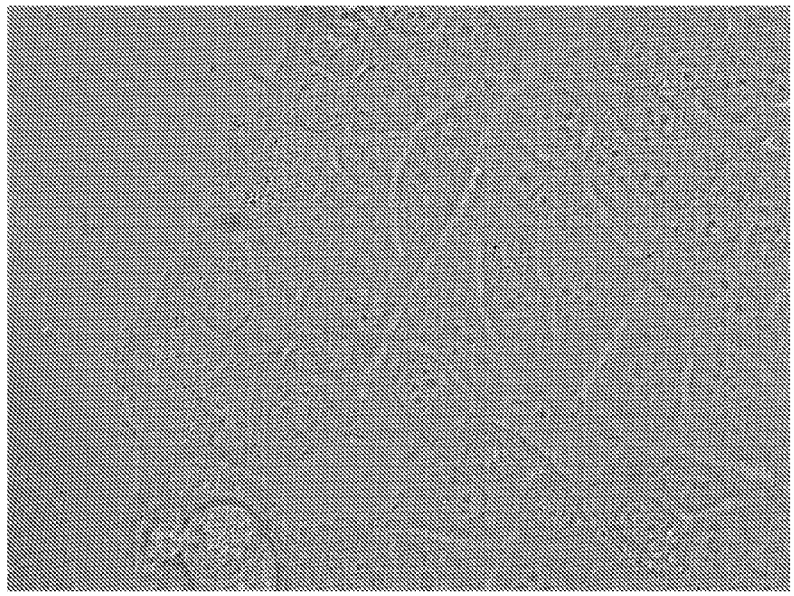
FIG. 3d shows the effect of unconjugated microbubbles on (D1) MCF-7 and (D2) MCF-10A cells.
Figure 3D:
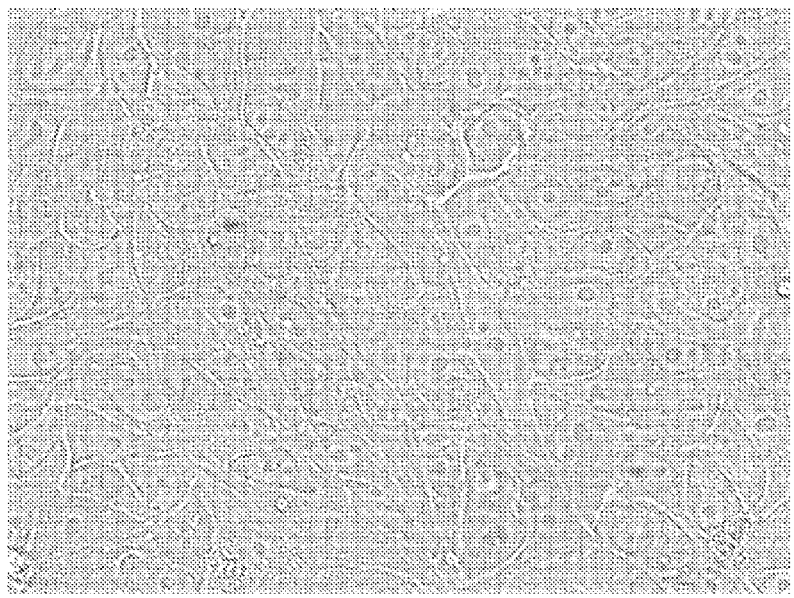

Bleomycin as a metal chelate can interact with tumor cells, as shown in numerous previous studies. However, this biochemical-molecular interaction cannot be visualized on the microscopic level without the conjugation of bleomycin to a larger particle, such as a microbubble (FIG. 3c, C1). Furthermore, the microbubble alone will not attach to a tumor cell without the direction of an attached bleomycin ligand (FIG. 3d, D1). Thus, cell recognition can only be visualized microscopically by aid of the streptavidin-biotin covalent interaction between bleomycin and the microbubble surface (FIG. 3a, A1).

The tumor-specificity of bleomycin is also shown when comparing the results of BLM $A_5$-microbubble attachment in MCF-7 (breast carcinoma) cells and MCF-10A (normal breast epithelial) cells. As seen in FIG. 3a, the bleomycin-microbubble conjugate [(1)-MB] only attached to the tumor cells (FIG. 3a, A1), and showed no attachment to the normal counterpart (FIG. 3a, A2). Thus, bleomycin attached to the microbubble surface via biotinylation still retains its tumor-specific nature.

With this system, it was then possible to validate the importance of the disaccharide for tumor cell binding specificity. To test this, biotinylated deglycosylated BLM $A_5$ (2) was conjugated onto the surface of the microbubble [(2)-MB] in the same manner as for 1. When a solution of deglyco BLM $A_5$-conjugated microbubbles was passed over MCF-10A, no attachment was seen as expected (FIG. 3b, B2). However, when the same solution was passed over MCF-7 breast carcinoma cells, no attachment was seen either (FIG. 3b, B1). Since the only difference between BLM $A_5$ and deglyco BLM $A_5$ is the removal of the disaccharide moiety, then the carbohydrate of bleomycin must be essential for tumor cell binding specificity, as described previously.

Figure 4A:
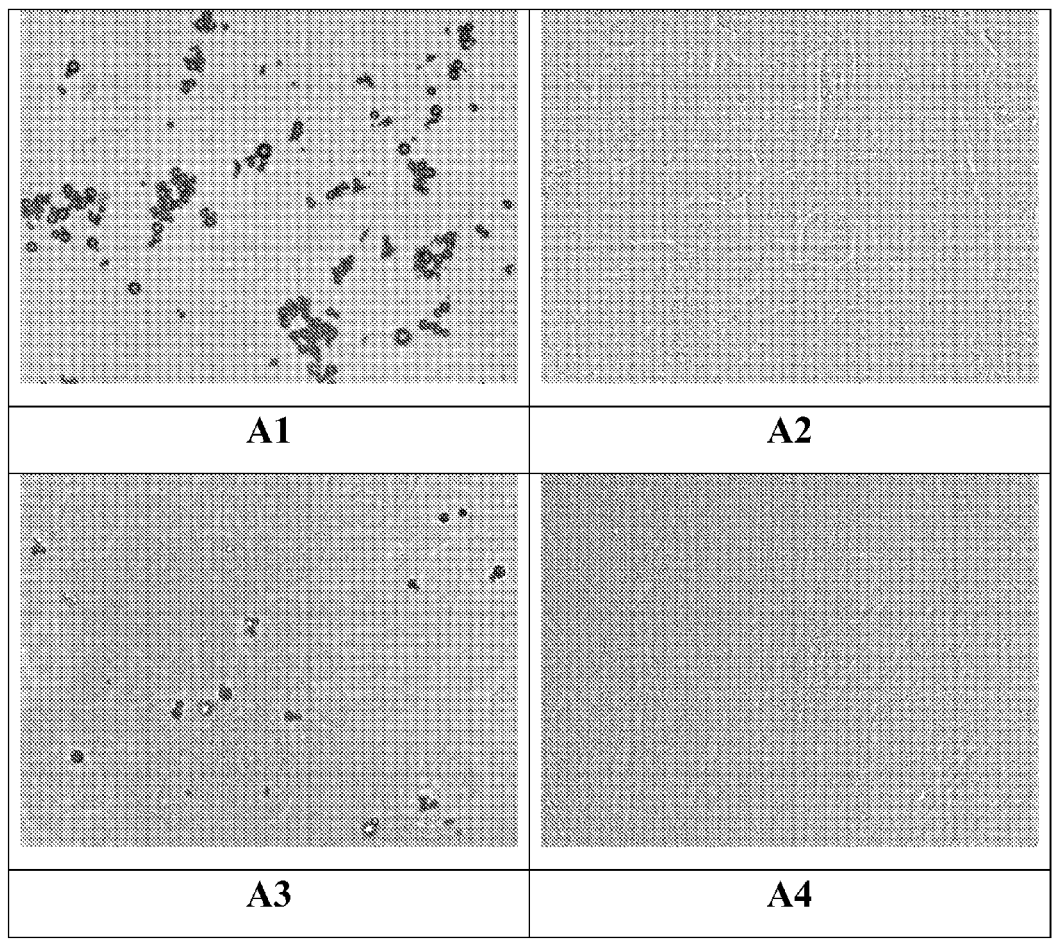
FIG. 4a shows the effect of a compound (32)-Microbubble conjugate [(32)-MB] on (A1) MCF-7; (A2) MCF-10A; (A3) A-549; and (A4) CCL-75 cells.

The finding that the disaccharide moiety is required for tumor cell recognition, raised the seemingly unlikely possibility that all of the information necessary for tumor targeting might be contained in the carbohydrate moiety. Small molecules like the disaccharide have not been demonstrated previously to be capable of tumor targeting. Nonetheless, the disaccharide moiety of BLM was prepared by multi-step total synthesis, and this sugar itself was biotinylated. When the biotinylated sugar was conjugated onto the microbubble, it showed preferential attachment to MCF-7 tumor cells over MCF-10A cells (FIG. 4a). Furthermore, these results resembled the preferential attachment seen when the entire BLM $A_5$ molecule was conjugated to the microbubble. Thus, the disaccharide moiety of bleomycin contains all of the information required for tumor targeting.

This unanticipated finding prompted the study of tumor cell recognition for other cell line pairs (tumor and normal counterparts) besides MCF-7 and MCF-10A. The biotinylated disaccharide (32) was added to cell lines from seven other common anatomical sites of cancerous growth (Table 2).

TABLE 2

Attachment of BLM $A_5$ disaccharide-microbubbble [(32)-MB] and BLM $A_5$-microbubble conjugates to individual cell lines.

| | Cell Lines | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| (32) – MB | ++ | – | + | – | + | – | + | – | + | – | – | – | + | – | + | + |
| (1) – MB | ++ | – | ++ | – | ++ | +/– | ++ | – | + | – | – | – | + | – | + | +/– |
| (1) + MB | – | – | – | – | – | – | – | – | – | – | – | – | – | – | – | – |
| MB | – | – | – | – | – | – | – | – | – | – | – | – | – | – | – | – |

1: MCF-7 (Breast carcinoma
5: DU-145 (Prostate carcinoma)
9: CRL-7637 (Skin Melanoma)

2: MCF-10A (Normal Breast)
6: CRL-2221 (Normal Prostate)
10: CRL-7636 (Normal Skin)

3: SW-480 (Colon carcinoma)
7: A-549 (Lung carcinoma)
11: CRL-7622 (Bone carcinoma)

4: CRL-1541 (Normal Colon)
8: CCL-75 (Normal Lung)
12: CCL-221 (Normal Bone)

TABLE 2-continued

Attachment of BLM $A_5$ disaccharide-microbubbble [(32)-MB] and BLM $A_5$-microbubble conjugates to individual cell lines.

| | | | | | | | Cell Lines | | | | | | | | |
|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 |

| 13: HTB-12 (Brain Astrocytoma) | 14: CCL-204 (Normal Brain) | 15: A-498 (Kidney Carcinoma) | 16: CRL-2305 (Normal Kidney) |
|---|---|---|---|

"(##) – MB"—microbubble conjugated to compound ##;
"(##) + MB"—mixture of microbubble and compound ##, not conjugated;
"MB" = microbubble
(++) very high positive attachment;
(+) positive attachment, and (−) no attachment observed under experimental conditions;
(+/−) notation indicates that positive attachment was viewed, but only under limited trials or dispersed throughout the microscopic field with possible statistical revelance.

Figure 4B:
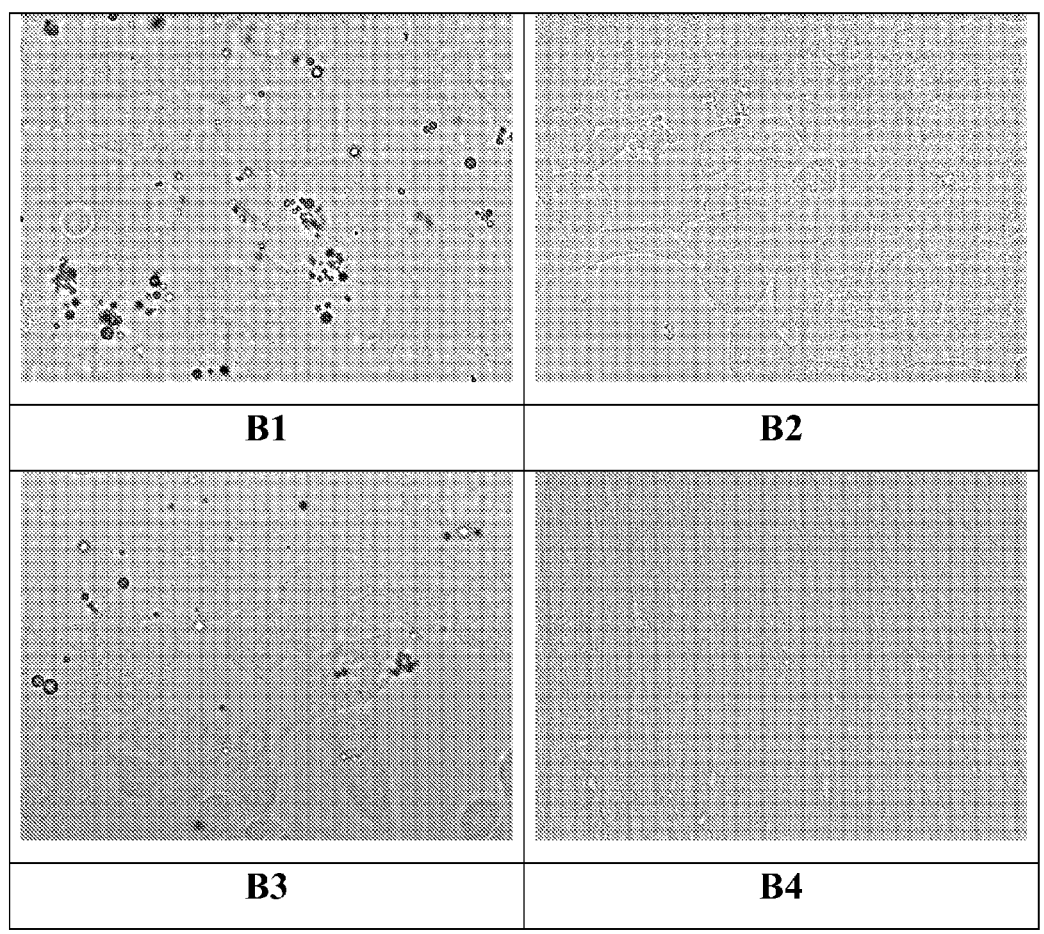
FIG. 4b shows the effect of Microbubble conjugate (1)-MB on (B1) MCF-7; (B2) MCF-10A; (B3) A-549; and (B4) CCL-75 cells.
Figure 4C:
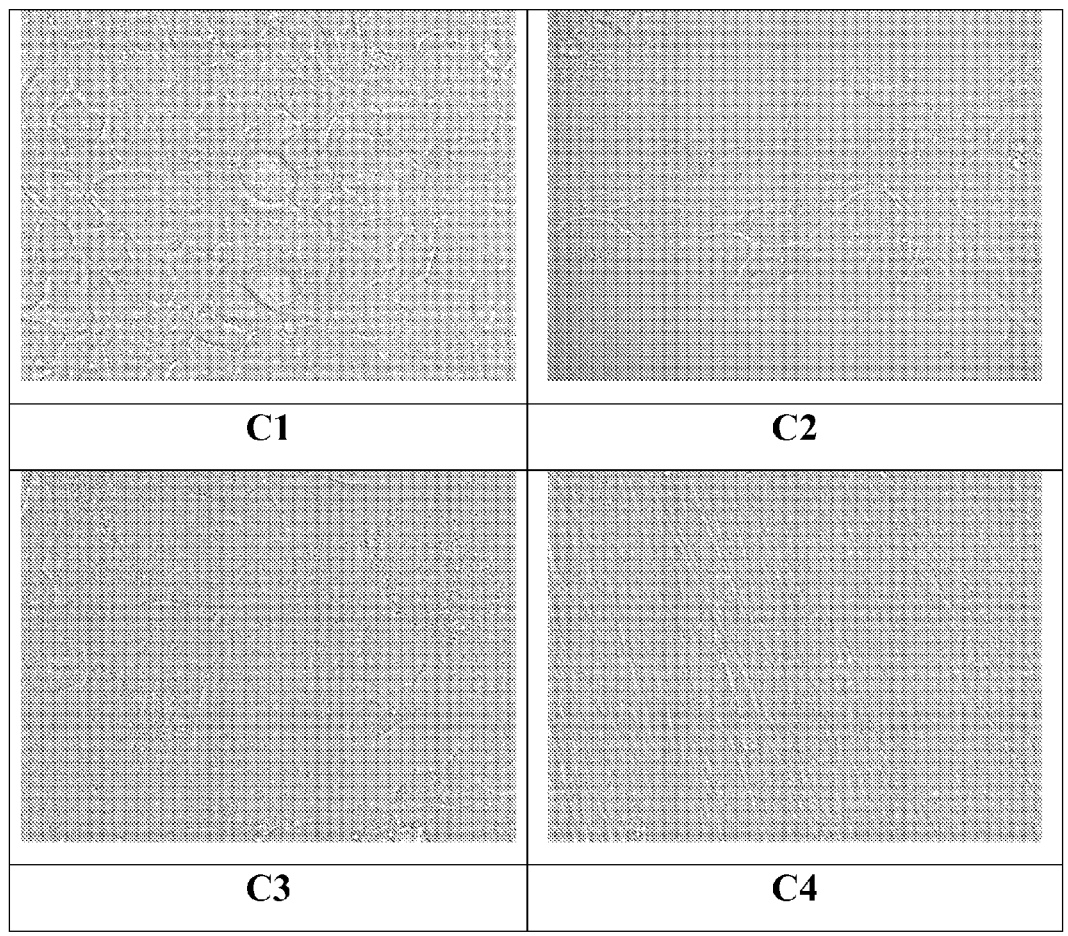
FIG. 4c shows the effect of non-functionalized microbubbles on (C1) MCF-7; (C2) MCF-10A; (C3) A-549; and (C4) CCL-75 cells.

Overall, most of the cell line pairs exhibited the same tumor specificity as the model MCF-7/MCF-10A lines, as represented by A-549/CCL-75 (FIGS. 4a-c). Of the seven new cell lines tested (besides MCF-7 and MCF-10A), four cell lines showed complete tumor cell selectivity using the disaccharide-linked microbubbles. Two cell lines pairs exhibited positive attachment in the 'normal' counterparts. However, in both cases, the 'normal' cell lines had been transformed with Human Papillomavirus (HPV) strains. For instance, 'normal' CRL-2221 prostate cells were transformed with HPV-18, and 'normal' CRL-2305 kidney cells were transformed with HPV-16. Hence, the positive attachment result has been attributed to these changes to the cells. In the case of CRL-7622/CCL-211 cell pair, no attachment was seen at all. This may reflect the fact that bleomycin usually exhibits efficacy toward soft cell carcinomas, and thus its effect could be limited when it comes to osteons. Despite the results in the HPV-transformed cells, there was still greater attachment in the tumor counterpart as opposed to its 'normal' complement.

Example 37

Visualization of Cell Association of Fluorescent-Disaccharide Probe

Since the disaccharide moiety was shown to possess all of the information required for tumor cell recognition, we wanted to determine if the carbohydrate could direct the introduction of other compounds to the cancer cell. In this case, we tethered a non-fluorescent pro-fluorophore, 5(6)-carboxyfluorescein diacetate (CFSE) onto the disaccharide of bleomycin to create a BLM-sugar probe. This fluorophore should only fluoresce when acted upon by the cell, where intracellular esterases cleave the acetate groups allowing for detectable fluorescence.

Both A-549 lung carcinoma cells and CCL-75 normal lung fibroblasts were seeded on 35 mm glass cover slips at a density of $2.5 \times 10^5$ cells before incubating 48 hours to allow attachment and growth. A total effective concentration of 1 fM of the fluorescent-sugar derivative (34) and 5(6)-carboxyfluorescein diacetate N-succinimidyl ester (CFSE) compounds were added to cover slips of each cell type before incubation for five minutes at 37° C. To prepare slides for microscopy viewing, cover slips were washed in PBS and 70% ethanol solution before fixation in Histochoice MB Fixative (Electron Microscopy Sciences, Hatfield, Pa.) for 15 minutes. Fixed cover slips were mounted onto glass slides for viewing. Using the Zeiss Axiovert 200M inverted microscope (Apotome camera), fluorescent images were acquired using DIC (at 35 ms exposure time) and appropriate fluorescence filter at 470-490 nm excitation (761 ms exposure time), 40× objective magnification.

Figure 5A:
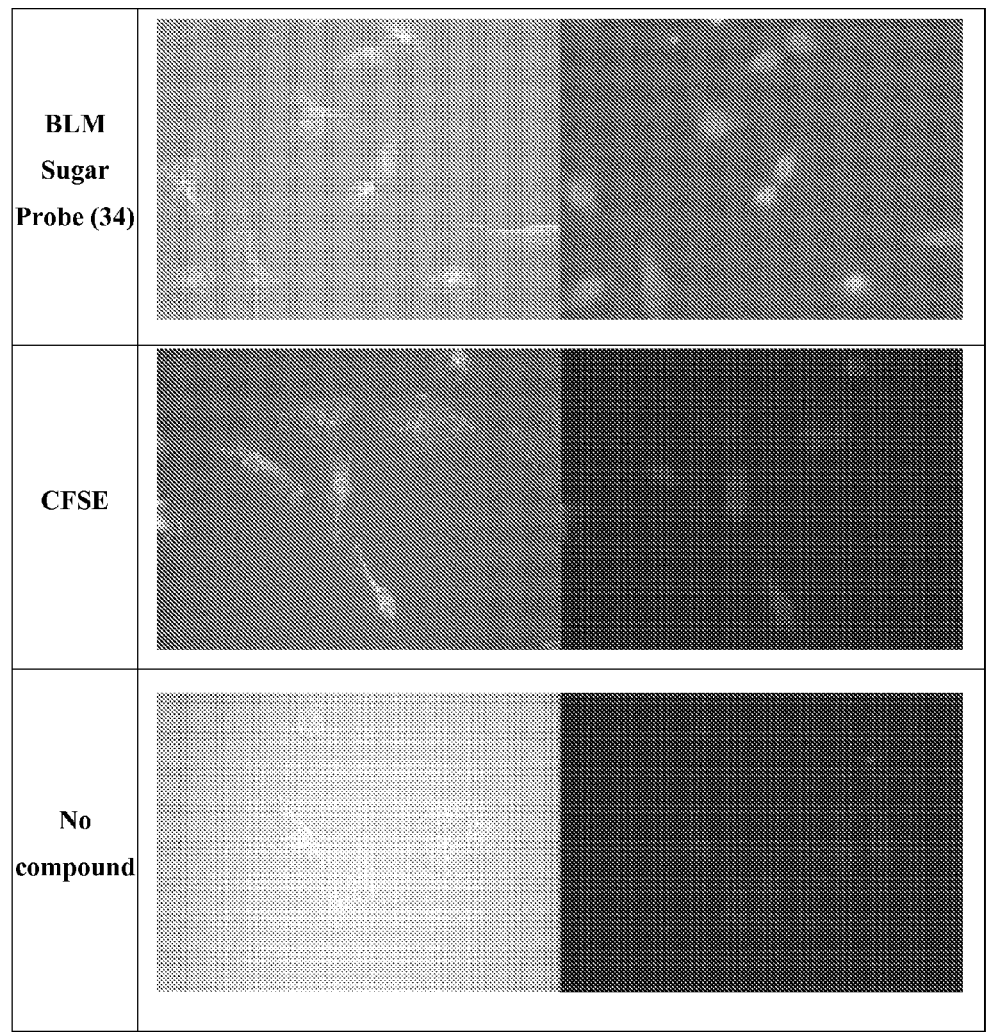
FIG. 5a shows fluorescent-sugar conjugate (34) association at 1 fM concentration by A-549 tumor cells (top row); the middle row shows the same tumor cells exposed to only 5(6)-carboxyfluorescein diacetate (CFSE); the bottom row shows a negative control in which no compound was added and shows background fluorescence due to autofluorescence. The left hand column shows differential interference contrast (DIC) imaging. The right hand column shows corresponding fluorescence at 494 nm.
Figure 5B:
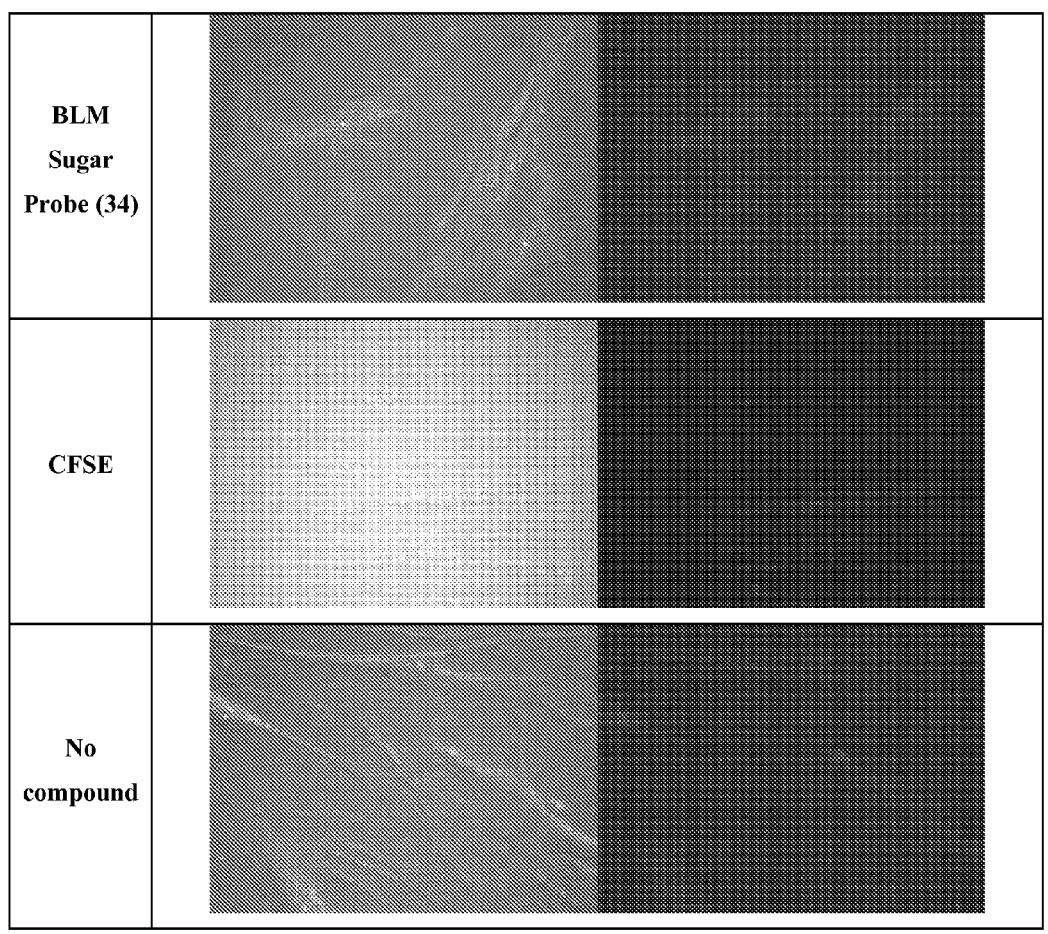
FIG. 5b shows fluorescent-sugar conjugate (34) association at 1 fM concentration by CCL-75 tumor cells (top row); the middle row shows the same tumor cells exposed to only 5(6)-carboxyfluorescein diacetate (CFSE); the bottom row shows a negative control in which no compound was added and shows background fluorescence due to autofluorescence. The left hand column shows differential interference contrast (DIC) imaging. The right hand column shows corresponding fluorescence at 494 nm.

A representative pair of cell lines (A-549/CCL-75) is shown in FIGS. 5a and 5b, respectively. A negative control (no compound added to cells) was performed to determine the autofluorescence of cells, which was considered background in the other images taken. As one can see in FIG. 5, at this dilute fluorophore concentration, the BLM-sugar probe exhibited the highest fluorescence only in the tumor cell line, A-549. Furthermore, the lack of marked fluorescence upon addition of fluorophore CFSE indicates that the sugar is important for the specific association with the A-549 cells.

These results document the unanticipated finding that the biotinylated disaccharide of bleomycin can be used to effect and monitor interaction with tumor cells. In the case of MCF-7 cells, the biotinylated sugar actually exhibited greater attachment than biotinylated bleomycin $A_5$.

The disaccharide moiety of bleomycin contains all of the information necessary for tumor cell recognition and targeting. When bleomycin lacks its carbohydrate, its tumor-specific nature is eliminated. Since disaccharide accumulation is shown to be selective in most tumor cell lines tested, it is envisioned that this interaction can form the basis for methods for the specific recognition and targeting of cancer cells in general. Applications in tumor diagnostics and the delivery of chemotherapeutic agents can be readily envisioned.

We claim:
1. A compound according to the formula,

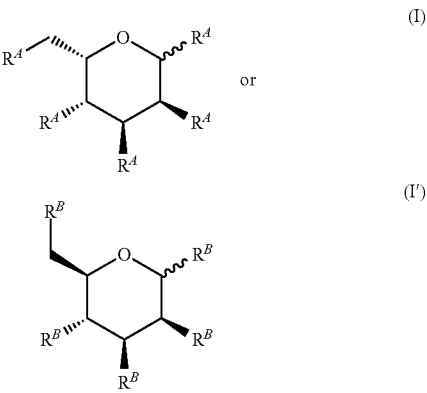

an epimer thereof, or a pharmaceutically acceptable salt thereof, wherein each $R^A$ is independently hydrogen, —$OR^1$, —$N(H)(R^1)$, or —$R^4$, wherein each $R^1$ is independently hydrogen, a protecting group, —$R^3$, —$R^4$, or —$R^{5a}$, wherein $R^{5a}$ is

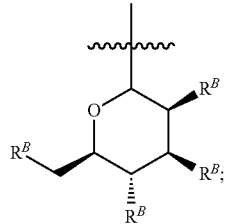

each $R^B$ is independently hydrogen, —$OR^2$, —$N(H)(R^2)$, or —$R^4$, wherein each $R^2$ is independently hydrogen, a protecting group, —$R^3$, —$R^4$, or —$R^{5b}$, wherein $R^{5b}$ is

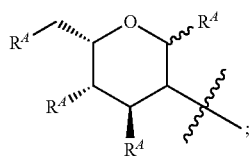

$R^3$ is —$C(O)OR^{30}$, —$C(O)N(H)(R^{30})$, —$S(O)OR^{30}$, —$S(O)_2OR^{30}$, —$S(O)N(H)(R^{30})$, —$S(O)_2N(H)(R^{30})$, or —$P(O)(OR^{30})_2$, wherein $R^{30}$ is hydrogen, $C_1$-$C_6$ alkyl, $C_1$-$C_6$ haloalkyl, aryl, heteroaryl, $C_3$-$C_8$ cycloalkyl, or heterocyclyl, wherein $R^{30}$ is optionally substituted with one to four groups which are each independently $C_1$-$C_6$ alkyl, cyano, nitro, halogen, —$OR^{31}$, —$N(R^{31})_2$, —$SR^{31}$, —$C(O)R^{31}$, —$C(O)OR^{31}$, —$C(O)N(R^{31})_2$, —$OC(O)OR^{31}$, —$OC(O)N(R^{31})_2$, —$N(R^{31})C(O)OR^{31}$, —$N(R^{31})C(O)N(R^{31})_2$, —$S(O)R^{31}$, —$S(O)_2R^{31}$, —$S(O)N(R^{31})_2$, or —$S(O)_2N(R^{31})_2$, wherein each $R^{31}$ is independently hydrogen or $C_1$-$C_6$ alkyl;

each $R^4$ is independently -L-$(R^{40})_q$, wherein each q is independently one or greater;

each L is independently —$C_1$-$C_{20}$ alkyl-, —$C_2$-$C_{20}$ alkenyl-, —$C_2$-$C_{20}$ alkynyl-, -aryl-, -heteroaryl-, -heterocyclyl-, —$C_3$-$C_8$ cycloalkyl-, an oligoalkylene glycol, an oligopeptide, a dendrimer, or -($L^1$-Y)$_n$-$L^2$-X—, wherein Y is —O—, —S—, or —$N(R^Y)$—, wherein $R^Y$ is hydrogen or $C_1$-$C_6$ alkyl; n is an integer selected from 1 to 250; $L^1$ is —$C_2$-$C_6$ alkyl-; $L^2$ is —$C_1$-$C_{20}$ alkyl-, —$C_2$-$C_{20}$ alkenyl-, —$C_2$-$C_{20}$ alkynyl-, -aryl-, -heteroaryl-, -heterocyclyl-, —$C_3$-$C_8$ cycloalkyl-; and X is a bond, —O—, —$N(R^X)$, —S—, —C(O)—, —S(O)—, —$S(O)_2$—, —OC(O)—, —$N(R^X)C(O)$—, —$N(R^X)S(O)$—, —$N(R^X)S(O)_2$—, —C(O)O—, —$C(O)N(R^X)$—, —$S(O)N(R^X)$—, —$S(O)_2N(R^X)$—, —OC(O)O—, —$OC(O)N(R^X)$—, —$N(R^X)C(O)O$—, —$N(R^X)C(O)N(R^X)$—, or —$N(R^X)S(O)_2N(R^X)$—, wherein each $R^X$ is independently hydrogen or $C_1$-$C_6$ alkyl, provided that when L is a bond, then q is 1; and each $R^{40}$ is independently an imaging agent, a member of a specific binding pair, a chemotherapeutic agent, or —$R^{41}$, wherein $R^{41}$ is —OH, —$NH(R^{42})$, —SH, —C(O)H, —C(O)$OR^{42}$, —$C(O)NH(R^{42})$, —$OC(O)OR^{42}$, —OC(O)$N(R^{42})_2$, —$N(R^{42})C(O)OR^{42}$, —$N(R^{42})C(O)N(R^{42})_2$, —$S(O)N(R^{42})_2$, or —$S(O)_2N(R^{42})_2$, wherein each $R^{42}$ is independently hydrogen, $C_1$-$C_6$ alkyl, or benzyl; and provided that (i) no more than one $R^1$ is $R^{5a}$ and no more than one $R^2$ is $R^{5b}$;

(ii) when one $R^1$ group is $R^{5a}$, then $R^2$ is not $R^{5b}$; and when one $R^2$ group is $R^{5b}$, then $R^1$ is not $R^{5a}$;

(iii) no more than one $R^3$ group is present;

(iv) at least one $R^4$ is present;

(v) no more than one $R^A$, and no more than one $R^B$ comprises $R^4$;

(vi) no more than two $R^A$ groups and no more than two $R^B$ groups are hydrogen;

(vii) $R^{40}$ is not (a) $R^{41}$ when L is a bond; and (b) bleomycin; and (viii) the compound of formula (I) or (I') is not bleomycin.

2. The compound of claim 1 according to the formula,

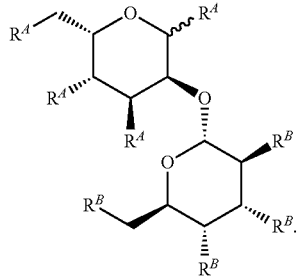

3. The compound of claim 2, wherein one $R^A$ group is —$N(H)(R^1)$; each of the remaining $R^A$ groups is —$OR^1$; and each $R^B$ is —$OR^2$.

4. The compound of claim 2, wherein one $R^A$ group is —$N(H)(R^1)$; each of the remaining $R^A$ groups is —$OR^1$; and each $R^B$ is —$OR^2$.

5. The compound of claim 2, wherein one $R^B$ group is —$N(H)(R^2)$; each of the remaining $R^B$ groups is —$OR^2$; and each $R^A$ is —$OR^1$.

6. The compound of claim 2, wherein one $R^A$ group is hydrogen; each of the remaining $R^A$ groups is —$OR^1$; and each $R^B$ is —$OR^2$.

7. The compound of claim 2, wherein one $R^B$ group is hydrogen; each of the remaining $R^B$ group is —$OR^2$; and each $R^A$ is —$OR^1$.

8. The compound of claim 1 according to the formula,

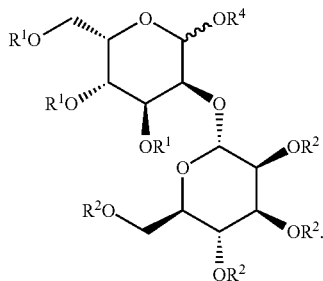

9. The compound of claim 1 according to the formula,

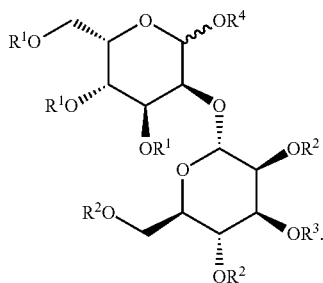

10. The compound of claim 1, wherein each $R^1$ and $R^2$ is independently a protecting group.

11. The compound of claim 1, wherein each $R^1$ and $R^2$ is independently a protecting group, wherein each protecting group is independently —C(O)$R^{40}$ or benzyl, wherein $R^{40}$ is $C_1$-$C_6$ alkyl, halomethyl, dihalomethyl, trihalomethyl, or $C_1$-$C_4$alkoxymethyl.

12. The compound of claim 1, wherein each $R^1$ and $R^2$ is hydrogen.

13. The compound of claim 1, wherein $R^3$ is —C(O)O$R^{30}$ or —C(O)N(H)($R^{30}$).

14. The compound of claim 1, wherein $R^3$ is —C(O)N(H)($R^{30}$), wherein $R^{30}$ is hydrogen or $C_1$-$C_6$ alkyl.

15. The compound of claim 1, wherein $R^3$ is —C(O)NH$_2$.

16. The compound of claim 1, wherein q is 1.

17. The compound of claim 16, wherein $L^1$ is —$C_2$-$C_4$ alkyl-; $L^2$ is —$C_1$-$C_6$ alkyl-; and X is a bond, —O—, —N($R^X$), —S—, —C(O)—, —S(O)—, or —S(O)$_2$—.

18. The compound of claim 17, wherein L is —(CH$_2$CH$_2$—O)$_n$—CH$_2$CH$_2$—X—, wherein X is —O—, —N(H), or —S— and n is an integer selected from 1 to 20.

19. The compound of claim 17, wherein L is —(CH$_2$CH$_2$—O)$_n$—CH$_2$CH$_2$—X—, wherein X is —C(O)— or —S(O)$_2$— and n is an integer selected from 1 to 20.

20. The compound of claim 1, wherein $R^{40}$ is —$R^{41}$.

21. The compound of claim 1, wherein $R^{40}$ is an imaging agent.

22. The compound of claim 1, wherein $R^{40}$ is a fluorescent imaging agent.

23. The compound of claim 1, wherein $R^{40}$ is an imaging agent comprising a chelating group coordinated to a radioactive imaging moiety.

24. The compound of claim 1, wherein $R^{40}$ is a member of a specific binding pair.

25. The compound of claim 24, wherein $R^{40}$ is a member of a specific binding pair, selected from biotin-streptavidin and biotin-avidin.

26. The compound of claim 1, wherein $R^{40}$ is a chemotherapeutic agent.

27. The compound of claim 1 which is
(2R,3R,4S,5S,6R)-2-(acetoxymethyl)-4-(carbamoyloxy)-6-((2R,3S,4S,5R,6S)-4,5-diacetoxy-6-(acetoxymethyl)-2-(2-(2-(benzyloxycarbonylamino)ethoxy)ethoxy)tetrahydro-2H-pyran-3-yloxy)tetrahydro-2H-pyran-3,5-diyl diacetate;
(2R,3R,4S,5S,6R)-2-(acetoxymethyl)-4-(carbamoyloxy)-6-((2R,3S,4S,5R,6S)-4,5-diacetoxy-6-(acetoxymethyl)-2-(2-(2-(5-((3aS,4S,6aR)-2-oxohexahydro-1H-thieno[3,4-d]imidazol-4-yl)pentanamido)ethoxy)ethoxy)tetrahydro-2H-pyran-3-yloxy)tetrahydro-2H-pyran-3,5-diyl diacetate; or
(2R,3S,4S,5R,6R)-2-((2R,3S,4S,5S,6S)-4,5-dihydroxy-6-(hydroxymethyl)-2-(2-(2-(5-((3aS,4S,6aR)-2-oxohexahydro-1H-thieno[3,4-d]imidazol-4-yl)pentanamido)ethoxy)ethoxy)tetrahydro-2H-pyran-3-yloxy)-3,5-dihydroxy-6-(hydroxymethyl)tetrahydro-2H-pyran-4-yl carbamate,
(2R,3S,4S,5R,6R)-24(2R,3S,4S,5S,6S)-2-(2-(2-Benzyloxycarbonylaminoethoxy)ethoxy)-4,5-dihydroxy-6-(hydroxymethyl)tetrahydro-2H-pyran-3-yloxy)-3,5-dihydroxy-6-(hydroxymethyl)tetrahydro-2H-pyran-4-yl carbamate;
(4,5)-(2-(2-((2R,3S,4S,5S,6S)-34(2R,3S,4S,5R,6R)-4-(Carbamoyloxy)-3,5-dihydroxy-6-(hydroxymethyl)tetrahydro-2H-pyran-2-yloxy)-4,5-dihydroxy-6-(hydroxymethyl)tetrahydro-2H-pyran-2-yloxy)ethoxy)ethylcarbamoyl)-3-oxo-3H-spiro[isobenzofuran-1,9'-xanthene]-3',6'-diyl Diacetate;
or a pharmaceutically acceptable salt thereof.

28. A pharmaceutical composition comprising a compound according to claim 1, wherein $R^{40}$ is a chemotherapeutic agent, and a pharmaceutically acceptable diluent, carrier, or excipient.

29. A composition comprising a compound according to claim 1, wherein $R^{40}$ is an imaging agent, and a pharmaceutically acceptable diluent, carrier, or excipient.

30. A microbubble conjugate comprising
(a) a microbubble comprising an outer shell, wherein the outer shell is derivatized with a first member of a specific binding pair; and
(b) a compound according to claim 1, wherein $R^{40}$ is a second member of the specific binding pair, bound to the microbubble, wherein the first member of the specific binding pair and the second member of the specific binding pair are bound to each other.

31. A microbubble conjugate comprising
(a) a microbubble comprising an outer shell, wherein the outer shell is derivatized with a first member of a specific binding pair;
(b) a compound according to claim 1, wherein $R^{40}$ is a first member of the specific binding pair, and
(c) a second member of the specific binding pair, wherein the second member of the specific binding pair binds to both first members of a specific binding pair, thereby binding the compound to the microbubble.

32. The microbubble conjugate of claim 30, wherein the first member of the specific binding pair is biotin and the second member of the specific binding pair is streptavidin or avidin.

33. A composition comprising a microbubble conjugate according to claim 30, and a pharmaceutically acceptable diluent, carrier, or excipient.

34. A method for selectively imaging a tumor in a patient comprising, administering to a subject with a tumor a compound according to claim 1, wherein $R^{40}$ is an imaging agent under conditions suitable to promote binding of the compound to the tumor; and detecting a signal from the imaging agent or microbubble conjugate.

35. A method for treating a tumor in a patient in need of such treatment comprising administering to the patient a therapeutically effective amount of a compound according to claim 1, wherein $R^{40}$ is an chemotherapeutic agent.

* * * * *

UNITED STATES PATENT AND TRADEMARK OFFICE
CERTIFICATE OF CORRECTION

PATENT NO. : 9,624,255 B2
APPLICATION NO. : 13/382581
DATED : April 18, 2017
INVENTOR(S) : Sidney Hecht et al.

It is certified that error appears in the above-identified patent and that said Letters Patent is hereby corrected as shown below:

On the Title Page

(73) "Assignee: Arizona Board of Regents, Scottsdale, AZ (US)" should be --Assignee: Arizona Board of Regents, a body corporate of the state of Arizona, acting for and on behalf of Arizona State University, Scottsdale, AZ (US)--

In the Claims

Claim 27, Line 21-25, "(2R,3S,4S,5R,6R)-24(2R,3S,4S,5S,6S)-2-(2-(2-Benzyloxycarbonylaminoethoxy) ethoxy)-4,5 -dihydroxy-6-(hydroxymethyl)tetrahydro-2H-pyran-3-yloxy)-3,5-dihydroxy-6-(hydroxymethyl)tetrahydro-2H-pyran-4-yl carbamate;" should be --(2R,3S,4S,5R,6R)-2-((2R,3S,4S,5S,6S)-2-(2-(2-Benzyloxycarbonylaminoethoxy)ethoxy)-4,5-dihydroxy-6-(hydroxymethyl)tetrahydro-2H-pyran-3-yloxy)-3,5-dihydroxy-6-(hydroxymethyl)tetrahydro-2H-pyran-4-yl carbamate;--

Claim 27, Line 26-31, "(4,5)-(2-(2-((2R,3S,4S,5S,6S)-34(2R,3S,4S,5R,6R)-4-(Carbamoyloxy)-3,5-dihydroxy-6-(hydroxymethyl)tetrahydro-2H-pyran-2-yloxy)-4,5-dihydroxy-6-(hydroxymethyl)tetrahydro-2H-pyran-2-yloxy)et581hoxy)ethylcarbamoyl)-3-oxo-3H-spiro[isobenzofuran-l ,9'-xanthene]-3',6'-diyl Diacetate;" should be --(4,5)-(2-(2-((2R,3S,4S,5S,6S)-3-((2R,3S,4S,5R,6R)-4-(Carbamoyloxy)-3,5-dihydroxy-6-(hydroxymethyl)tetrahydro-2H-pyran-2-yloxy)-4,5-dihydroxy-6-(hydroxymethyl)tetrahydro-2H-pyran-2-yloxy)ethoxy)ethylcarbamoyl)-3-oxo-3H-spiro[isobenzofuran-l ,9'-xanthene]-3',6'-diyl Diacetate;--

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*